United States Patent
Reasoner et al.

(10) Patent No.: US 10,105,470 B2
(45) Date of Patent: Oct. 23, 2018

(54) MOBILE INSTRUMENT ASSEMBLY FOR USE AS PART OF A MEDICAL/SURGICAL WASTE COLLECTION SYSTEM, THE ASSEMBLY INCLUDING A VACUUM SOURCE TO WHICH A MOBILE WASTE COLLECTION CART CAN BE RELEASABLY ATTACHED

(71) Applicant: Stryker Corporation, Kalamazoo, MI (US)

(72) Inventors: Stephen J. Reasoner, Kalamazoo, MI (US); Bruce Henniges, Galesburg, MI (US); Steven Carusillo, Kalamazoo, MI (US); Brian MacLachlan, Norton Shores, MI (US)

(73) Assignee: Stryker Corporation, Kalamazoo, MI (US)

( * ) Notice: Subject to any disclaimer, the term of this patent is extended or adjusted under 35 U.S.C. 154(b) by 468 days.

(21) Appl. No.: 14/691,613

(22) Filed: Apr. 21, 2015

(65) Prior Publication Data

US 2015/0224237 A1 Aug. 13, 2015

Related U.S. Application Data

(63) Continuation of application No. PCT/US2013/066101, filed on Oct. 22, 2013.

(Continued)

(51) Int. Cl.
*A61M 1/00* (2006.01)
*A61B 5/00* (2006.01)
(Continued)

(52) U.S. Cl.
CPC ......... *A61M 1/0003* (2013.01); *A61B 5/6887* (2013.01); *A61B 17/00* (2013.01);
(Continued)

(58) Field of Classification Search
CPC ............. A61M 1/0023; A61B 17/00; A61B 2017/00017; A61B 2017/005; A61B 2017/007
See application file for complete search history.

(56) References Cited

U.S. PATENT DOCUMENTS 6,770,061 B2 8/2004 Wildman
7,516,924 B2 4/2009 White et al.
(Continued)

FOREIGN PATENT DOCUMENTS

CN 101370535 A 2/2009
CN 101597320 A 12/2009
(Continued)

OTHER PUBLICATIONS

PCT "International Search Report and Written Opinion" for PCT/US2013/066101, dated May 23, 2014.
(Continued)

*Primary Examiner* — Tatyana Zalukaeva
*Assistant Examiner* — Kai Weng
(74) *Attorney, Agent, or Firm* — Howard & Howard Attorneys PLLC

(57) ABSTRACT

A waste collection system for collecting waste during medical/surgical procedures including a mobile container cart with a waste container. A container cart is selectively coupled to a suction cart that includes a vacuum pump. The connection of the carts results in the connection of the vacuum pump to the waste container. The vacuum pump draws a vacuum that results in waste being drawn through a suction line into the waste container. The container cart holds instruments that can be removably attached to the container cart. This facilitates the configuration of the container cart for the specific procedure for which it is necessary to draw a suction.

20 Claims, 49 Drawing Sheets

Related U.S. Application Data

(60) Provisional application No. 61/717,793, filed on Oct. 24, 2012.

(51) Int. Cl.
  *A61B 17/00* (2006.01)
  *A61M 39/10* (2006.01)
  *A61B 50/10* (2016.01)
  *A61B 50/13* (2016.01)

(52) U.S. Cl.
  CPC .............. *A61B 50/10* (2016.02); *A61B 50/13* (2016.02); *A61M 1/0001* (2013.01); *A61M 1/0005* (2013.01); *A61M 1/0023* (2013.01); *A61M 1/0031* (2013.01); *A61M 1/0052* (2014.02); *A61M 39/10* (2013.01); *A61B 2017/00017* (2013.01); *A61B 2217/005* (2013.01); *A61B 2217/007* (2013.01); *A61B 2560/0437* (2013.01); *A61M 2205/0272* (2013.01); *A61M 2205/05* (2013.01); *A61M 2205/3331* (2013.01); *A61M 2205/3576* (2013.01); *A61M 2205/52* (2013.01); *A61M 2209/084* (2013.01)

(56) References Cited

U.S. PATENT DOCUMENTS

| | | | |
|---|---|---|---|
| 7,615,037 | B2 | 11/2009 | Murray et al. |
| 7,621,898 | B2 | 11/2009 | Lalomia et al. |
| 8,088,079 | B2 | 1/2012 | Kaye et al. |
| 8,506,798 | B2 | 8/2013 | Beulay et al. |
| 9,532,843 | B2 | 1/2017 | Palmerton et al. |
| 9,592,329 | B2 | 3/2017 | Pohlmeier et al. |
| 9,782,524 | B2 | 10/2017 | Reasoner et al. |
| 2002/0111592 | A1 | 8/2002 | Bemis et al. |
| 2005/0187529 | A1 | 8/2005 | Reasoner et al. |
| 2009/0012485 | A1 | 1/2009 | Michaels et al. |
| 2010/0206785 | A1 | 8/2010 | Beulay et al. |

FOREIGN PATENT DOCUMENTS

| | | |
|---|---|---|
| CN | 102475922 A | 5/2012 |
| CN | 202437772 U | 9/2012 |
| EP | 1480594 B1 | 8/2009 |
| GB | 2465951 B | 10/2012 |
| JP | 2007209764 A | 8/2007 |
| WO | 9900154 A1 | 1/1999 |
| WO | 2004075740 A1 | 9/2004 |
| WO | 2008/118398 A1 | 10/2008 |
| WO | 2011113572 A1 | 9/2011 |
| WO | 2014066337 A2 | 5/2014 |
| WO | 2014117043 A1 | 7/2014 |
| WO | 2015164384 A1 | 10/2015 |

OTHER PUBLICATIONS

English language abstract for CN 101370535 extracted from espacenet.com database on Nov. 30, 2017, 2 pages.

English language abstract for CN 101597320 extracted from espacenet.com database on Nov. 30, 2017, 2 pages.

English language abstract and machine-assisted English translation for CN 102475922 extracted from espacenet.com database on Nov. 30, 2017, 7 pages.

English language abstract and machine-assisted English translation for CN 202437772 extracted from espacenet.com database on Nov. 30, 2017, 5 pages.

English language abstract for JP 2007-209764 extracted from espacenet.com database on Nov. 30, 2017, 1 page.

English language abstract for WO 2004/075740 extracted from espacenet.com database on Nov. 30, 2017, 2 pages.

English language abstract for WO 2011/113572 extracted from espacenet.com database on Mar. 28, 2018, 2 pages.

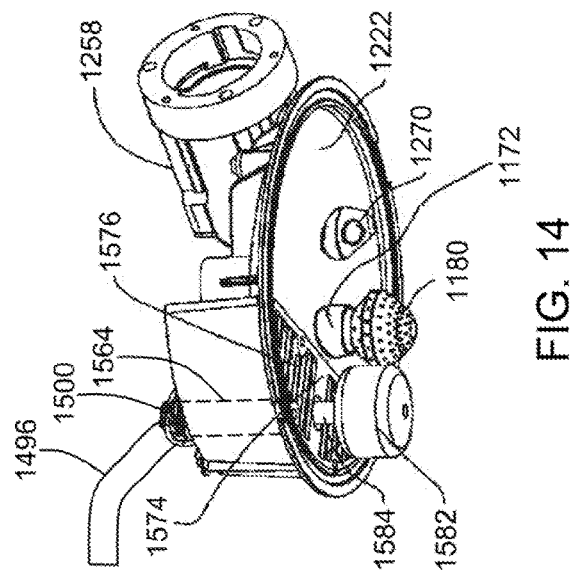
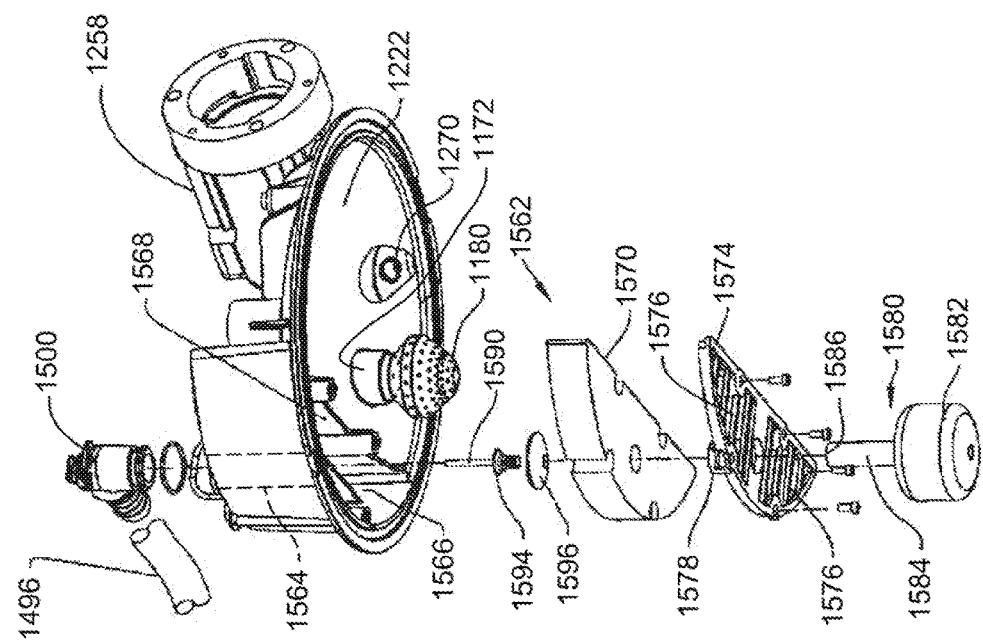

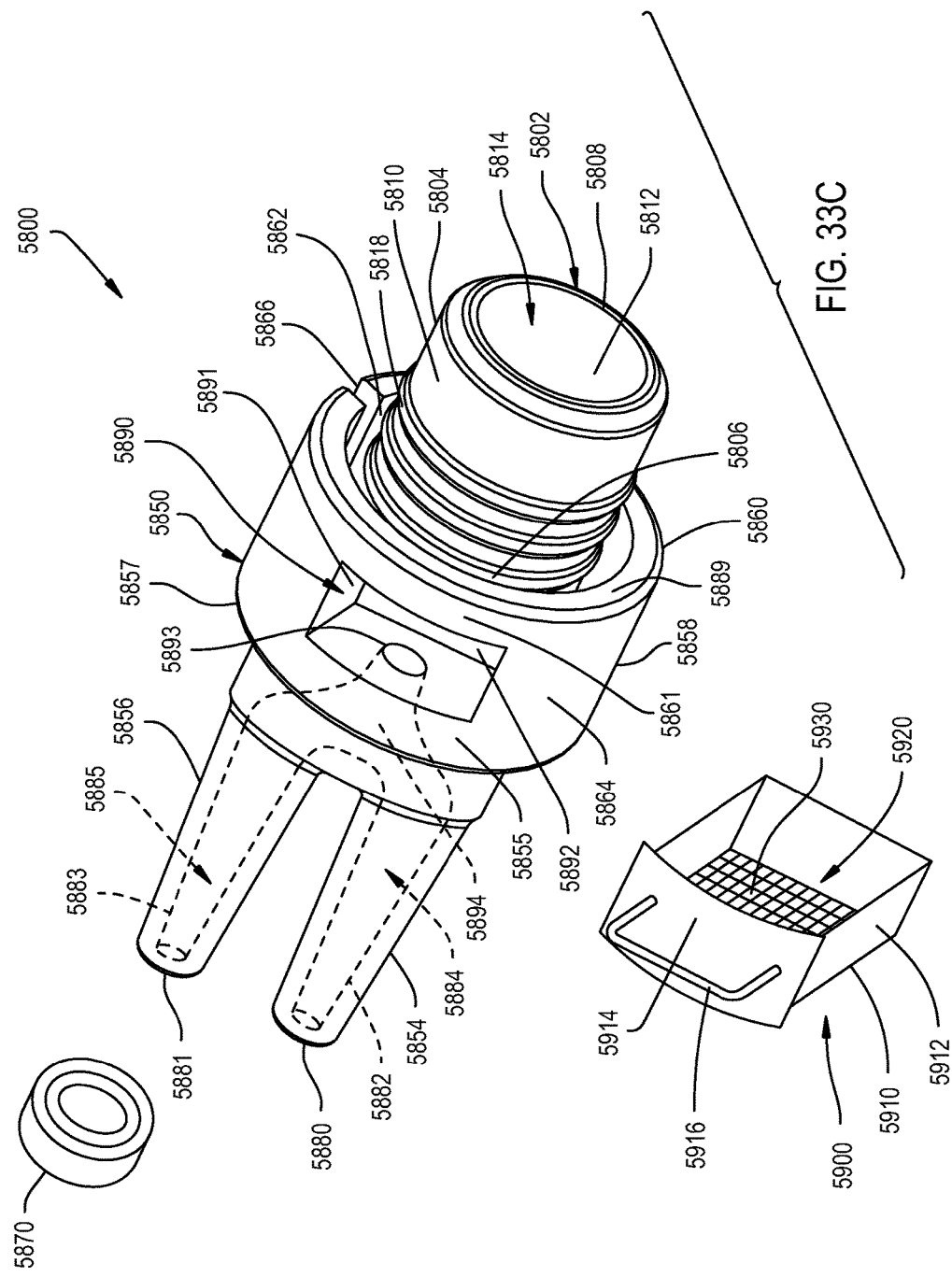

MOBILE INSTRUMENT ASSEMBLY FOR
USE AS PART OF A MEDICAL/SURGICAL
WASTE COLLECTION SYSTEM, THE
ASSEMBLY INCLUDING A VACUUM
SOURCE TO WHICH A MOBILE WASTE
COLLECTION CART CAN BE RELEASABLY
ATTACHED

FIELD OF THE INVENTION

This invention relates generally to waste collection systems for the collection of medical waste generated during medical and surgical procedures. More particularly, this invention relates to a waste collection system that is easily transportable within a surgical facility and that can hold a large volume of medical waste.

BACKGROUND OF THE INVENTION

A byproduct of the performance of some medical and surgical procedures is the generation of liquid, semi-solid and solid waste. This waste includes body fluids, such as blood, and irrigating solutions that are introduced to the body site at which the procedure is performed. Solid and semisolid waste generated during a procedure includes bits of tissue and small pieces of the surgical material that may be left at the site. Ideally, the waste is collected upon generation so it neither fouls the surgical site nor becomes a biohazard in the operating room or other location at which the procedure is being performed.

A number of systems are available for use by surgical personnel for collecting this waste as it is generated. Generally, these units include a suction source, tubing that extends from the suction source and a containment unit between the tubing and the suction source. When the system is actuated, waste is drawn through the opening end of the tubing. The suction draws the waste through the tubing so that it flows into and is stored in the containment unit. One such system is Applicants' Assignee's NEPTUNE surgical waste collection system. This particular system includes a mobile unit that includes a suction pump and two canisters. Tubing is connected to each canister through a removable manifold. Since this unit is mobile, it can be positioned in relatively close proximity to the patient on which the procedure is being performed. This reduces the extent to which the suction tubing, which invariably also functions as operating room clutter, is present around the surgical personnel. This system is wheeled away from the surgical location or operating room to a docking station to be emptied and cleaned. This system also has features that reduce the extent to which the surgical and support personnel are potentially exposed to the materials collected by the system. U.S. Pat. No. 7,621,898, issued Nov. 24, 2009, the contents of which are incorporated herein by reference, describes a number of features of this system.

The prior art waste collection systems have many advantages. There are some limitations that diminish their utility. First, because the suction pump is mounted to the mobile unit, where limited space is available for noise abatement materials and treatment methods, higher than desired noise levels may be present in close proximity to the surgical area. Second, current versions of the waste collection system can store on the order of 24 liters of medical/surgical waste. The weight of the mobile unit, with the containers filled close to capacity can be difficult for some medical personnel to move between the surgical location or operating room and the docking station.

SUMMARY OF THE INVENTION

This invention is directed to a new and useful waste collection system for the collection of medical waste generated during medical and surgical procedures. The system of this invention includes a mobile rover that can be selectively coupled and uncoupled with a mobile chassis. The mobile chassis has a chassis vacuum coupler and the mobile rover has a rover vacuum coupler. The rover vacuum coupler is connectable with the chassis vacuum coupler to form a vacuum seal between the mobile chassis and the mobile rover. A waste container is mounted to the mobile rover and is coupled with one or more suction lines. A vacuum source is mounted to the mobile chassis. The vacuum source provides a suction fluid communication path from the surgical site through the suction lines, the waste container, the rover vacuum coupler and the chassis vacuum coupler.

In many versions of this invention, the system also includes a static docker. The rover and docker are provided with complementary fluid couplings. The docker couplings are connected to a line through which waste fluid is transported for disposal.

The system of this invention is used by first positioning the chassis, with the rover attached, adjacent the location where the medical/surgical procedure is to be performed. A suction applicator and tubing is connected to the rover waste container. The chassis suction pump is actuated. The suction pump draws a suction on the suction applicator through the waste container. As a consequence of the suction draw, waste is drawn through the applicator and temporarily stored in the container.

When it is desired to empty the rover waste container, the rover is disconnected from the chassis. The rover is then moved to the docker. Once the rover is docked to the docker, the rover container is emptied. The waste is transferred through the docker fluid couplings into the connected disposal lines. Moving components from the mobile unit (Rover) to the chassis that stays in the OR reduces the weight and size of the device that is moved back and forth to the docker.

In an alternative version of the system of this invention, the chassis, the unit to which the suction pump is mounted is static. In these versions of the invention, prior to the start of the procedure, the rover is positioned to be mated to the chassis. During the procedure, the rover stays static with the chassis. When it is desired to empty the container, the rover is manually pushed from the chassis to the docker.

It is a further feature of this invention that the chassis functions as an instrument rack. More particularly, the chassis holds medical equipment, often power consoles that are used during the procedure in which the waste collection unit is employed. Since the power consoles or racked equipment used in a procedure are a function of the procedure, the chassis is designed so that this equipment can be removably attached to the chassis. Thus, the chassis is loaded with the equipment needed for the specific procedure prior to the start of the procedure.

When compared to having a separate equipment cart, combining the equipment rack with the chassis reduces the overall footprint occupied in the operating room. This creates additional valuable space around the surgical table and reduces clutter. Locating equipment in the same location as the surgical suction device simplifies routing of tubes and wires. The equipment rack reduces the number of power cords going to the wall, thereby eliminating trip hazards and making the positioning of other wheeled equipment easier in the operating room.

In versions of this invention wherein the chassis is a mobile chassis, the chassis thus serves as the device that is used to adjustably position not just the waste collection rover but, also the attached equipment, so it is in a position in the procedure room that the personnel using the equipment find most useful for the procedure.

A feature of the system of this invention is that different rovers can, at different times, be docked to the same docker. A medical facility that employs the system of this invention can have plural rovers and plural chassis's. Given that the individual rovers can be docked to the common docker, the system of this invention does not require the facility to provide a separate dedicated docker for each rover. In some facilities, it may only be necessary to provide a single docker for receiving the waste from all of the rovers. Another feature of the system of this invention is that different size rovers can be mated with the same chassis. The different size rovers can hold different amounts of medical waste.

BRIEF DESCRIPTION OF THE DRAWINGS

The invention is pointed out with particularity in the claims. The above and further features and advantages of the invention are understood by the following Detailed Description taken in conjunction with the accompanying drawings in which:

FIG. 13 is an exploded perspective view of the upper waste container cap;

FIG. 14 is an assembled perspective view of the upper waste container cap;

FIG. 33C is a perspective view of another embodiment of a disposable inlet fitting;

DETAILED DESCRIPTION

I. Overview

FIGS. 1-4 illustrate a medical/surgical waste collection system 50 constructed in accordance with this invention. Waste collection system 50 comprises a mobile chassis 100 and a mobile rover 1000. Mobile rover 1000 is mated with the mobile chassis 100 and is located in an operating room/surgical/medical care area 52 (FIG. 4) during use. Mobile chassis 100 is sometimes called a suction cart 100. Mobile rover 1000 is sometimes called a container cart or a mobile waste collection cart 1000.

Figure 2:
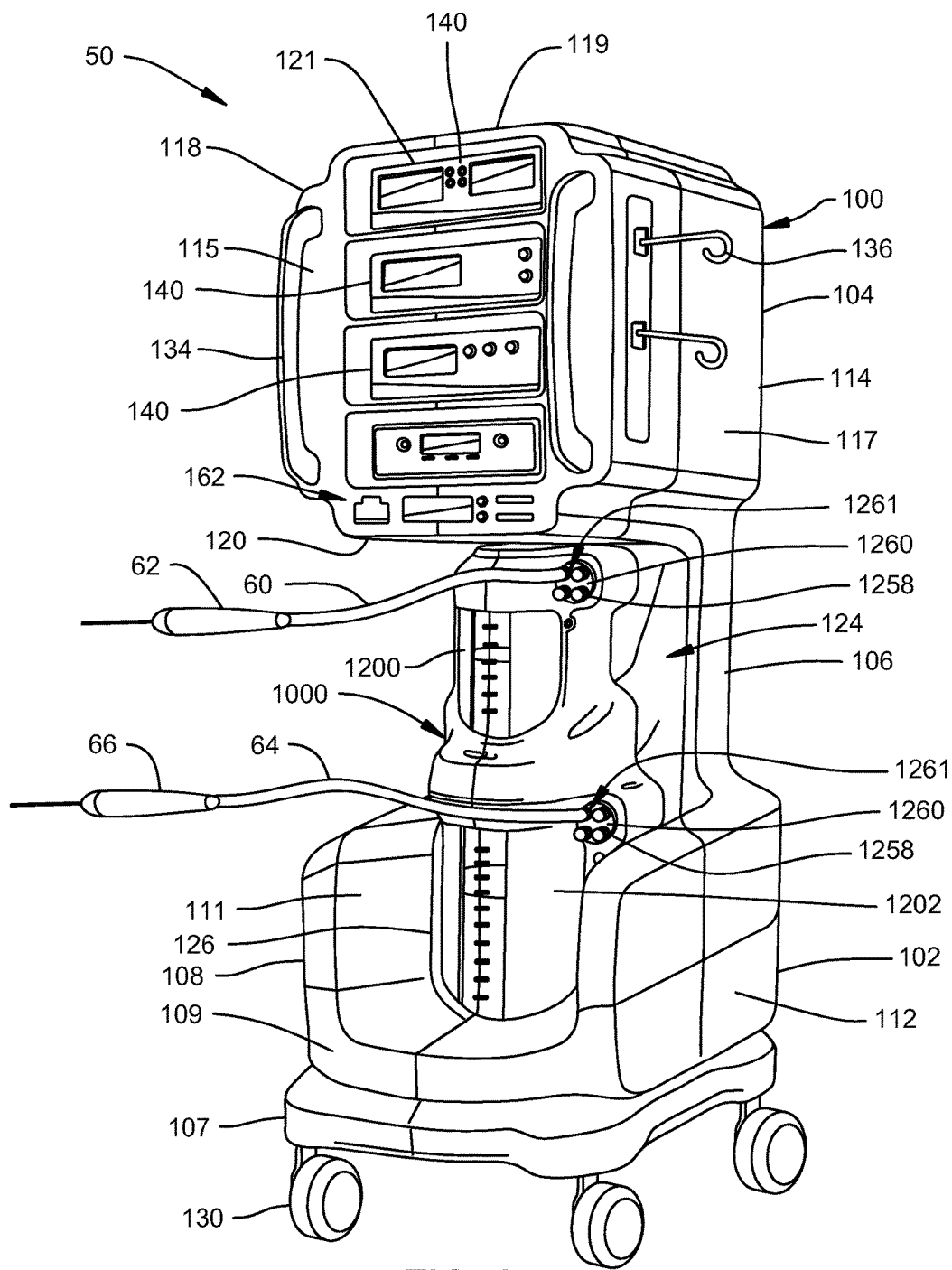
FIG. 2 is a front perspective view of the medical/surgical waste collection system illustrating the mobile rover mated with the mobile chassis in accordance with one embodiment.

With specific reference to FIG. 2, mobile rover 1000 includes a pair of manifolds 1260. Manifolds 1260 are formed with a number of fittings 1261. Manifolds 1260 are disclosed in further detail in the incorporated by reference U.S. Pat. No. 7,615,037. The exact structure of the manifolds is not part of this invention.

Fitting 1261 can receive a suction line 60 and the other fitting 1261 can receive another suction line 64. The distal end of each suction line 60 and 64 is attached to a suction applicator hand piece 62 and 66, respectively. In this application, "distal", generally refers to towards the surgical site at which the suction is applied and "proximal" refers to away from the surgical site. In some embodiments, suction applicator hand piece 62 and 66 can be built into another surgical tool, such as a surgical drill or biopsy tool or ablation tool, applied to a surgical site to accomplish a task other than applying suction.

Figure 3:
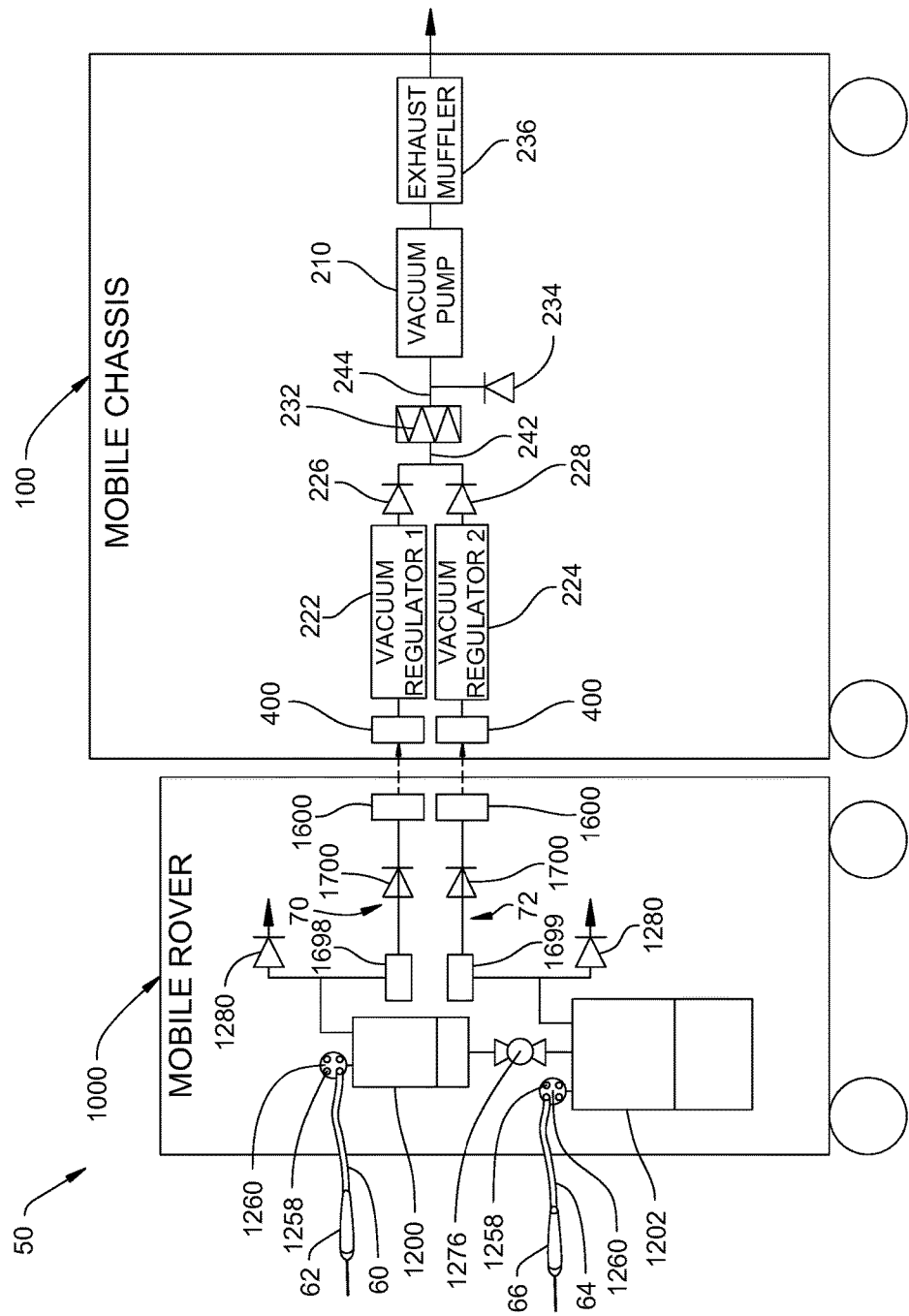
FIG. 3 is a diagrammatic view of the suction fluid communication paths according to one embodiment.

FIG. 3 illustrates a pair of continuous suction fluid communication paths 70 and 72 that are formed from the suction applicator 62 or 66 to the suction or vacuum pump 210 by the combination of mobile chassis 100 and mobile rover 1000. When vacuum pump 210 is in operation, the resultant suction draws waste matter into the respective suction applicator 62 or 66. The waste stream associated with suction fluid communication path 70 travels from the suction application 62, into mobile rover 1000 through manifold 1260 and into waste container 1200. The waste stream associated with suction fluid communication path 72 travels from the suction application 66, through manifold 1260 and into waste container 1202. Fluid communication paths 70 and 72 are sometimes called suction paths.

Liquid and small solid bits of matter entrained in this flow stream, that are not trapped in the manifold 1260 internal filter, precipitate out of the stream into respective waste containers 1200 or 1202. The waste is thus stored in the respective waste containers 1200 or 1202 until the canister is emptied. Gas and any matter entrained in this gas flow stream flow from the respective waste container 1200 or 1202 through check valves 1700 exiting the mobile rover 1000 and into the mobile chassis 100 through rover suction or vacuum couplers 1600 and chassis suction or vacuum couplers 400. Check valves 1280 are connected in parallel with respective suction fluid communication paths 70, 72 in order to provide an alternative means for supplying suction to waste containers 1200 and 1202.

A pressure sensor 1698 is in fluid communication with suction fluid communication path 70 to measure the level of vacuum drawn on the suction fluid communication path 70 and by extension container 1200. Pressure sensor 1698 generates a pressure signal that is corresponds to the vacuum level in suction fluid communication path 70. Similarly, another pressure sensor 1699 is in fluid communication with suction fluid communication path 72 in order to measure the level of vacuum drawn on the suction fluid communication path 72 and by extension container 1202. Pressure sensor 1699 generates a pressure signal that corresponds to the vacuum level in suction fluid communication path 72. While pressure sensors 1698 and 1699 are shown mounted between containers 1200, 1202 and check valves 1700, pressure sensors 1698 and 1699 can be mounted anywhere in their respective suction fluid communication paths 70, 72 upstream of vacuum regulators 222 and 224. In one embodiment, pressure sensor 1698 is mounted in container 1200 and pressure sensor 1699 is mounted in container 1202. In another embodiment, pressure sensors 1698 and 1699 are mounted in chassis Within mobile chassis 100, suction fluid communication path 70 includes chassis vacuum coupler 400, vacuum regulator 222, check valve 226, HEPA filter 232 and vacuum pump 210. Suction fluid communication path 72 in mobile chassis 100 includes chassis vacuum coupler 400, vacuum regulator 224, check valve 228, HEPA filter 232 and vacuum pump 210. A noise attenuator or exhaust muffler 236 is connected with vacuum pump 210 in order to reduce the noise level associated with the operation of vacuum pump 210.

The mobile rover 1000 includes a waste drain port 4902, described below, through which containers 1200 and 1202 are emptied. Mobile chassis 100 does not include a complementary coupling for receiving the material drained through the chassis waste drain port 1902. To empty containers 1200 and 1202 after use of the mobile rover, the mobile rover 1000 is uncoupled from the mobile chassis 100 and moved from the operating room/surgical area 52 to a static docking station or docker 900, depicted in FIG. 4. The static docker 900 is typically located remote from the operating room/surgical area 52. In one embodiment, static docker 900 is located proximate to several operating room/surgical areas 52 such that one or more mobile rovers 1000 can readily be emptied.

The rover 1000 and docker 900 are provided with complementary fluid couplings. The docker couplings include a waste port 902. Waste port 902 is configured to couple to waste port 1902 of rover 1000. When the rover 1000 is docked to the docker 900, these fluid couplings 902 and 1902 connect. These fluid couplings and the conduits internal to the docker 900 establish a fluid connection path from the rover containers 1200 and 1202 into the plumbing lines internal to the medical facility through which waste is transported for disposal.

When the rover is docked to docker 900, the waste in the rover containers is emptied through the docker. The docker also includes components that clean the mobile rover containers 1200 and 1202. The incorporated by reference U.S. Pat. No. 7,621,898, provides more detail about the structure of a docker and one set of rover to docker couplings. The exact structure of the docker and these couplings is not part of the present invention.

II. First Embodiment

A. Mobile Chassis

Figure 1:
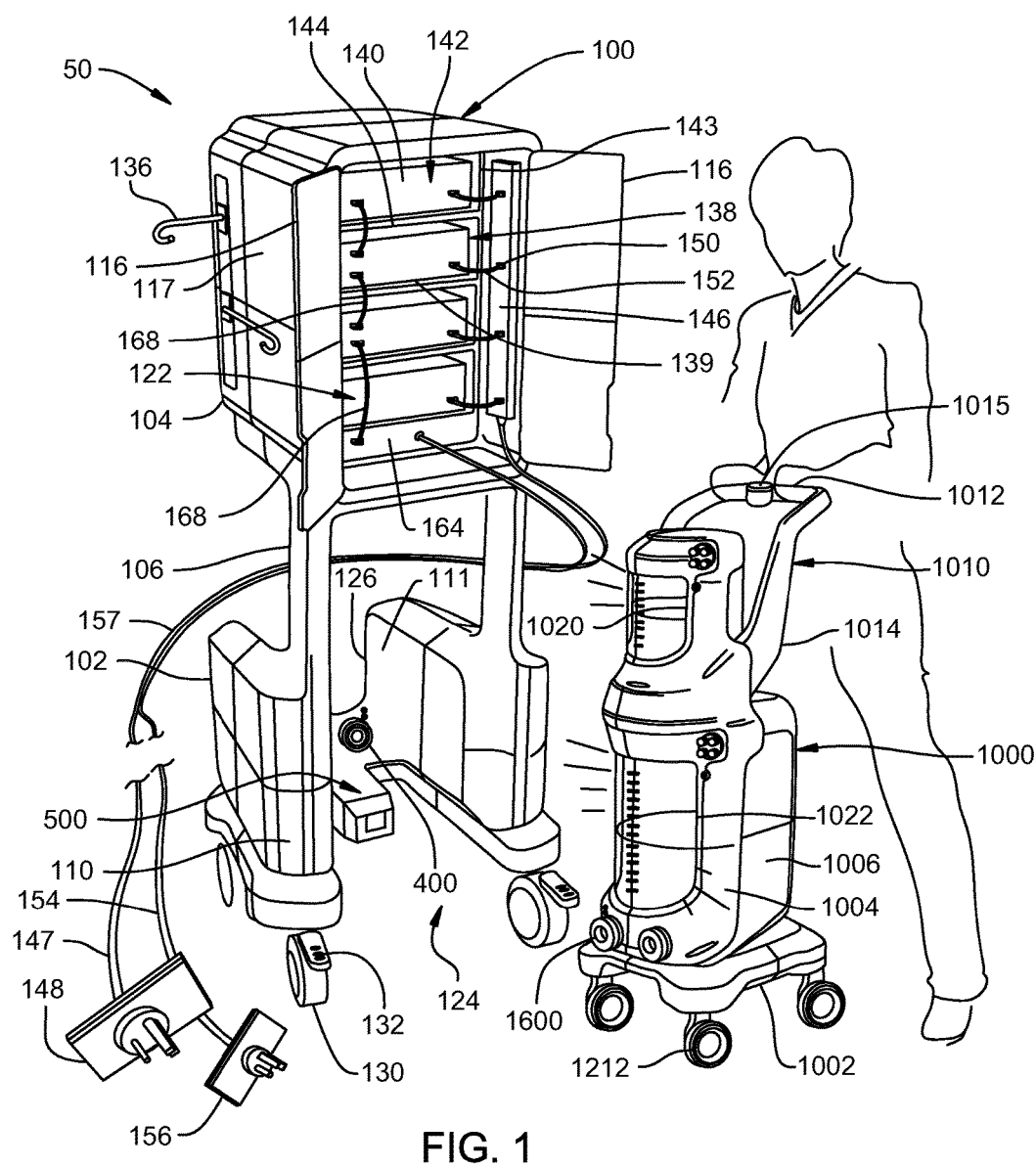
FIG. 1 is a rear perspective view of a medical/surgical waste collection system of this invention showing the mobile rover separated from the mobile chassis in accordance with one embodiment.

Turning to FIGS. 1 and 2, mobile chassis 100 of the first embodiment of this invention is illustrated. Mobile chassis 100 comprises a generally rectangular lower chassis 102 and a generally rectangular upper chassis 104. Upper chassis 104 is supported above lower chassis 102 by a pair of spaced apart supports 106. Lower chassis 102 has outer covers 107 and 108. Outer cover 108 includes a U-shaped front panel 109, rear panels 110, inner panels 111 and outer panels 112. Upper chassis 104 has an outer cover 114 that includes a front panel 115, a pair of rear doors 116, side panels 117, 118, top panel 119 and bottom panel 120. Front panel 115 has several rectangular shaped openings 121. An interior cavity 122 is defined within upper chassis 104.

Covers 107, 108, 114 and doors 116 can be formed from injection molded plastic or other suitable materials and are attached to lower chassis 102 and upper chassis 104 by suitable methods such as through the use of fasteners. Covers 107, 108, 114 and doors 116 are used to protect the internal components of mobile chassis 100 and to provide improved visual aesthetics. Doors 116 provide access to component rack 138 at the rear of mobile chassis 100.

A receptacle or void space 124 is defined between inner panels 111 and bottom panel 120. Void space 124 receives mobile rover 1000 when mobile rover 1000 is mated to mobile chassis 100. A U-shaped cutout 126 is located in panels 109 and 111 so mobile rover container 1202 is visible to medical personnel. A power coupler 500 extends away from front panel 109 into opening 124. Power coupler 500 provides electrical power to mobile rover 1000.

Wheels 130 are attached to lower chassis 102 below cover 107. Wheels 130 allow mobile chassis 100 to be transported and to be easily moved within an operating room/surgical area. Wheels 130 include a braking mechanism 132 that locks wheels 130 in a static position. Braking mechanism 132 allows mobile chassis 100 to be selectively put in an immobilized position within the operating room.

Two spaced apart handles 134 are positioned on opposite sides of upper chassis 104 and extend in a distal direction perpendicularly away from front panel 115. Handles 134 allow medical personnel to grasp and move mobile chassis 100. A pair of pivotable wire/hose support rods 136 with U-hooks extend away from side panel 117. Rods 136 are rotatable toward and away from side panel 117. Rods 136 allow medical personnel to position wires and hoses (not shown) connected to mobile chassis 100 in a bundled and unobtrusive position. Rods 136 also may be used to hold bags of IV fluid, irrigant, or distending solution.

Upper chassis 104 includes a component rack 138. Component rack 138 holds a variety of medical/surgical instruments, instrument consoles or modules 140. For example, component rack 138 can contain equipment, instrument consoles or modules such as an irrigation pump console, an insufflator module, a fiber optic light module or any other suitable surgical instrument or module. Rack 138 has several rectangular shaped compartments 142 that are formed by elongated side rails 143 and cross rails 144. Compartments 142 extend through rack 138 between front openings 121 and rear openings 139. Modules 140 can be slid into compartments 142 when doors 116 are in an open position as shown in FIG. 1. After modules 140 are mounted in rack 138, the front face of the modules 140 are visible through openings 121.

Upper chassis 104 further includes a power strip 146 through which power is supplied to modules 140. Power strip 146 is mounted to rack 138 in cavity 122. Power strip 146 is connected to an external source of power through power cord 147 and power plug 148. Power strip 146 has several connectors 150 that are connected with wires 152 to supply power to modules 140. Another power cord 154 and power plug 156 supply power to other components of mobile chassis 100. Power cords 147 and 154 are bundled together for a portion of their length by a sheath 157 for easier handling and less clutter. Multiple power plugs 148 and 156 are used to reduce potential excess current loads on electrical circuits in the medical facility. The chassis controller 802 (FIG. 23) can ensure both plugs 148,156 are attached to different circuits by imposing a high frequency voltage signal on one of the plugs and monitoring the strength of the signal conducted to the other plug.

Upper chassis 104 has a display assembly or control panel 162 mounted to front panel 115 and a control module 164 that contains electronic components such as a controller or micro-processor for controlling the operation of chassis 100 and coordinating the operation of surgical modules 140 with each other and chassis 100. Power cord 154 supplies power to mobile chassis 100 components other than surgical modules 140. Surgical modules 140 communicate with each other through cables that make up a bus 168. Surgical modules 140 are in electrical communication with each other and with control panel 162 through bus 168. In some versions of the invention, the modules communicate with each other using the IEEE 1394a Firewire System Architecture. The specific means by which the modules communicate with each other is not part of the present invention. Combining the equipment rack 138 with the chassis 100 reduces the overall footprint occupied in the operating room. This creates additional valuable space around the surgical table and reduces clutter. Locating medical equipment in the same location as the chassis 100 simplifies the routing of tubes and wires. The equipment rack 138 reduces the number of power cords going to the wall, thereby eliminating trip hazards and making the positioning of other wheeled equipment easier in the operating room.

Figure 5:
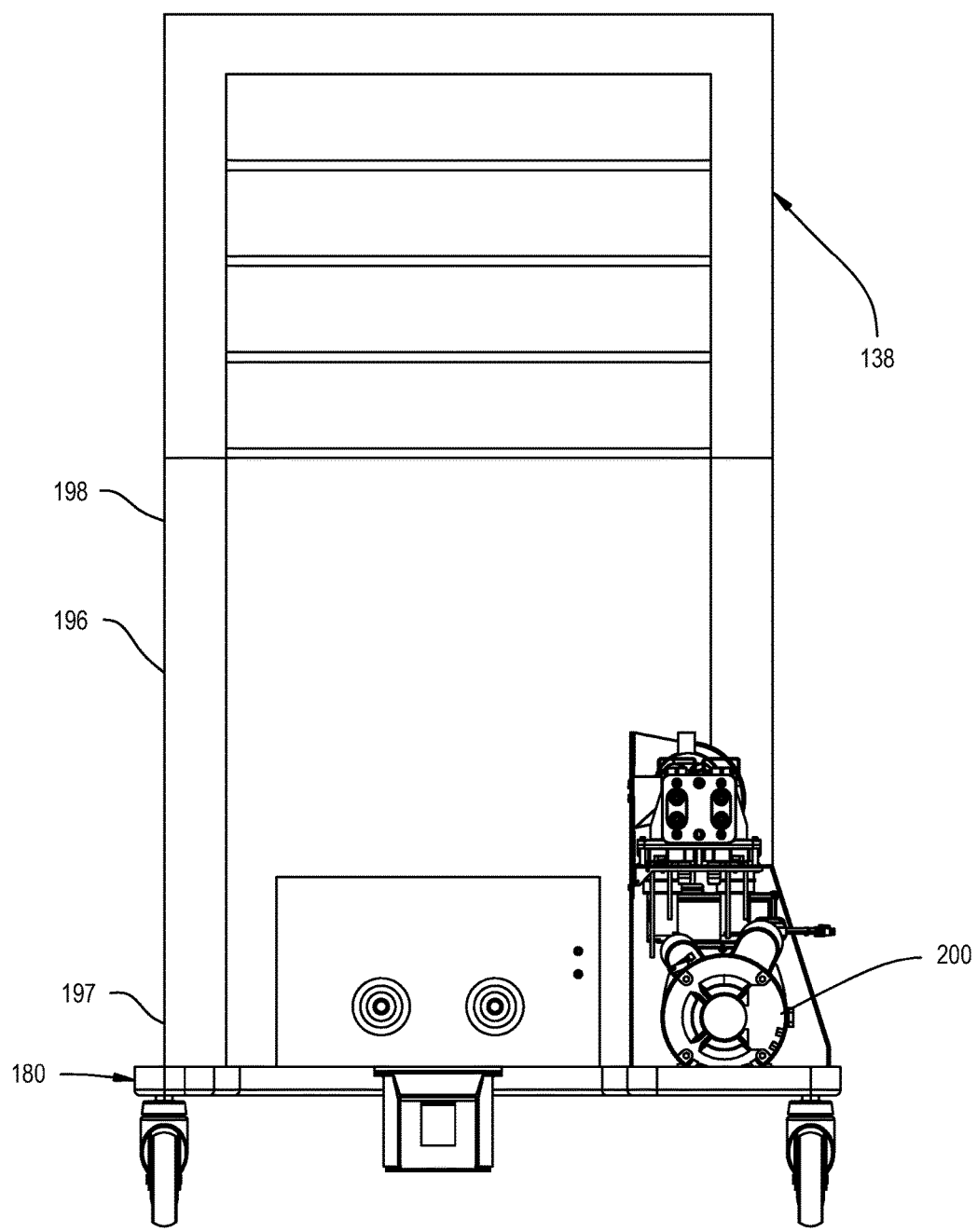
FIG. 5 is a rear perspective view of the mobile chassis with the covers removed.

With reference to FIG. 5, further details of upper chassis 104 are illustrated. The covers 107, 108 and 114 that normally conceal the components of lower chassis 102 and upper chassis 104 are not present in FIG. 5 so that the internal components can be seen. Rack 138 is supported above frame 180 by a pair of spaced apart parallel elongated support posts 196 that have ends 197 and 198. Ends 197 are affixed to frame 180. Support posts 196 extend perpendicularly upward away from frame 180. Rack 138 is affixed to ends 198. Support posts 196 can be formed from any suitable material such as steel and are mounted to frame 180 and rack 138 by suitable methods such as welding or through the use of fasteners.

Figure 6:
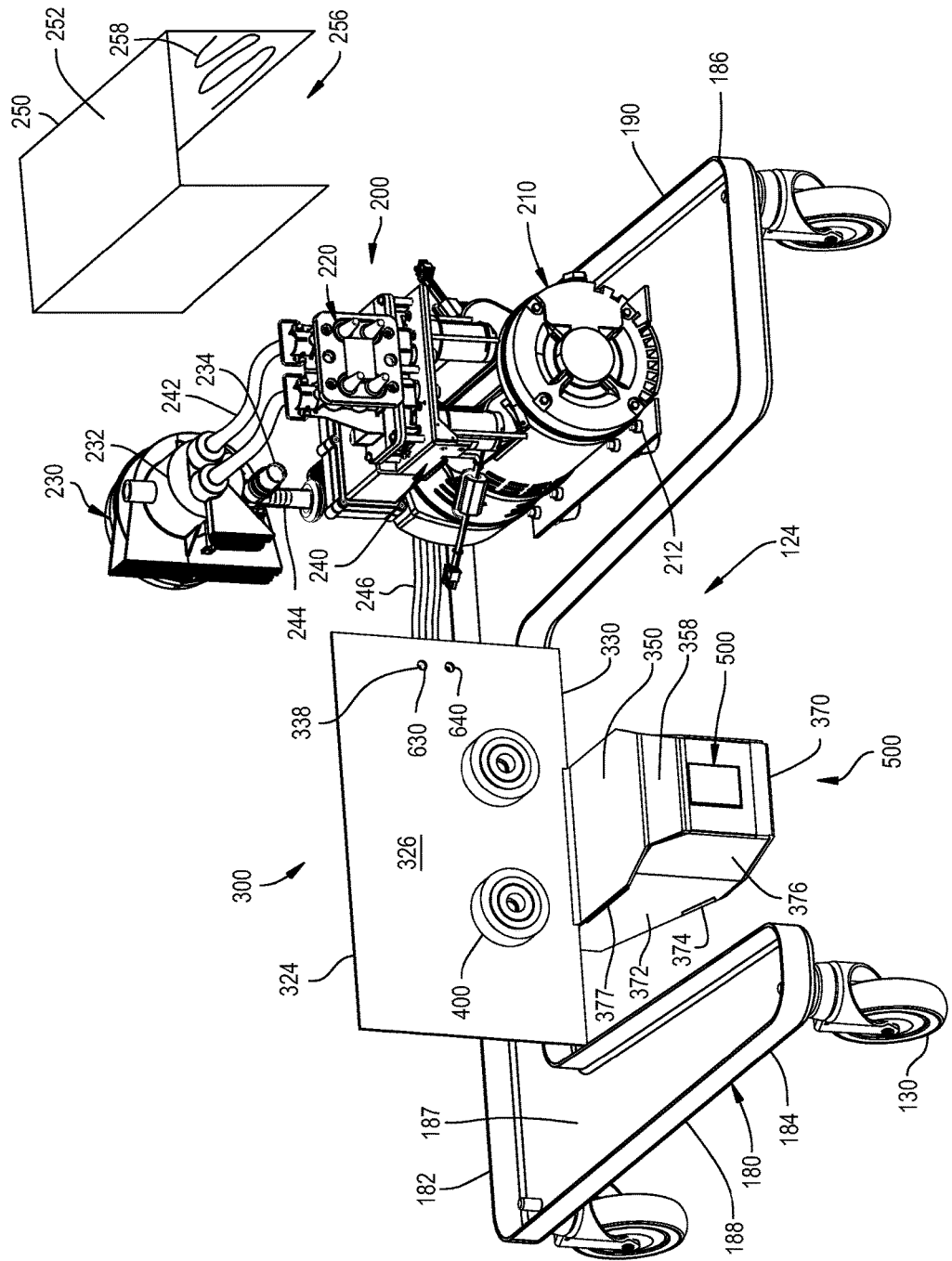
FIG. 6 is a rear perspective view of the mobile chassis with the upper frame and covers removed.

Turning to FIG. 6, further details of lower chassis 102 are illustrated. The upper chassis 104, supports 106, posts 196 and covers 107 and 108 that normally conceal the components of lower chassis 102 are not present in FIG. 6 so that the internal components of mobile chassis 100 can be seen. Lower chassis 102 comprises a generally planar U-shaped frame 180. Frame 180 has a central portion 182 and a pair of arms 184 and 186 that extend generally perpendicularly away in a proximal direction from central portion 182. Arms 184 and 186 are approximately the same length; however, arm 186 is wider than arm 184. Arms 184 and 186 are angled such that the distance between arms 184 and 186 is greater at the proximal ends of arms 184 and 186 than it is adjacent to central portion 182. The angling of arms 184 helps to guide mobile rover 1000 into opening 124 when mobile rover 1000 is mated with mobile chassis 100.

Frame 180 has an upper surface 187, a lower surface 188 and a peripheral rim 190 that encircles the outer periphery of frame 180 and extends perpendicularly upwards. Central portion 182 and arms 184, 186 define a portion of void space 124 there between. Frame 180 can be formed from any suitable material such as stamped sheet steel. Four wheels 130 are attached to the bottom of frame 180 towards the four corners and allow rolling movement of chassis 100.

A vacuum pump and filter assembly 200 for providing a vacuum source and filtering is mounted to frame 180. Vacuum pump and filter assembly 200 comprises a vacuum source or pump 210, vacuum regulator assembly 220 and filter assembly 230. Specifically, vacuum pump 210 is mounted to the upper surface 187 of arm 186 toward the center of arm 186 using fasteners 212. In one embodiment, vacuum source 210 is a rotary vane type vacuum pump. One such vacuum pump is a Gast 1023 Series 12 CFM rotary vane vacuum pump, Part No. 1023-318Q-G274AX, available from Gast Manufacturing, Incorporated, a unit of IDEX Corporation of Northbrook, Ill.

A support structure 240 is mounted to vacuum pump 210 using fasteners (not shown). Vacuum regulator assembly 220 and filter assembly 230 are mounted to support structure 240 using fasteners (not shown). Vacuum regulator assembly 220 integrates vacuum regulators 222, 224 (FIG. 3) and check valves 226, 228 (FIG. 3) into a single unit. Filter assembly 230 integrates HEPA filter 232 and vacuum relief valve 234 into a single unit. Additional details of features of vacuum manifold 220 and filter assembly 230 are disclosed in U.S. Pat. No. 7,621,898, issued Nov. 24, 2009, the contents of which are incorporated herein by reference. A pair of vacuum hoses 242 are connected between vacuum regulator assembly 220 and filter assembly 230. Another vacuum hose 244 connects vacuum pump 210 to filter assembly 230.

An insulating shell 250 encloses vacuum and filter assembly 200. Insulating shell 250 attenuates noise generated by the vacuum components including vacuum pump 210. Insulating shell 250 is generally rectangular in shape and includes five panels 252. Panels 252 define an internal chamber 256 therein. The interior walls of insulating shell 250 are covered with sound deadening insulation 258. Insulating shell 250 is formed from sheet metal, cast metal, plastic, or other suitable material. Insulating shell 250 is mounted over vacuum and filter assembly 200 and is fastened to the frame 180 by fasteners (not shown).

Figure 7:
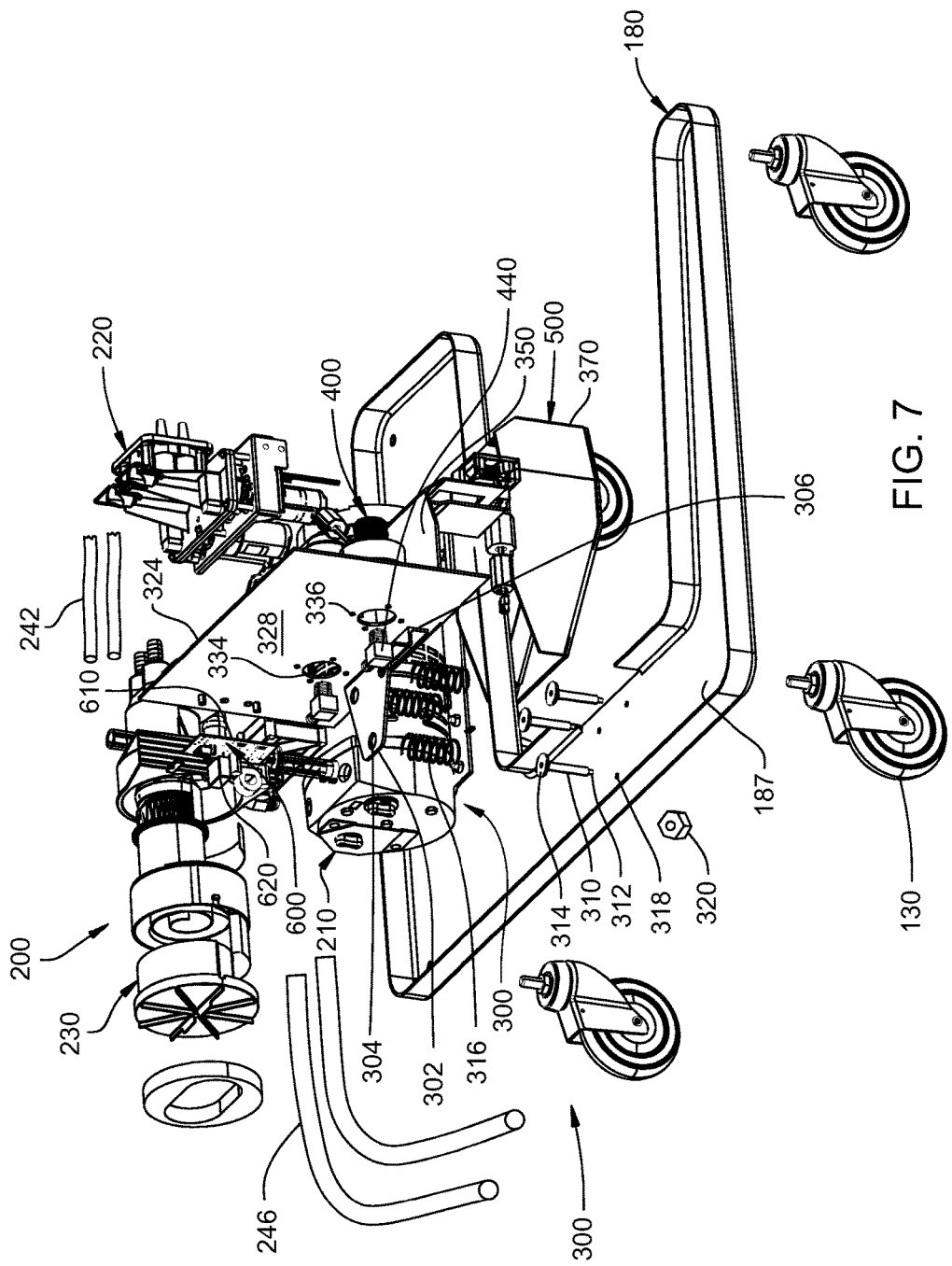
FIG. 7 is a front perspective exploded view of the mobile chassis with the upper frame and covers removed.

With additional reference to FIG. 7, mobile chassis (suction cart) 100 includes a floating cart coupling feature or floating coupler 300. Floating coupler 300 provides six degrees of freedom for the below described chassis vacuum coupler 400 and a chassis power coupler 500 to move relative to chassis frame 180. As described below, this movement facilitates electrical and suction coupling of the mobile rover 1000 to the mobile chassis 100. The flexibility provided by this floating coupler automatically aligns the rover and chassis portions of the mating components even in situations where the OR floor is unlevel or not flat. This allows for rapid mating of the rover to the chassis without the user touching dirty or potentially contaminated vacuum couplings, speeding surgical setup.

Floating coupler 300 includes a trapezoidal shaped bracket 302 that has a bent flange 306 extending from one end. Three apertures 304 extend through bracket 302. Support posts 310 have a threaded end 312 and an opposite end with a disc shaped head 314. Three coils springs 316 are compressed between bracket 302 and upper surface 187 of frame 180. Specifically, supports posts 310 extend through apertures 304 and are surrounded by coil springs 316. Threaded ends 312 extend through holes 318 in frame surface 187. Nuts 320 secure threaded ends 312 to retain supports posts 310 to the chassis frame 180.

Springs 316 are longer in length than posts 310. Bracket apertures 304 are larger in diameter than the outer diameter of the posts 310 and smaller in diameter than post heads 314. The springs 316 extend from frame surface 187 over posts 310 and press against the undersurface of coupler bracket 302. Springs 316 thus hold bracket 302 above frame surface 187. The upward motion of the bracket 302 is limited by the abutment of the upper surface of bracket 302 against post heads 314. Given that the bodies of posts 310 are smaller in diameter than the bracket apertures 304, the bracket is able to move both translationally and rotationally in three axes relative to the posts 310 and by extension, frame 180.

A rectangular shaped and vertically oriented wall 324 has a front surface 326 and a rear surface 328. Wall 324 is attached to flange 306 of bracket 302 such that bracket 302 is generally perpendicular to wall 324. Wall 324 is formed from sheet metal and affixed to flange 306 by suitable methods such as welding or using fasteners. A bottom portion 330 of wall 342 extends over rim 190 in a region adjacent to void space 124. A pair of bores 334 are located toward the lower center of the wall 324 and extend therethrough. Each of bores 334 are surrounded by four equidistant apertures 336. Two additional apertures 338 are located toward one side of wall 324.

Figure 8:
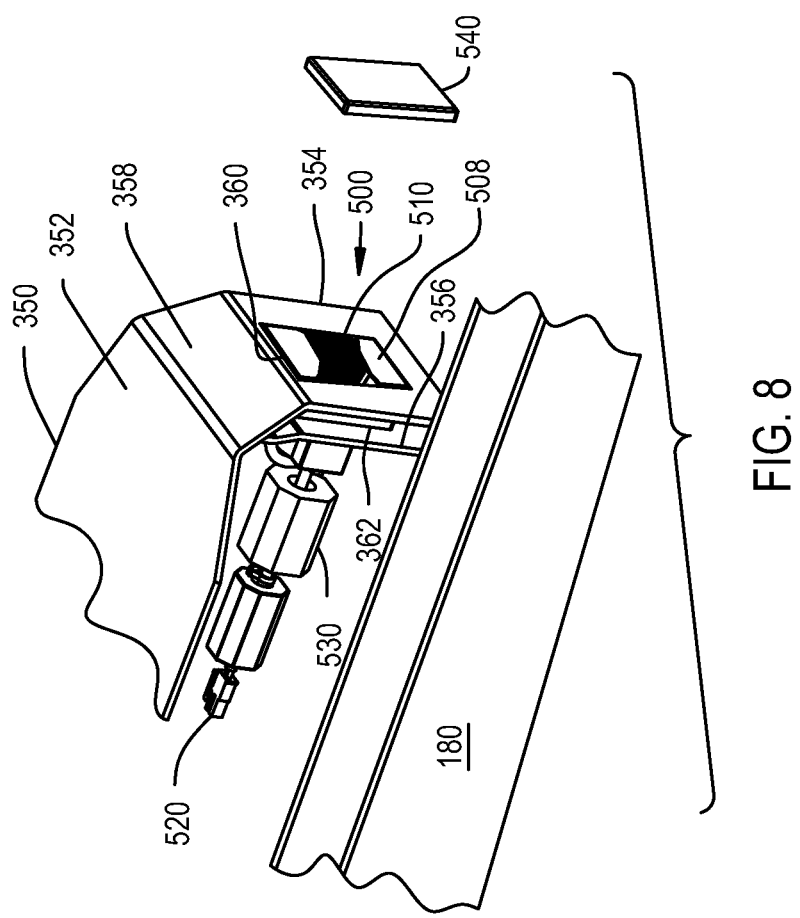
FIG. 8 is an enlarged view of the mobile chassis power coupler.

Another L-shaped bracket 350 is mounted to the front surface 326 of wall 324. Referring to FIG. 8, bracket 350 includes a horizontal plate 352, a first vertical plate 354, a second vertical plate 356 and an angled section 358 located between horizontal plate 352 and the first vertical plate 354. Horizontal plate 352 is generally perpendicular to vertical plates 354 and 356. The first vertical plate 354 and the second vertical plate 356 are parallel and spaced slightly apart from each other. One end of horizontal plate 352 is attached to front surface 326 of wall 324. Horizontal plate 352 is attached to front surface 326 by welding or through the use of fasteners. A first rectangular shaped passage 360 is defined in first vertical plate 354 and a second rectangular shaped passage 362 is defined in second vertical plate 356. Passages 360 and 362 are coaxial with each other.

Turning back to FIGS. 6 and 7, floating coupler 300 further includes a cover or shroud 370. Shroud 370 encloses and protects chassis power coupler 500. Brackets 302, 350, wall 324 and shroud 370 can be formed from sheet metal or plastic materials. Shroud 370 is generally U-shaped and includes upright walls 372, a bottom wall 374 and two angled sections 376. Upright walls 372 are attached to bracket plate 352 by suitable methods such as by fasteners. Angled sections 358 and angled sections 376 assist with centering mobile rover 1000 into mobile chassis 100 when mobile chassis 1000 and mobile rover 100 are mated. Bracket 350 extends slightly beyond walls 372 to define a ridge or lip 377.

Floating coupler 300 allows chassis vacuum coupler 400 and chassis power coupler 500 to rotate and move slightly up, down, sideways and in distal and proximal directions in order to more easily be aligned with corresponding mating features of mobile rover 1000. In particular, coil springs 316 allow brackets 302, wall 324 and shroud 370 to tilt and move slightly in position relative to frame 180. As a result, chassis vacuum coupler 400 and chassis power coupler 500 can move in all directions against the bias of coil springs 316 to facilitate mating with mobile rover 1000.

Figure 9:
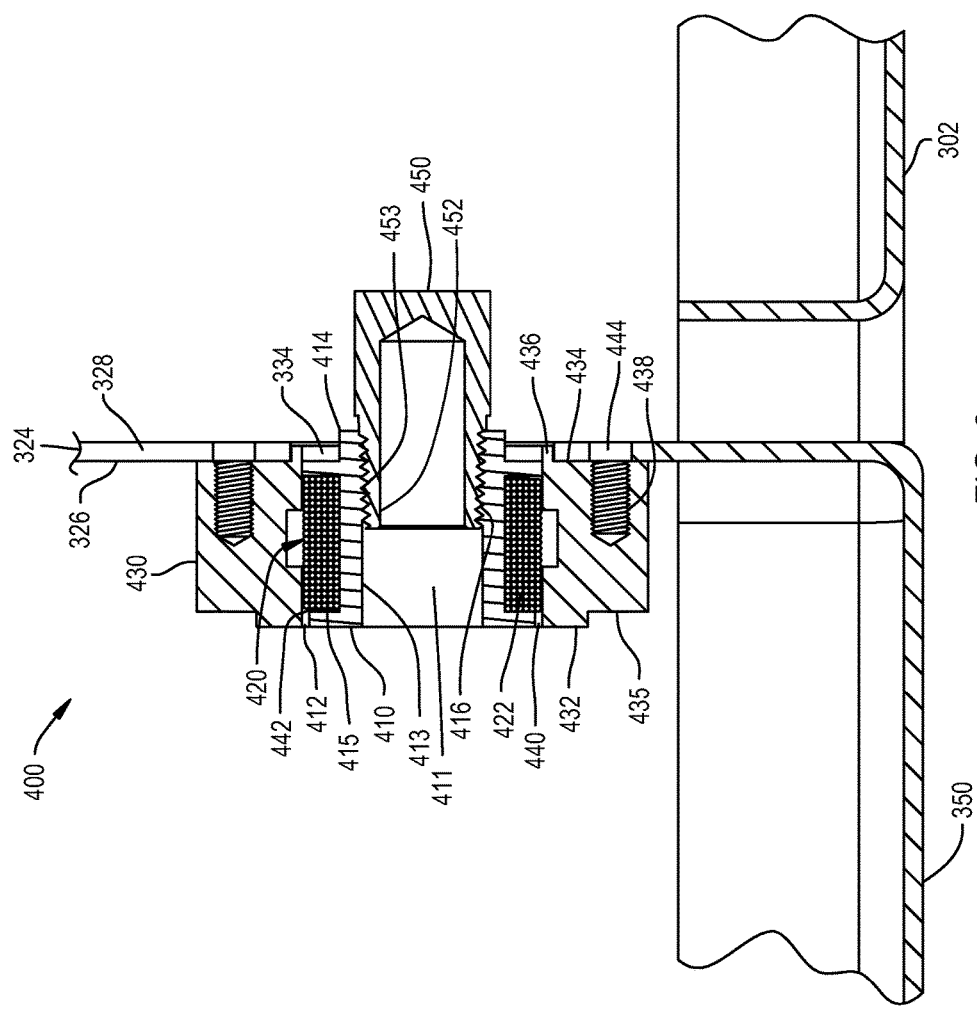
FIG. 9 is a cross-sectional view of the mobile chassis vacuum coupler.

Floating coupler 300 includes two chassis vacuum couplers 400 that are mounted to wall 324. With reference to FIG. 9, each chassis vacuum coupler 400 comprises a chassis inner hub 410, electromagnet 420, chassis outer hub 430 and elbow fittings 450. Inner hub 410 is generally spool-like in shape and has an annular outer surface 412 and an annular inner surface 413 that defines a bore 411. A distal extending boss 414 is located on one side of inner hub 410. Boss 414 fits into wall bore 334. An annular cavity 415 is defined in annular outer surface 412. Wire windings 422 are located in cavity 415 and form electromagnet 420 when electrical power is applied to wire windings 422. While electromagnet 420 is shown as an electro magnet, in one embodiment, electromagnet 420 can be a permanent magnet. Internal threads 416 are formed in the inner surface 413 beginning at the end of boss 414 and extending along inner surface 413 approximately one half the length of bore 411.

Inner hub 410 and outer hub 430 are formed from a ferromagnetic material such as steel such that when electromagnet 420 is energized, inner hub 410 and outer hub 430 produce a magnetic field. Ring shaped outer hub 430 has faces 432 and 434 and an annular step 435. Face 434 is mounted adjacent to and in contact with wall surface 326. Outer hub 430 further includes an annular rim 436 that extends away from face 434 into bore 334. Four threaded bores 438 are defined in face 434. Threaded fasteners 444 are received by threaded bores 438 in order to retain outer hub 430 to wall 324. A bore 440 extends through the center of outer hub 430 between faces 432 and 434 and is defined by an inner surface 442. Annular outer surface 412 and inner surface 442 are tapered such that inner hub 410 is retained by outer hub 430. In another embodiment, inner hub 410 is press fit or connected by an adhesive to outer hub 430.

An elbow fitting 450 is connected to each inner hub 410. Elbow fitting 450 has a threaded end 452 with threads 453 that is mated with inner hub threads 416. The other end of each elbow fitting 450 is connected with vacuum hoses 246 (FIG. 7). Each Vacuum hose 246 extends between elbow fitting 450 and a corresponding fitting on vacuum manifold 220.

Returning to FIG. 8, further details of chassis power coupler 500 are illustrated. Chassis power coupler 500 transfers electrical power via an inductive coupling from chassis 100 to rover 1000. Chassis power coupler 500 includes a ferrite core 508 wound with wire windings 510 both of which are mounted in plate openings 360 and 362. Wire windings 510 are connected to a source of AC power by an electrical cable 520. Electric filters 530 disposed around cable 520 reduce the emission of electrical noise that results from the transmission of electrical signals to the rover. A cover 540 formed from an insulating material covers windings 510. When mobile rover 1000 is mated to mobile chassis 100, power coupler 500 supplies electrical power to mobile rover 1000 through an inductive coupling of winding 510 with another winding in mobile rover 1000. This allows rover components, such as valves, lights, and fluid volume measurement sensors, to be powered without the user making a separate electrical connection manually.

With reference to FIGS. 6 and 7, mobile chassis 100 further includes a chassis data communication module 600. Chassis data communication module 600 facilitates the exchange of data and information between mobile chassis 1000 and mobile rover 100. Chassis data communication module 600 comprises a printed circuit board 610 that contains an electronic communication circuit 620. Electronic communication circuit 620 is sometimes called a signal coupling circuit. Printed circuit board 610 is mounted to the rear surface 328 of wall 324. Communication circuit 620 is connected to an infrared light emitting diode (IRLED) transmitter 630 and receiver 640. IRLED transmitter 630 and receiver 640 are mounted to printed circuit board 610 and extend through wall apertures 338 such that IRLED transmitter 630 and receiver 640 face in a proximal direction. Because IRLED transmitter 630 and receiver 640 are mounted to floating coupler mechanism 300, IRLED transmitter 630 and receiver 640 self-align with a corresponding rover data communication module when rover 1000 is coupled to chassis 100.

B. Mobile Rover

Figure 10:
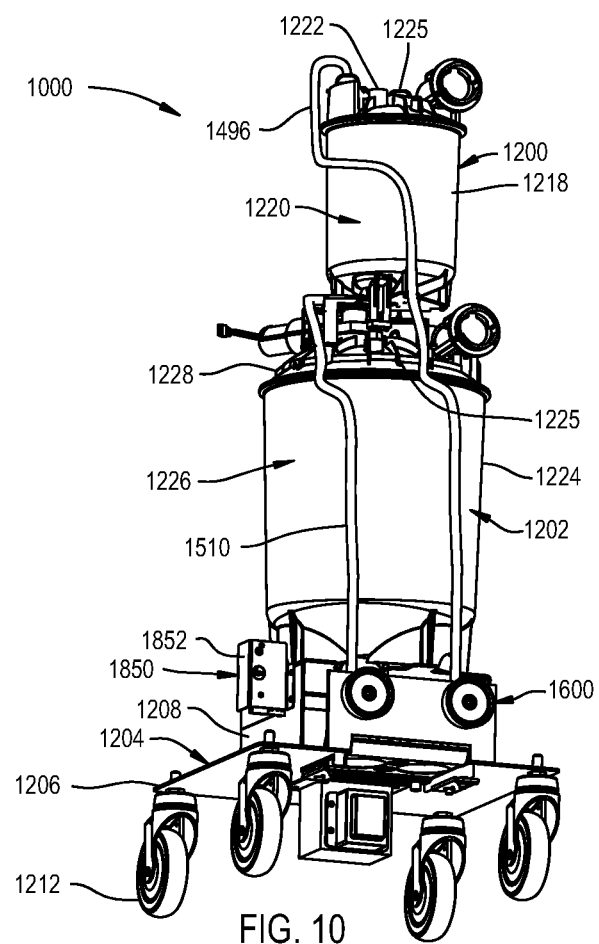
FIG. 10 is a front perspective view of a mobile rover according to one embodiment.

Referring to FIG. 10, waste collection system 50 further includes a mobile rover 1000 that is mated to and disconnected from chassis 100. In FIG. 10, the covers that normally conceal the internal components of mobile rover 1000 are not present to more clearly view the internal components. Mobile rover 1000 includes upper 1200 and lower 1202 waste containers. A frame 1204 supports lower waste container 1202 which in turn supports upper waste container 1200. Upper waste container 1200 is mounted above lower waste container 1202 such that waste material in the upper container 1200 can be emptied into the lower container 1202 using gravity. While two waste containers 1200, 1202 are shown in FIG. 10, in some embodiments, mobile rover 1000 can have only one waste container.

Figure 11:
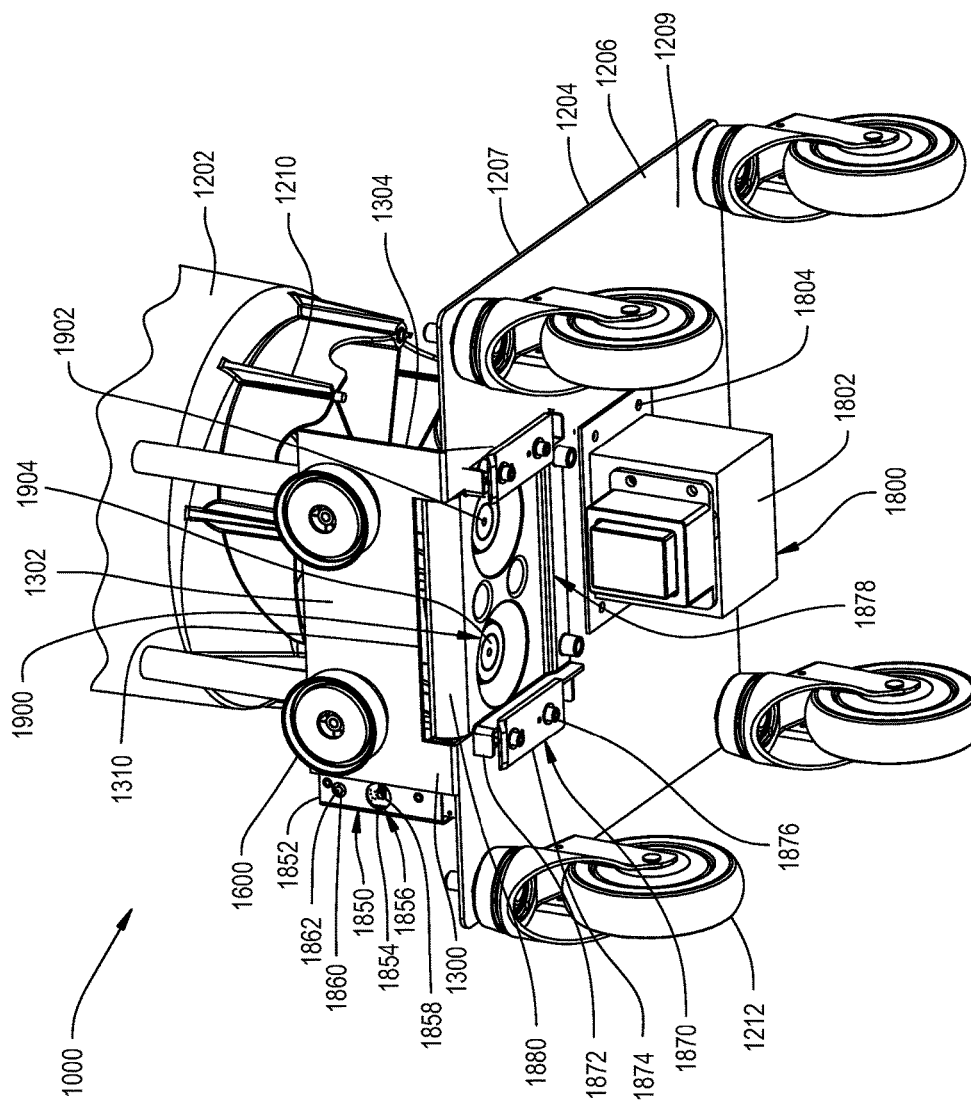
FIG. 11 is an enlarged front perspective view of the bottom section of the mobile rover of FIG. 10.

With additional reference to FIG. 11, frame 1204 comprises a planar rectangular shaped mobile base 1206, a U-shaped support member 1208. The components of frame 1204 can be formed from metals such as steel. Base 1206 includes a top surface 1207 and a bottom surface 1209. Support member 1208 is mounted to the top surface 1207. The lower waste container 1202 has a bottom support ring 1210 that is affixed to support member 1208. Four wheels 1212 are mounted to the bottom of base 1206 to allow rolling movement of the mobile rover 1000.

Returning to FIGS. 1 and 2, the base 1206 is covered by a cover 1002. A front cover 1004 is mounted over the front of waste containers 1200 and 1202 and a rear cover 1006 is mounted over the rear of waste containers 1200 and 1202. Handle 1010 has a grasp bar 1012 and arms 1014 that are attached to frame 1204. An input device such as a release button 1015 is mounted to grasp bar 1012. Button 1015 deactivates electromagnets 420 (FIG. 9) that retains mobile rover 1000 to mobile chassis 100. Medical personnel can use handle 1010 to position mobile rover 1000 by pushing or pulling. Transparent windows 1020 and 1022 are formed in front cover 1002 allowing a user to visually check the contents of waste containers 1200 and 1202.

Covers 1002, 1004, 1006 and handle 1010 are formed from molded plastic and are attached to frame 1204 and waste containers 1200 and 1202 by suitable methods such as through the use of fasteners. Covers 1002, 1004 and 1006 are used to protect the internal components of mobile rover 1000 and to provide improved visual aesthetics.

Referring specifically to FIG. 10, the upper waste container 1200 comprises an upper canister 1218 that is slightly frusto-conical in shape, but appears cylindrical. The upper canister 1218 defines an upper waste chamber 1220 for holding medical/surgical waste. An upper cap 1222 covers the upper canister 1218 enclosing upper waste chamber 1220. The lower waste container 1202 comprises a lower canister 1224 that is also slightly frusto-conical in shape. The lower canister 1224 defines a lower waste chamber 1226 for holding waste material. A lower cap 1228 covers the lower canister 1224 to enclose the lower waste chamber 1226.

Lower canister 1224 has a relatively large interior volume, between approximately 10 and 40 liters. Upper canister 1218 has a smaller volume, between approximately 1 and 10 liters. While, canisters 1218 and 1224 are shown having a frusto-conical shape, other shapes may be used. Canisters 1218, 1224 and caps 1222, 1228 areformed from molded plastic at least a portion of which is transparent. Structural support and mounting features 1225 are formed on the external surface of upper cap 1222 and lower cap 1228 to provide further rigidity to the caps 1222, 1228, to prevent collapse and to allow other components to be attached to caps 1222 and 1228.

Figure 12:
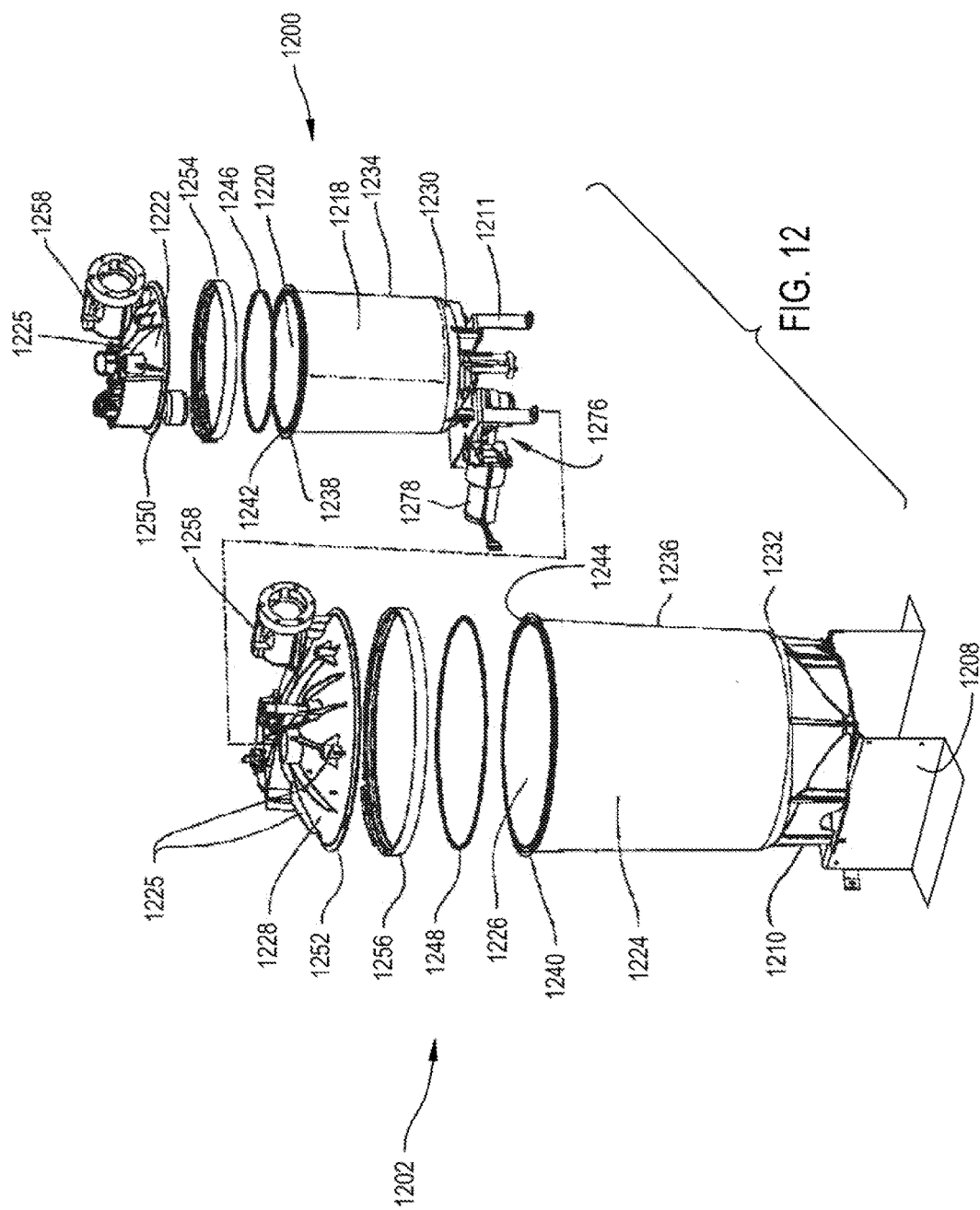
FIG. 12 is an exploded perspective view of the upper and lower waste containers.

With additional reference to FIG. 12, each of the canisters 1218, 1224 includes a bottom 1230 and 1232, respectively. Outer walls 1234 and 1236, respectively, extend upwardly from the bottoms 1230, 1232 to an open end. Annular rims 1238 and 1240, respectively, extend circumferentially around each of the outer walls 1234 and 1236 at the open ends. Grooves 1242, 1244, respectively are defined in rims 1238, 1240. An elastomeric seal 1246, 1248 is disposed in each of the grooves 1242, 1244 to seal the caps 1222, 1228 to the canisters 1218, 1224.

Each of the caps 1222, 1228 is generally dome-shaped with a peripheral lip 1250 and 1252, respectively, that engages the rims 1238, 1240 of the canisters 1218, 1224 with the elastomeric seals 1246, 1248 trapped there between. A V-clamp 1254, 1256, respectively, secures the caps 1222, 1228 to the canisters 1218, 1224 by clamping the peripheral lips 1250, 1252 to the rims 1238, 1240.

Manifold receivers 1258 are mounted to each of the caps 1222, 1228. The manifold receivers 1258 are adapted to receive disposable manifolds 1260 (see FIG. 2), which direct waste material from one or more surgical sites in proximity to a patient, through suction lines 60, 64 (see FIG. 2) into waste containers 1200, 1202. A single suction line 60, 64, respectively is shown attached to each of the disposable manifolds 1260 in FIG. 2. Up to four suction lines can be attached to each disposable manifold 1260. The distal end of suction line 60 is connected to a suction applicator 62 and suction line 64 is connected to a suction applicator 66. Suction applicators 62 and 66 may be built into other surgical tools and instruments that perform additional surgical procedures.

In one embodiment, disposable manifolds 1260 include a filter (not shown) to filter the waste material received from the suction lines 60 and 66 prior to the waste material entering the canisters 1218 and 1224.

The upper canister bottom 1230 is mounted to a support platform 1211 using fasteners (not shown). Support platform 1211 is mounted to lower canister cap 1228. Specifically, support platform 1211 is mounted to mounting features 1225 on lower canister cap 1228 using fasteners (not shown).

Referring now to FIGS. 13 and 14, additional features of caps 1222 and 1228 are shown. In FIGS. 13 and 14, only the upper cap 1222 is shown. The lower cap 1228 has the same features as upper cap 1222, although scaled due to the larger canister size.

Internal to each cap 1222, 1228 is a sprinkler port 1172 that is connected to a sprinkler head 1180. Sprinkler port 1172 and sprinkler head 1180 are connected to a source of water and cleaning fluids for cleaning waste canisters 1218 and 1224.

Internal to each cap 1222, 1228 is a waste conduit or port 1270. Waste conduit 1270 functions as a fluid communications path from the manifold receivers 1258 into respective canister 1218 or 1224 with which the manifold receiver 1258 is associated. The outlet of conduit 1270 directs the flow of incoming air and waste material away from a center axis of the canisters 1218, 1224 toward the outer walls 1234, 1236 of the canisters. By directing air and waste toward canister walls 1234 and 1236, the resulting disturbance of the fluid surface in the canister is minimized, affording a more accurate measurement of contained fluid volume. Forcing the air and waste stream toward the canister walls 1234 and 1236 also promotes the separation of liquid and air. Fluid particles entrained in incoming air are much heavier than the air. While the air is able to change direction as it encounters the canister wall, fluid particles are too heavy to change direction. They impact the canister wall, sticking due to surface tension, and run down into the bottom of the canister.

A vacuum port or conduit 1564 is defined through each of the caps 1222, 1228. Ninety degree elbow joints 1500 are mounted to each of the vacuum ports 1564. Elbow joints 1500 have one end connected to the vacuum ports 1564 and the other end connected to vacuum lines 1496 and 1510 (FIG. 10). Elbow joints 1500 can be press fit into vacuum ports 1564 and into vacuum lines 1496 and 1510. The other end of vacuum lines 1496 and 1510 are connected to rover vacuum coupler 1600 (FIG. 10).

Each of the caps 1222 and 1228 are provided with a filter and float assembly 1562 for preventing water droplets and waste material from entering the vacuum system and vacuum lines 1496, 1510 that could potentially clog the vacuum pump 210.

The vacuum port 1564 of the upper cap 1222 opens into a filter compartment 1566. The filter compartment 1566 is defined by a partitioning wall 1568 that extends downwardly from the bottom of the upper cap 1222. Filter and float assembly 1562 is mounted in filter compartment 1566.

The filter and float assembly 1562 includes a mist trap 1570 disposed in the filter compartment 1566. Any fluids such as air passing into the vacuum port 1564 from within the upper canister 1218 must first pass through the mist trap 1570. The mist trap 1570 is a filter element having a porous structure containing activated carbon material. A retaining member retains the mist trap 1570 within the filter compartment 1566. The retaining member includes a vent plate 1574 defining a plurality of elongated vents 1576 to allow the fluid to pass into the mist trap 1570. The vent plate 1574 includes an upwardly extending sleeve 1578.

Float 1580 is formed of plastic or other lightweight materials and slidably supported on sleeve 1578. Float 1580 includes a balloon-like head 1582 and a neck 1584 extending upwardly from the head 1582 to a tip 1586. The neck 1584 slides in the sleeve 1578. Threads are defined on tip 1586. A stem 1590 has threads at one end to engage the threads on tip 1586. The stem 1590 has a shoulder 1594 that traps a seal member 1596 between the stem 1590 and the tip 1586. The stem 1590 extends to a second end away from the neck 1584 that is slidably supported in a bore defined within the upper cap 1222 at a bottom of the vacuum port 1564.

During use of the waste collection system, should the level of the waste material in the upper canister 1218 exceed a predetermined threshold, the waste material will lift the float 1580 upwardly and drive the second end of the stem 1590 into the vacuum port 1564. Eventually, shoulder 1594 will abut the upper cap 1222 and prevent further upward movement of the float 1580. At this point, the seal member 1596 covers the vacuum port 1564 and mechanically shuts off suction draw from the vacuum pump 210. Waste fluid is thereby prevented from entering the vacuum port 1564 from the upper canister 1218. The float 1580 provides a back-up shut off valve to prevent waste material from being drawn into vacuum pump 210 should an electronic shut-off fail.

FIG. 12 illustrates a transfer valve 1276 disposed between the upper canister 1218 and the lower canister 1224 to facilitate emptying of the waste material from the upper canister 1218 to the lower canister 1224 via gravity. The transfer valve 1276 can be selectively closed to seal the vacuum path between the waste containers 1200 and 1202 to allow independent vacuum regulation. In the open position, waste material present in the upper canister 1218 drains, under the force of gravity, to the lower canister 1224. In the closed position, waste material is retained in the upper canister 1218. In one embodiment, a low level of vacuum can be drawn by lower canister 1224 to assist with drainage of waste material from upper canister 1218 into lower canister 1224. The transfer valve 1276 can be a ball valve. Transfer valve 1276 allows mobile rover 1000 to hold a larger quantity of waste and be used during several medical procedures before emptying is required.

Transfer valve 1276 is moved by a transfer valve actuator or motor 1278. Transfer valve motor 1278 is coupled to the transfer valve 1276 to move the transfer valve 1276 between an open position in which fluid communication occurs between canisters 1218 and 1224 and a closed position in which fluid communication between canisters 1218 and 1224 is blocked. Transfer valve 1276 and transfer valve motor 1278 are both mounted to support platform 1211. Additional details of transfer valve 1276 and transfer valve motor 1278 are disclosed in the incorporated by reference U.S. Pat. No. 7,621,898.

FIG. 11 illustrates further details of rover vacuum coupling 1600. A planar rectangular shaped mounting plate 1300 extends perpendicularly upwards from top surface 1207 of frame 1204. Mounting plate 1300 is formed from metal and is attached to frame 1204. Mounting plate 1300 includes a distal facing surface 1302 and a proximal facing surface 1304. Two apertures 1306 (see FIG. 16) are defined toward the top of mounting plate 1300 and extend entirely through mounting plate 1300. Another pair of smaller diameter apertures 1308 (see FIG. 16) are diametrically opposed to each other on opposite sides of each apertures 1306. A rectangular shaped recess 1310 is located toward a bottom edge of mounting plate 1300 adjacent to frame 1204. Two rover vacuum couplings 1600 are mounted side by side to mounting plate 1300. Vacuum couplers 1600 face in a distal direction away from mobile rover 1600 and face towards void space 124 (FIG. 1) when mobile rover 1000 is mated with mobile chassis 100.

Figure 15:
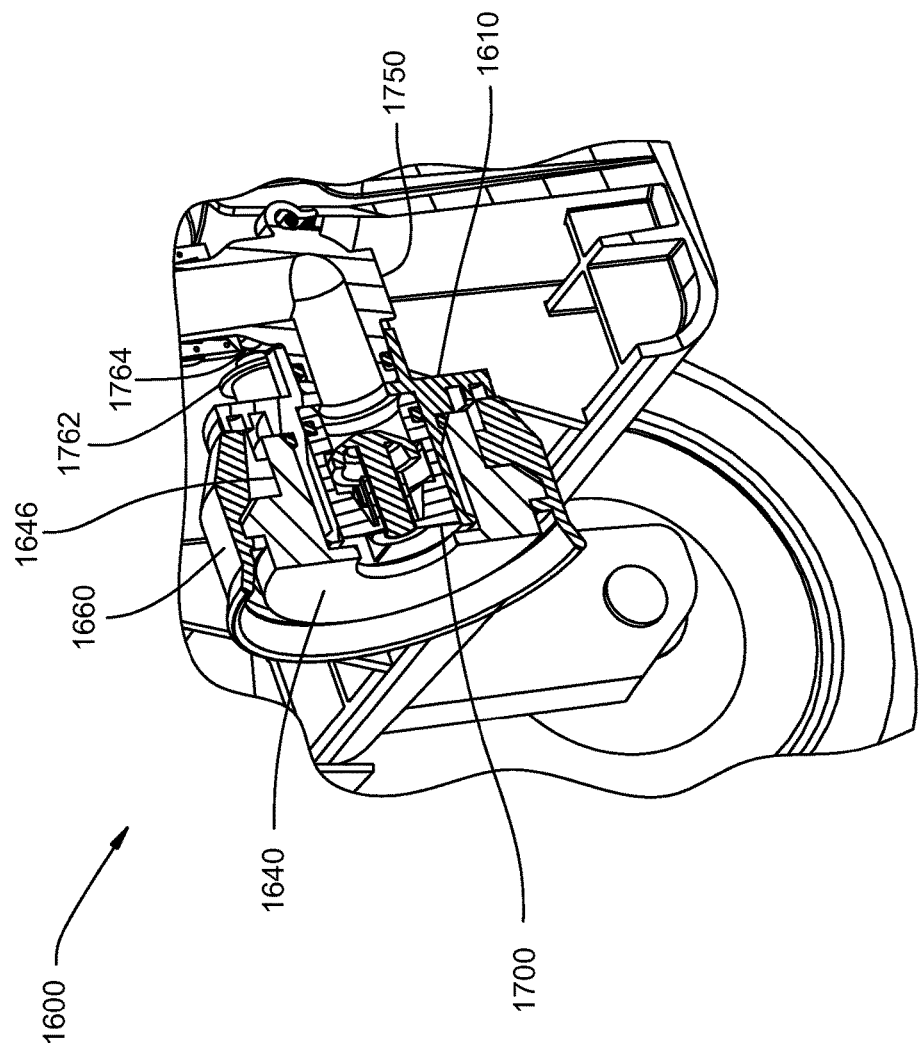
FIG. 15 is an enlarged cross-sectional perspective view of the mobile rover vacuum coupler.
Figure 16:
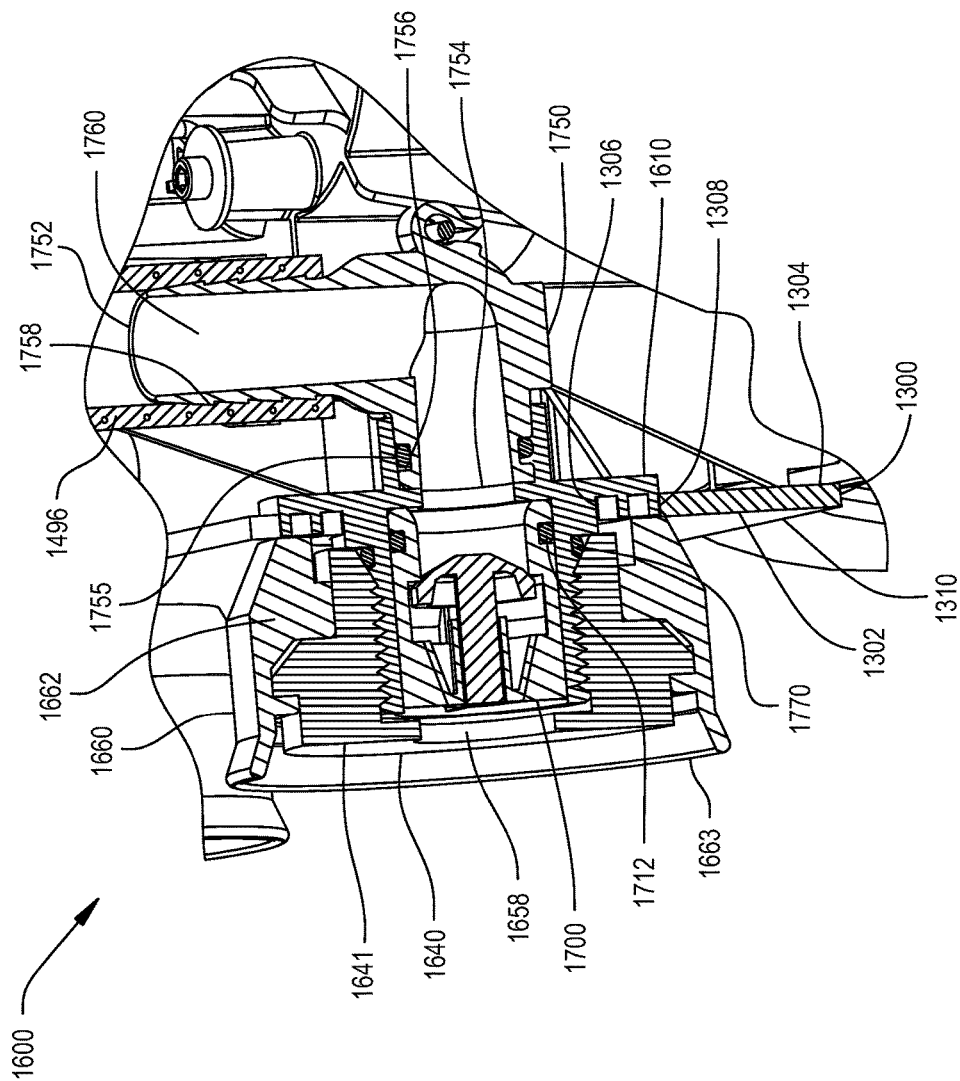
FIG. 16 is an enlarged cross-sectional view of the mobile rover vacuum coupler.

Turning now to FIGS. 15 and 16, cross-sectional views of rover vacuum coupling 1600 are shown. Rover vacuum coupling 1600 comprises a rover inner hub 1610, rover outer hub 1640, face seal 1660, check valve 1700 and elbow fitting 1750. Face seal 1660 surrounds rover outer hub 1640 and rover outer hub 1640 surrounds a portion of rover inner hub 1610. Rover inner hub 1610 contains check valve 1700 therein. Check valve 1700 prevents the flow of suction fluid from mobile chassis 100 into mobile rover 1000 and only allows suction fluid flow to be drawn from mobile rover 1000 into mobile chassis 100. Check valve 1700 further allows rover 1000 to be connected to an alternative suction source such as an external suction source connected through check valves 1280 (FIG. 3). Check valve 1700 also prevents any residual materials that may be present in vacuum coupler 1600 from dripping when mobile rover 1000 is uncoupled from mobile chassis 100.

Figure 17A:
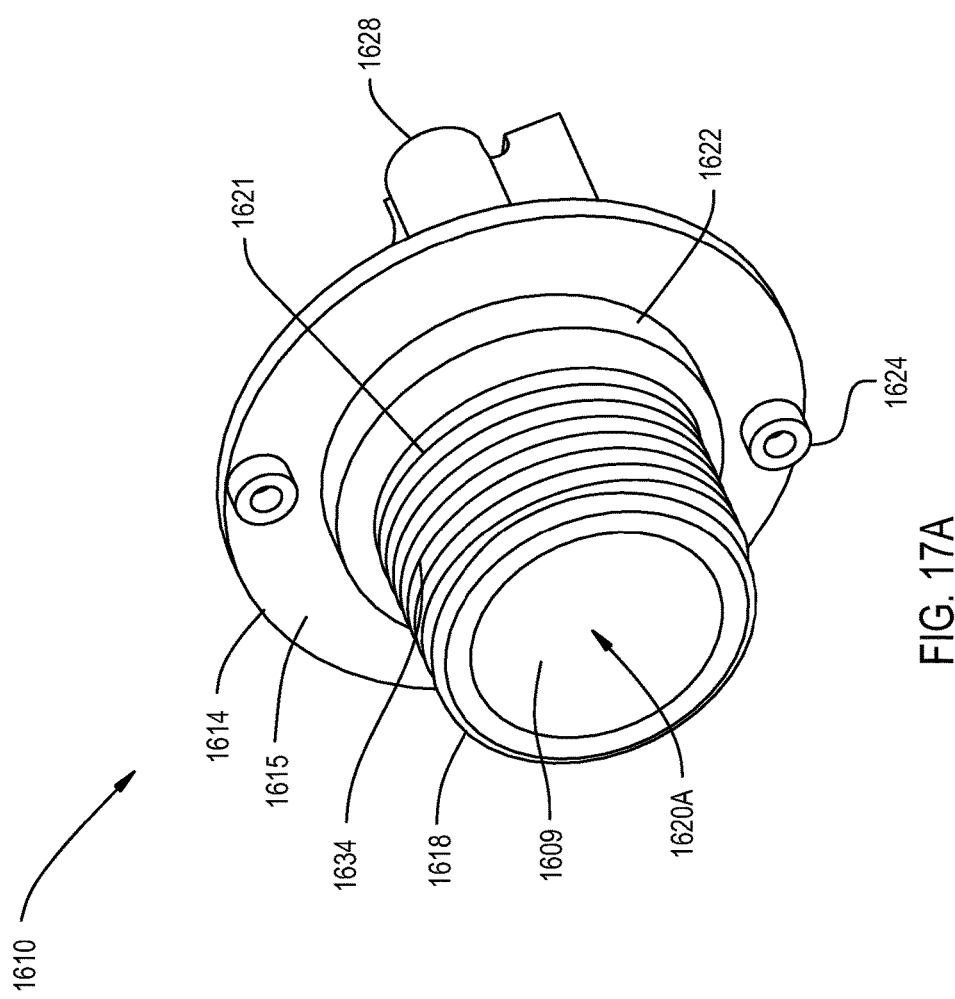
FIG. 17A is a front perspective view of the mobile rover inner hub.
Figure 17B:
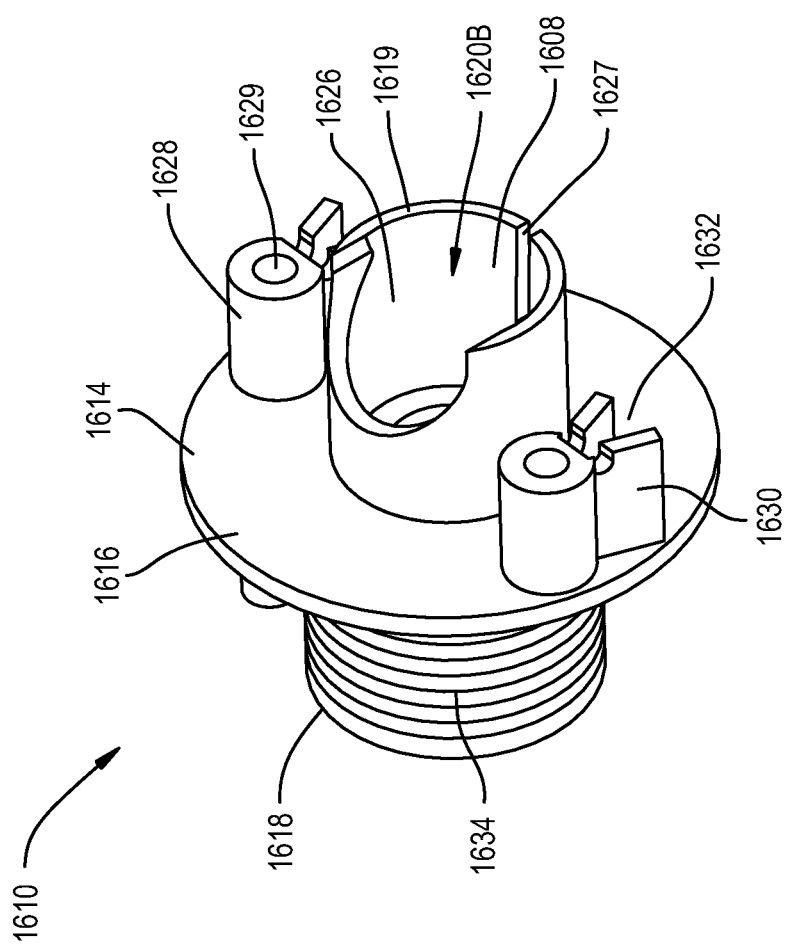
FIG. 17B is a rear perspective view of the mobile rover inner hub.
Figure 17C:
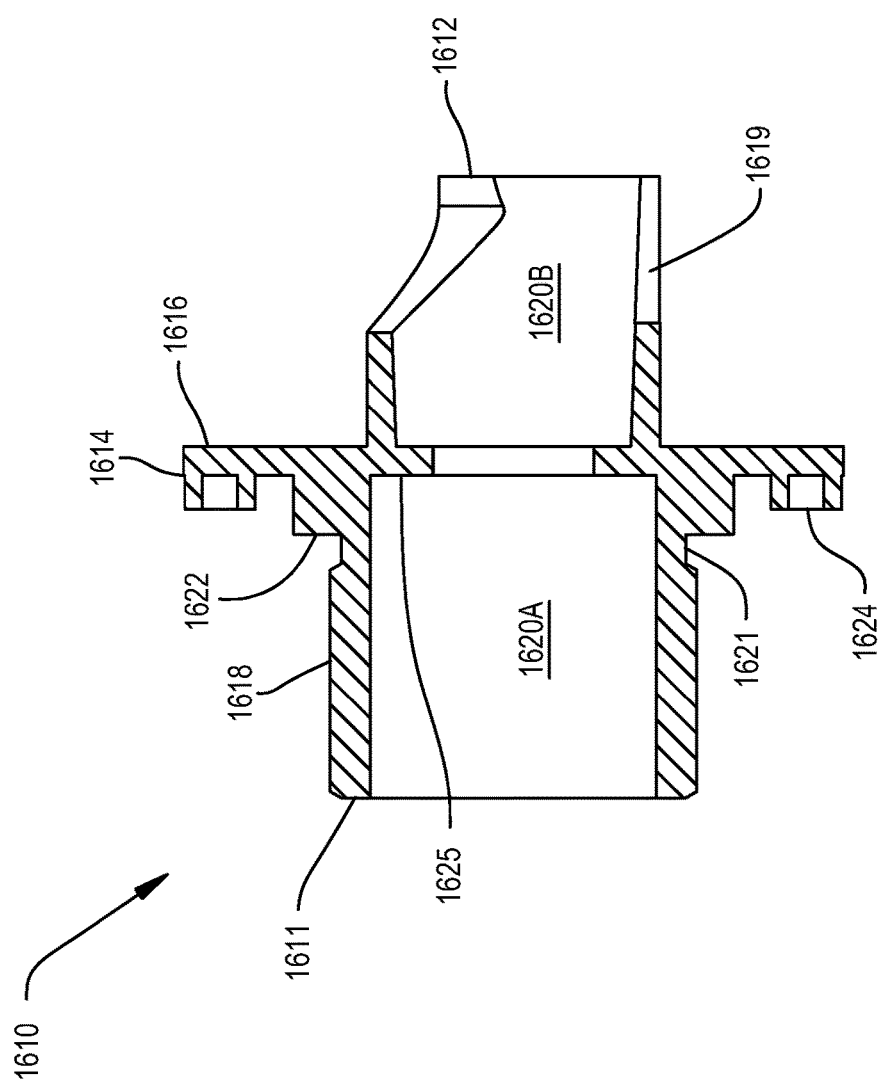
FIG. 17C is a cross-sectional view of the mobile rover inner hub.

FIGS. 17A-C illustrate details of rover inner hub 1610. Rover inner hub 1610 is generally cylindrical in shape with opposing ends 1611 and 1612 and an annular central flange 1614. Central flange 1614 has opposing sides 1615 and 1616. A boss 1618 extends in a distal direction perpendicular to side 1615 and a boss 1619 extends in a proximal direction perpendicular to side 1616. Bore 1620A is defined in boss 1618 by an inner annular surface 1609 and bore 1620B is defined in boss 1619 by an inner annular surface 1608. Bores 1620A and 1620B are co-axial. An annular wall 1625 extends from central flange 1614 partially into and between bores 1620A and 1620B.

An annular step 1622 extends in a distal direction from the base of boss 1618. An annular groove 1621 is defined in the outer surface of boss 1618 adjacent to step 1622. Two diametrically opposed posts 1624 extend perpendicularly from side 1615 on opposite sides of boss 1618.

A portion of boss 1619 is removed to define a cutout 1626. Cutout 1626 receives a portion of elbow fitting 1750. A slot 1627 is defined along the length of boss 1619. Two diametrically opposed posts 1628 extend perpendicularly from side 1616 in a proximal direction on opposite sides of boss 1619. A threaded bore 1629 extends into each post 1628 and a pair of tabs 1630 extends at an angle away from each of posts 1628. Tabs 1630 define an angled slot 1632 there between. External threads 1634 are defined on the outer surface of boss 1618.

Figure 18:
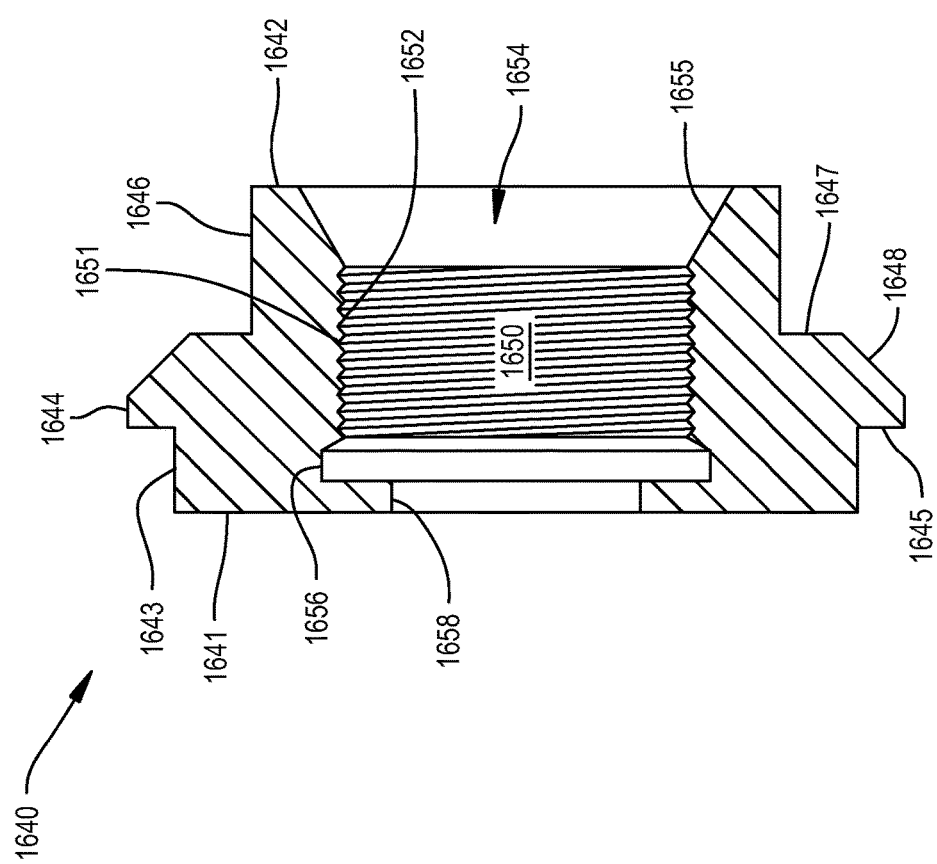
FIG. 18 is a cross-sectional view of the mobile rover outer hub.

With reference to FIG. 18, rover outer hub 1640 is shown. Rover outer hub 1640 is generally cylindrical in shape with a distal directed face 1641 and a proximal directed face 1642. Rover outer hub 1640 has an outer annular surface 1643 adjacent to distal face 1641. An annular flange 1644 extends outwardly from outer annular surface 1643 and defines a step 1645. Another outer annular surface 1646 is adjacent to proximal face 1642. The diameter of outer annular surface 1643 is greater than the diameter of outer annular surface 1646. Another step 1647 is defined between flange 1644 and outer annular surface 1646. An angled face 1648 extends outwardly from step 1647 and faces in a proximal direction.

A central thru bore 1650 extends thru rover outer hub 1640 and is defined by an annular inner surface 1651. Internal threads 1652 are defined in annular inner surface 1651. Outer hub internal threads 1652 mate with inner hub external threads 1634 (FIG. 17A) such that inner hub 1610 and outer hub 1640 are affixed to each other. A counter bore 1654 extends from proximal face 1642 partially into rover outer hub 1640. Counter bore 1654 is defined by a proximal directed partial conical surface 1655. An annular grove 1656 is defined in annular inner surface 1651. An annular lip 1658 extends into bore 1650 adjacent to distal face 1641.

Rover outer hub 1640 is formed from a ferromagnetic material such as steel that is attracted to a magnetic field. Rover inner hub 1610 can be formed from either plastic or metal. Outer hub 1640 is attracted to mobile chassis vacuum coupling 400 when electromagnet 420 (FIG. 9) is energized.

Figure 19:
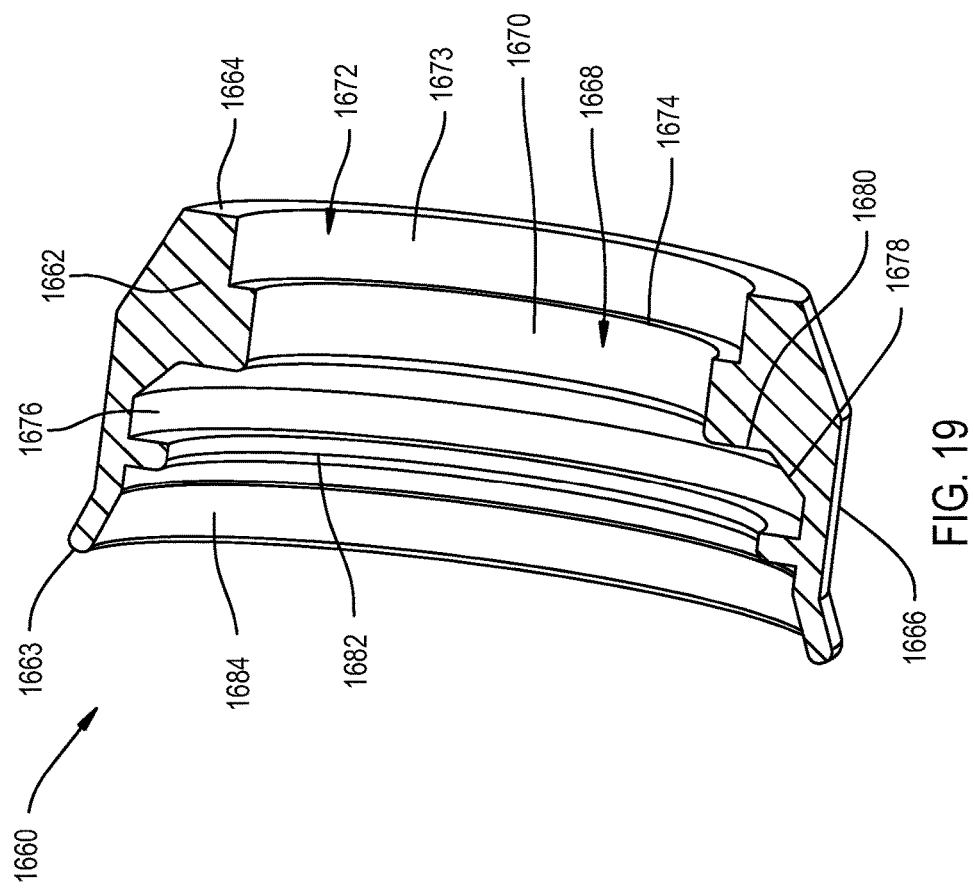
FIG. 19 is a cross-sectional view of the mobile rover face seal.

FIG. 19 illustrates details of face seal 1660. Face seal 1660 is generally cylindrical in shape with a central body 1662, a distal directed flexible annular rim 1663 and a proximal directed face 1664. Face seal 1660 has an outer annular surface 1666 and a central thru bore 1668. Bore 1668 is partially defined by an annular inner surface 1670. A counter bore 1672 extends from proximal face 1664 partially into face seal 1660. Counter bore 1668 is defined by an inner annular surface 1673 that terminates at a step 1674.

An annular grove 1676 is defined in annular inner surface 1670. Annular groove 1676 is further defined by an annular angled surface 1678, an annular step 1680 and an annular lip 1682 that extends into bore 1668. Annular groove 1676 is located toward the center of face seal 1660. Flexible annular rim 1663 has an angled inner surface 1684 that slopes towards the base of annular lip 1682. Face seal 1660 can be formed from a resilient material such as rubber or plastic such that face seal 1660 can be slightly compressed and rim 1663 can flex circumferentially outward and inward.

Figure 20:
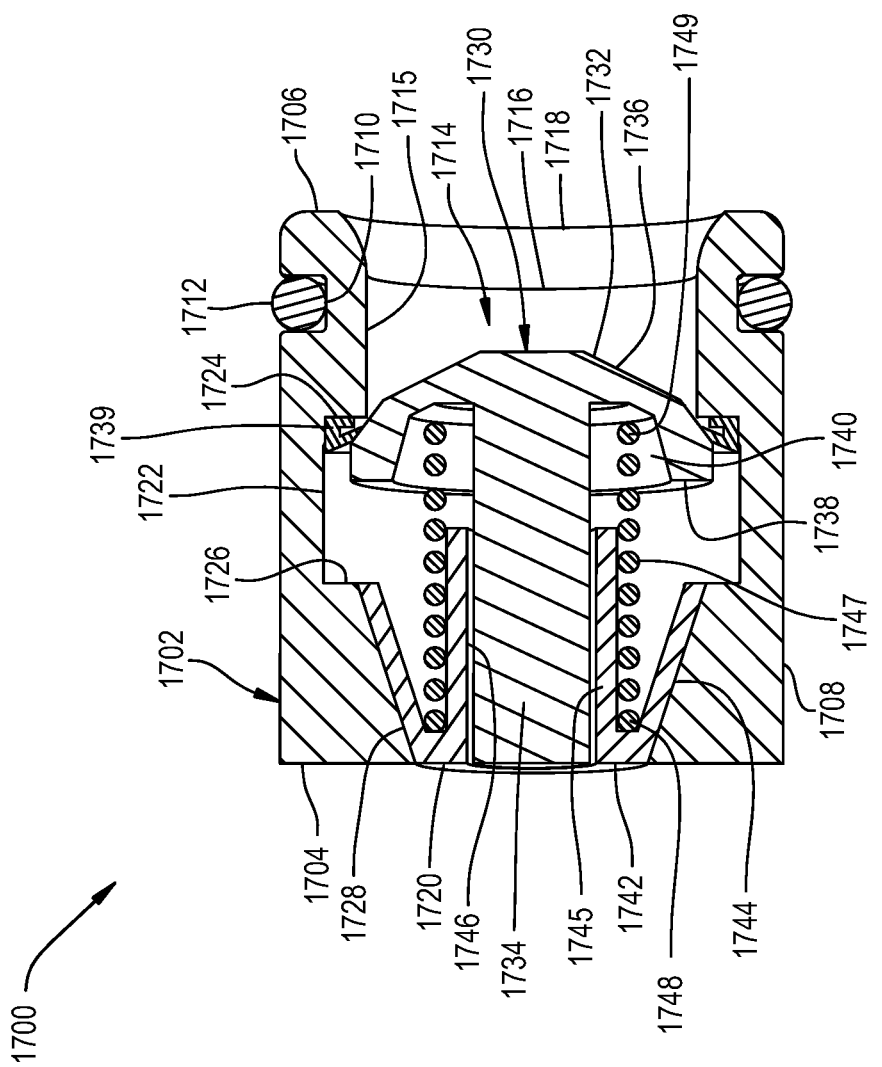
FIG. 20 is a cross-sectional view of the mobile rover check valve.

Referring to FIG. 20, details of check valve 1700 are illustrated. In FIG. 20, check valve 1700 is shown in a closed position blocking suction air flow. Check valve 1700 is generally cylindrical in shape. Check valve 1700 has a cylindrical shaped hollow valve body 1702 that contains a valve head 1730. Valve body 1702 includes a distal directed end 1704 and an opposed proximal directed end 1706. Valve body 1702 has a circumferential outer surface 1708. An annular groove 1710 is defined in outer surface 1708 towards end 1706. A rubber seal 1712 is mounted in annular groove 1710.

Valve body 1702 has a central passage 1714 with an inner surface 1715. An opening 1716 is defined into passage 1714 at end 1706 by a rounded lip 1718 and another opening 1720 is defined into passage 1714 at end 1704. An annular slot 1722 is defined in inner surface 1715 toward the center of valve body 1702. An annular step 1724 is defined between slot 1722 and inner surface 1715 and another annular step 1726 is defined at the other end of slot 1722. A partial conical shaped surface 1728 is defined in valve body 1702 facing passage 1714 and located between step 1726 and distal end 1704.

Valve head 1730 is generally mushroom shaped and has a rounded cap 1732 that is attached to a stem 1734. Cap 1732 has a proximal directed top surface 1736 and a distal directed bottom surface 1738. An annular recess 1740 is defined in bottom surface 1738 surrounding stem 1734. An annular flexible lip seal 1739 is mounted on step 1724. A conical shaped valve member 1742 is mounted in passage 1714 adjacent to opening 1720. Valve member 1742 has a conical shaped wall 1744 and a hollow cylindrical post 1745. Conical shaped wall 1744 rests in contact with conical shaped surface 1728 such that valve member 1742 is prevented from movement in a distal direction. A bore 1746 is defined through the center of post 1745. Bore 1746 receives stem 1734. Post 1745 supports stem 1734 for linear sliding motion of the stem 1734 within the bore 1746.

A coil spring 1747 surrounds the stem 1734 and the post 1745. Coil spring 1747 has a distal end 1748 and a proximal end 1749. Distal end 1748 rests in the junction of the conical wall 1744 and the post 1745. Proximal end 1749 is retained in recess 1740. Coil spring 1747 biases the valve head 1730 into a closed position where a portion of the cap top surface 1736 is seated against and in contact with lip seal 1739. Contact of the cap top surface 1736 with lip seal 1739 causes lip seal 1739 to deflect towards end 1706. When valve head 1730 is in a maximum open position, the movement of valve head 1730 in a distal direction is limited by the engagement of the cap distal bottom surface 1736 with the annular step 1726 and the conical wall 1744.

With reference to FIGS. 16, 17A, 17C and 20, check valve 1700 is mounted in inner hub bore 1620A with check valve outer surface 1708 surrounded by inner hub inner surface 1609 and check valve end 1706 abutting inner hub wall 1625. The seal 1712 is compressed between the bottom of groove 1710 and the inner hub inner surface 1609 in order to form a seal between valve 1700 and inner hub 1610. This seal substantially eliminates loss of vacuum between check valve 1700 and inner hub 1610. Check valve 1700 is further retained in bore 1620A by the outer hub annular lip 1658 extending over a portion of the check valve distal end 1704.

Turning to FIGS. 16, 18 and 19, face seal 1660 is mounted over and surrounds outer hub 1640. Specifically, the outer hub flange 1644 is surrounded by face seal groove 1676 and the outer hub step 1647 abuts face seal step 1680. The flexibility of rubber face seal 1660 allows face seal 1660 to be stretched over outer hub 1640. The face seal lip 1682 is mounted over and abuts the outer hub step 1645. The face seal proximal directed face 1664 abuts and is slightly compressed against mounting plate surface 1302. Central body 1662 is sandwiched and compressed between the mounting plate surface 1302 and the outer hub step proximal face 1647. Because central body 1662 is formed from a resilient material such as rubber, the central body 1662 acts as a spring by flexing and assisting with alignment of the outer hub distal face 1641 when mated to the vacuum coupler 400.

Referring to FIGS. 16, 17A-C and 18, rover inner hub 1610 is mounted to mounting plate 1300. Specifically, inner hub boss 1618 and step 1622 extend through mounting plate bore 1306 with inner hub flange surface 1615 abutting mounting plate proximal surface 1304 and inner hub posts 1624 extending through apertures 1308. Rover inner hub 1610 is mated with and coupled to rover outer hub 1640. Face seal 1660 is mounted to outer hub 1640 and the combination is positioned on the distal side of mounting plate 1300 and rotated or screwed onto inner hub 1610.

In particular, the outer hub threads 1652 are mated with the inner hub threads 1634 to retain inner and outer hubs 1610 and 1640, respectively together. When outer hub 1640 is rotated onto inner hub 1610, face seal proximal directed face 1664 (FIG. 19) abuts and is slightly compressed against mounting plate surface 1302. A seal 1770 is compressed between outer hub angled surface 1655 and inner hub step 1622 to form a vacuum seal between the inner hub 1610 and the outer hub 1640. This seal substantially eliminates loss of vacuum between the inner hub 1610 and the outer hub 1640.

Turning back to FIGS. 16 and 17B, ninety degree elbow fitting 1750 has a barbed end 1752 and another end 1754. An annular groove 1756 is defined in the exterior surface of end 1754 and receives a seal 1755. End 1754 is received by inner hub cutout 1626 and bore 1620B (FIG. 17B). Seal 1755 is compressed between the base of groove 1756 and the inner surface 1608 of inner hub 1610 to form a seal between elbow fitting 1750 and inner hub 1610. This seal substantially eliminates loss of vacuum between the inner hub 1610 and the elbow fitting 1750.

Annular barbs 1758 are defined in the exterior surface of end 1752. An elbow fitting 1750 is coupled to each of vacuum lines 1496 and 1510. Specifically, fitting ends 1750 are connected to each of the vacuum lines 1496 and 1510. Annular barbs 1758 grasp the interior surface of vacuum lines 1496 and 1510. A lumen 1760 is defined through elbow fitting 1750. FIG. 15 illustrates a diametrically opposed pair of mounting features 1762 that are located on each side of fitting 1750. A threaded fastener 1764 such as a screw extends through each of the mounting features 1762, is retained in the threaded bore 1629 (FIG. 17B) and attaches a wire clip 1766 that extends over elbow fitting 1750. In this manner, elbow fitting 1750 is mounted to inner hub 1610.

Figure 21:
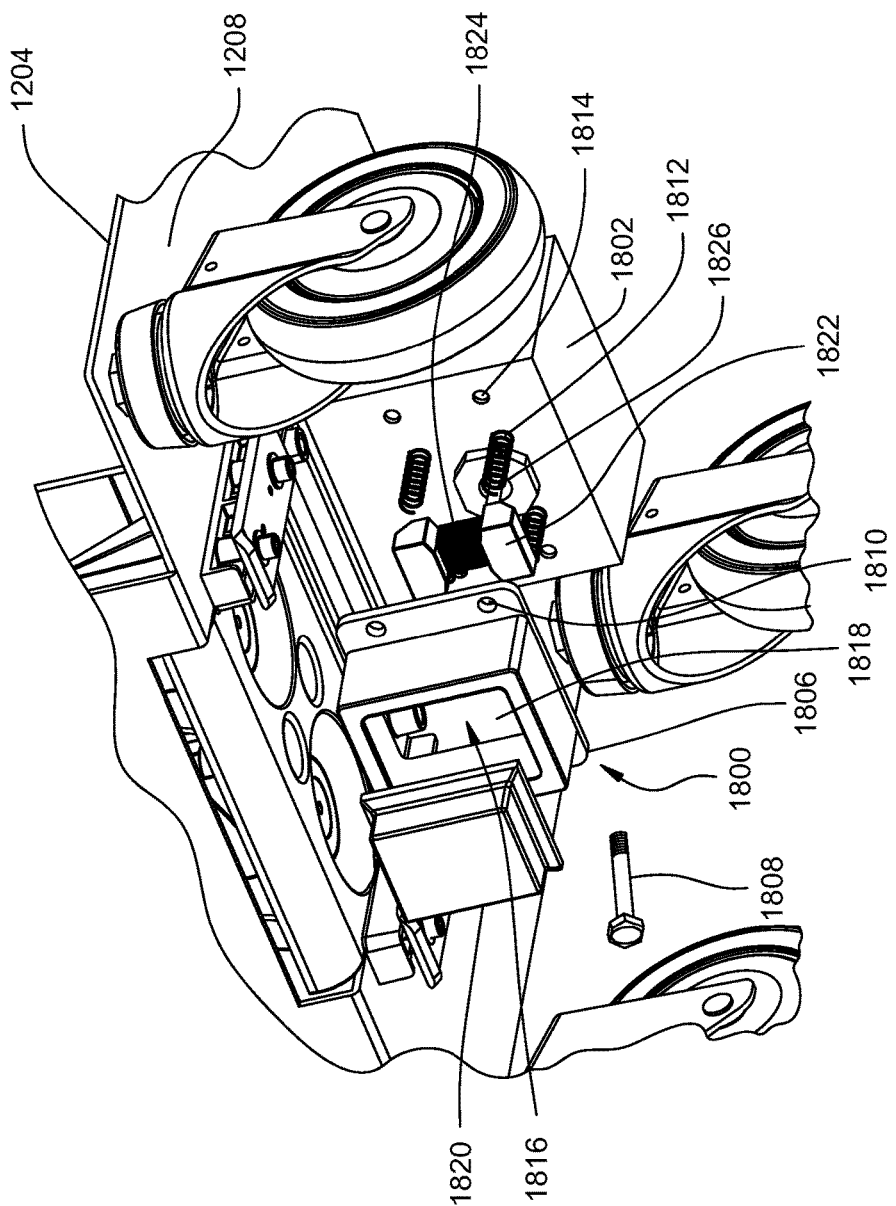
FIG. 21 is an exploded view of the mobile rover power coupler.

A mobile rover power coupler 1800 is shown in FIG. 21. Rover power coupler 1800 receives electrical power from chassis power coupler 500 (FIG. 8). Rover power coupler 1800 receives electrical power via an inductive coupling from mobile chassis power coupler windings 510 (FIG. 8). Rover power coupler 1800 includes a rectangular shaped housing 1802 that is mounted to frame bottom surface 1208 by fasteners 1804 (FIG. 11). A cover 1806 is mounted to the front face of housing 1802 using threaded fasteners 1808 that extend through cover apertures 1810. Cover 1806 is formed from a non-conductive material such as molded plastic. Cover 1806 has a cavity 1816 and a distal facing opening 1818. A front plate 1820 is mounted over opening 1818 and encloses cavity 1816. Front plate 1820 has four outwardly extending shoulders that abut portions of cover 1806 in order to retain plate 1820 within cavity 1816. Four coil springs 1812 are mounted between the distal facing surface of housing 1802 and bores (not shown) in the proximal side of plate 1820. Coil springs 1812 bias front plate 1820 away from housing 1802 such that the plate shoulders are engaged with portions of cover 1806 about opening 1818. A ferrite core 1822 and wire windings 1824 are mounted within cover 1806. Wire windings 1824 are connected to an electrical circuit in mobile rover 1000 by an electrical cable 1826.

Coil springs 1812 allow plate 1820 to float or move within cavity 1816 in order to better align power coupler 1800 with power coupler 500 during mating. When mobile rover 1000 is mated with mobile chassis 100, wire windings 1824 receive inductively coupled electrical power from mobile chassis wire windings 510. This electric power is used by various systems of the mobile rover 1000.

With reference to FIGS. 10 and 11, mobile rover 1000 further includes a rover data communication module 1850. Rover data communication module 1850 facilitates the exchange of data and information between mobile rover 1000 and mobile chassis 100. Rover data communication module 1850 comprises a housing 1852 that contains a printed circuit board 1854 that contains an electronic communication circuit 1856. Communication circuit 1856 is sometimes called a signal coupling circuit. Housing 1852 is attached to support member 1208.

Communication circuit 1856 includes infrared light emitting diode (IRLED) transmitter 1858 and receiver 1860. IRLED transmitter 1858 and receiver 1860 are mounted to printed circuit board 1854 and extend through housing apertures 1862 such that IRLED transmitter 1858 and receiver 1860 face in a distal direction toward mobile chassis data communication module 600 (FIG. 7) when mobile rover 1000 is mated to mobile chassis 100.

As shown in FIGS. 6 and 11, after mobile rover 1000 is mated to mobile chassis 100, rover IRLED transmitter 1858 is juxtaposed to chassis IRLED receiver 640 and rover IRLED receiver 1860 is juxtaposed to chassis transmitter 630. IRLED transmitters 630 and 1858 transmit light signals 631 and IRLED receivers 640 and 1860 receive light signals 631. The IRLED transmitters and receivers allow communication between mobile chassis 100 and mobile rover 1000 using infrared light signals 631.

FIG. 11 illustrates a guide apparatus 1870 that is adapted to guide floating coupler mechanism 300 (FIG. 6) into guide apparatus 1870 when mobile rover 1000 is mated with mobile chassis 100. Guide apparatus 1870 is mounted to the bottom surface 1208 of frame 1204. Guide apparatus 1870 comprises a spaced apart pair of elongated guide rails 1872 and a pair of guide plates 1874. The guide rails 1872 are formed integral with water and drain manifold 1900. Guide plates 1874 are coupled to the integral guide rails 1872 by fasteners 1876 mounted through frame 1204. Fasteners 1876 also attach water and drain manifold 1900 to frame 1204. Guide rails 1872 and guide plates 1874 are located on opposite sides of an opening 1878 in frame 1204. Opening 1878 is located toward a front edge of frame 1204. Guide rails 1872 have rounded ends that extend away from the center axis of frame 1204 and guide plates 1874 have rounded edges. The guide rails 1872 are oriented generally perpendicular to bottom surface 1208 and the guide plates 1872 are mounted perpendicular to guide rails 1872.

Guide apparatus 1870 further includes a rounded distal facing guide shoulder 1880 that extends upwardly from front edge of frame 1204 adjacent opening 1878 and between guide rails 1872.

Guide rails 1872 are formed with an outward facing angle to each other such that the distance between the distal ends of guide rails 1872 adjacent to shoulder 1880 is greater than the distance between the proximal ends of guide rails 1872. Guide plates 1874 are mounted at an angle to the frame bottom surface 1208. The ends of guide plates 1874 toward shoulder 1880 are positioned lower than the other end of guide plates 1874.

A water and drain manifold 1900 is mounted to frame 1204 over opening 1878. Water and drain manifold 1900 includes a waste coupling port or outlet fitting 1902 and a water coupling or port or inlet fitting 1904 that face in a downward direction from manifold 1900 into opening 1878. Waste port 1902 and water port 1904 are connected to static docker 900 (FIG. 4) in order to facilitate the emptying of waste from and cleaning of waste canisters 1218 and 1224 (FIG. 10).

C. Static Docker

Figure 22:
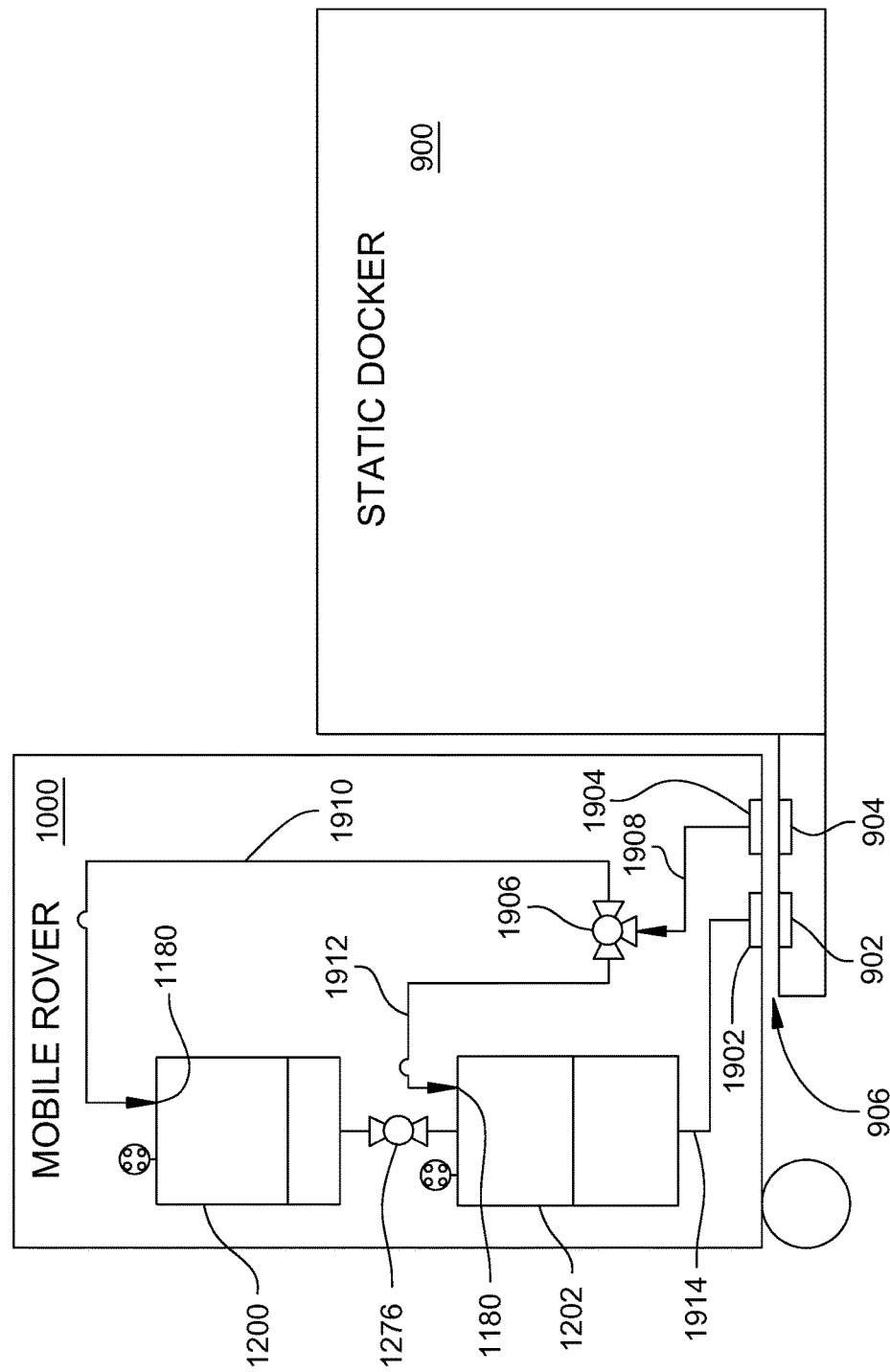
FIG. 22 is a diagrammatic view of the water and drain fluid communication paths according to one embodiment.

With reference to FIG. 22, a water and drainage diagram of mobile rover 1000 docked with static docker 900 is illustrated. Mobile rover 1000 is emptied of accumulated medical/surgical waste and cleaned while docked with static docker 900. Static docker 900 includes waste port 902 and water port 904. Waste port 902 and water port 904 are coupled with respective waste port 1902 and water port 1904 of mobile rover 1000. Static docker waste port 902 and mobile rover waste port 1902 collectively form a complete waste port 906, after docking. Water port 1904 is connected to a diverter valve 1906 through water line 1908. Diverter valve 1906 regulates the flow of water and cleaning fluids to respective waste containers 1200 and 1202. Water line 1910 connects diverter valve 1906 to sprinkler head 1180 in waste container 1200. Water line 1912 connects diverter valve 1906 to sprinkler head 1180 in waste container 1202. Waste port 1902 is connected to the bottom of waste container 1202 by a spout 1914 located in the bottom of container 1202.

After mobile rover 1000 has been docked with the static docker 900, the lower waste container 1202 is emptied of accumulated waste by static docker 900. Transfer valve 1276 is in an open position during the emptying operation such that any waste in upper waste container 1200 flows into lower waste container 1202. After the lower waste container 1202 is empty, the upper waste container 1200 and the lower waste container 1202 are cleaned by cleaning fluids pumped by static docker 900 through water port 1904, water line 1908, diverter valve 1906, respective water lines 1910, 1912, respective sprinkler heads 1180 and into respective waste containers 1200 and 1202. The accumulated cleaning fluids are emptied through spout 1914 and waste port 1902.

D. Power and Control System

Figure 23:
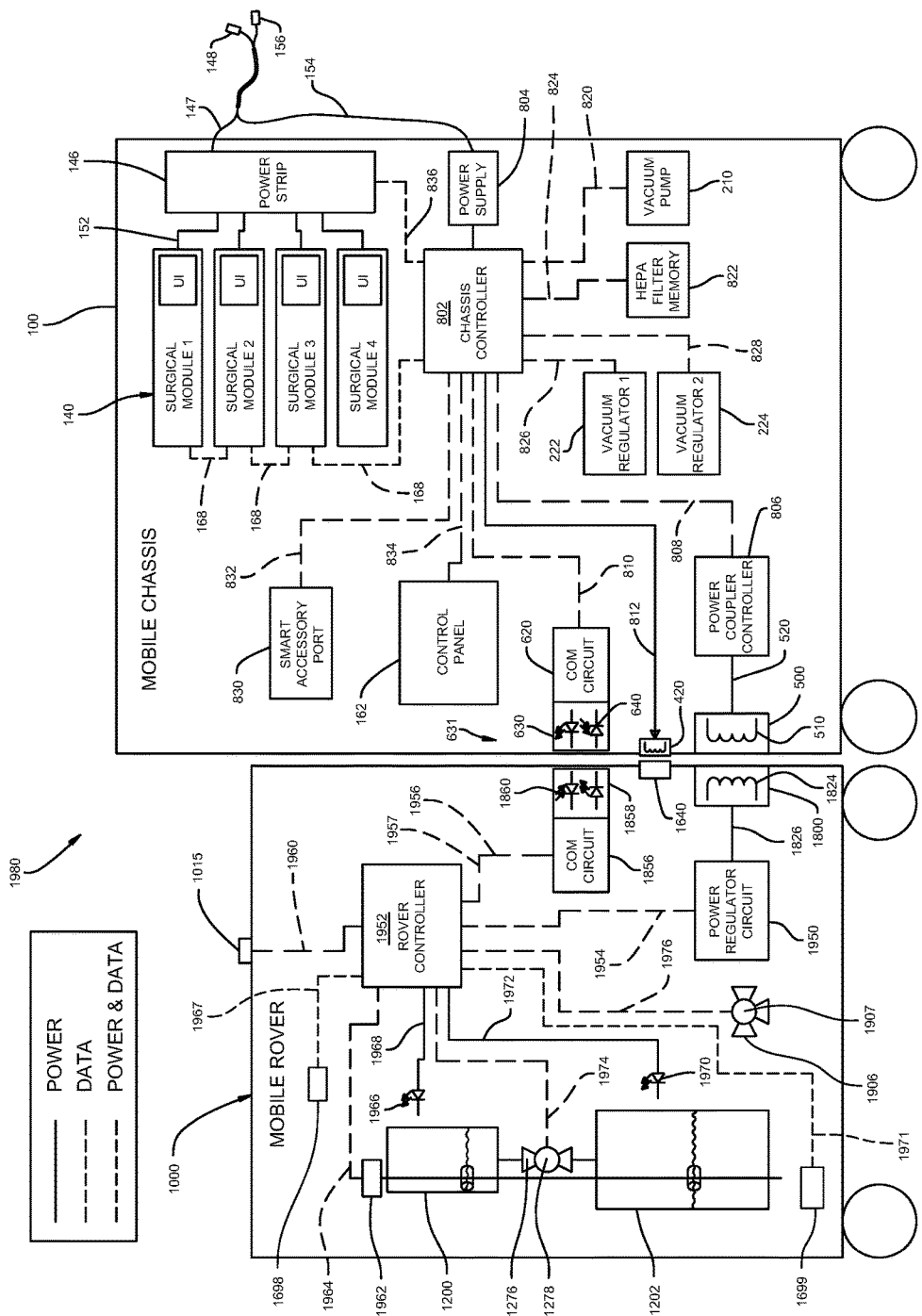
FIG. 23 is a schematic diagram of the electrical and control system of the waste/surgical waste collection system of the present invention.

FIG. 23 illustrates a schematic diagram of a power and control system 1980 for providing electrical power and controlling the operation of mobile chassis 100 and mobile rover 1000. Power cords 147 and 154 are bundled together for a portion of their length, extending from mobile chassis 100 and terminating in power plugs 148 and 156, respectively. Power plugs 148 and 156 are connected to electrical receptacles in the medical facility to facilitate connection to a utility power system. Power strip 146 is connected to an external source of power through power cord 147 and power plug 148. Power strip 146 supplies power to surgical modules 140 through wires 152.

The power cord 154 and power plug 156 are used to supply electrical power to a power supply 804. Power supply 804 can supply one or more voltage and current levels to mobile chassis 100. Power supply 804 is connected to mobile chassis controller 802. Mobile chassis controller 802 comprises a controller or microprocessor and solid state switches for controlling the operation of components of the mobile chassis 100.

Controller 802 is connected to a power coupler controller 806 via a power and data cable 808. Power coupler controller 806 is connected to power coupler 500 through a power cable 520. Power coupler 500 transfers electrical power via an inductive coupling to mobile rover 1000. Mobile rover 1000 includes a power coupler 1800 connected to a power regulation circuit 1950 through a power cable 1826. Power regulation circuit 1950 is connected to a mobile rover controller 1952 through a power and data cable 1954. Rover controller 1952 draws power from power coupler 1800 via power regulation circuit 1950.

The power coupler 500 has a winding 510 and power coupler 1800 has a winding 1824. When the mobile rover 1000 is mated with the mobile chassis 100, the respective power couplers 500, 1800 and the respective windings 510, 1824 are brought in close physical proximity to one another such that the windings 510 and 1824 are inductively coupled together when AC power is transmitted to winding 510 by power coupler controller 806.

Electric power is transferred across a dielectric gap from winding 510 to winding 1824 supplying power regulation circuit 1950 with a supply of power. This electric power is used by various systems of the mobile rover 1000. Power regulation circuit 1950 controls the voltage, current and frequency of the power and typically supplies DC power to the controller 1952.

Supplying power to mobile rover 1000 through the use of inductive couplings in the power couplers 500 and 1800 prevents power connection reliability problems between rover 1000 and mobile chassis 100 associated with dirty or corroded electrical contacts during the suctioning of waste fluids.

Mobile chassis 100 has a communication circuit 620 that is connected to controller 802 through a power and data cable 810. Communication circuit 620 is connected to an in communication with infrared light emitting diode (IRLED) transmitter 630 and receiver 640. In a similar manner, mobile rover 1000 has a communication circuit 1856 connected to controller 1952 through a power and data cable 1956 that carries data signals 1957. Communication circuit 1856 is connected to IRLED transmitter 1858 and receiver 1860.

When the mobile rover 1000 is mated with the mobile chassis 100, the IRLED transmitters and receivers are brought in close physical proximity to one another such that infrared communication light signals are transmitted between the infrared transmitters and receivers. The respective IRLED transmitter 630, receiver 640, transmitter 1858 and receiver 1860 facilitate data communication between mobile chassis 100 and mobile rover 1000.

When the mobile rover 1000 is docked with the static docker 900 (FIG. 4), rover power coupler 1800 and rover communication circuit 1856 allow the static docker 900 to supply power to and communicate with mobile rover 1000 during waste emptying and cleaning procedures.

With additional reference to FIGS. 9 and 16, controller 802 is further connected to electromagnet 420 via a power cable 812. Electromagnet 420 is packaged with mobile chassis vacuum coupler 400 and metal hub 430. The metal outer hub 1640 is part of the rover vacuum coupler 1600. When the mobile rover 1000 is mated with the mobile chassis 100, metal hub 1640 is brought in close physical proximity to electromagnet 420. When mobile rover 1000 is mated with the mobile chassis 100, mobile rover 1000 receives power from power coupler 500 causing rover controller 1952 to automatically send an electrical signal through data communication circuits 1856 and 620 to chassis controller 802 instructing chassis controller 802 to energize electromagnet 420. When electromagnet 420 is energized, a magnetic field is created that draws the rover outer hub 1640 into contact with the chassis outer hub 430 such that the opposed faces 432 and 1641 are adjacent. Whenever rover 1000 is mated with chassis 100, electromagnet 420 is automatically energized. The continued energizing of electromagnet 420 retains the mobile rover vacuum coupler 1600 to the mobile chassis vacuum coupler 400.

The release button 1015 is mounted to mobile rover 1015 and is in communication with controller 1952. When a user depresses release button 1015, the controller 1952 sends an electrical signal through data communication circuits 1856 and 620 to controller 802 directing controller 802 to de-energize electromagnet 420. When electromagnet 420 is de-energized, the magnetic field is removed from the chassis outer hub 430 thereby releasing the mobile rover vacuum coupler 1600 from the mobile chassis vacuum coupler 400.

Referring only to FIG. 23, chassis controller 802 is in communication with the vacuum pump 210 via a power and data cable 820. Controller 802 controls the operation of vacuum pump 210. Controller 802 is in communication with a HEPA filter memory device 822 via a power and data cable 824. Controller 802 receives a signal from the HEPA filter memory device 822 that indicates that the filter requires changing. Controller 802 is also in communication with vacuum regulator 222 via a power and data cable 826. Controller 802 is also in communication with vacuum regulator 224 via a power and data cable 828. Controller 802 controls the operation of the vacuum regulators 222 and 224 in order to independently regulate the vacuum level supplied to each of waste containers 1200 and 1202.

Controller 802 is further in communication with smart accessory port 830 via a power and data cable 832. Controller 802 interfaces and communicates with various surgical tools and instruments that are equipped to communicate using smart accessory port 830. Controller 802 is also in communication with the mobile chassis control panel 162 via a power and data cable 834. A user can view parameters, adjust settings and control the operation of the mobile chassis 100 and the mobile rover 1000 using control panel 162.

Controller 802 is additionally in communication with surgical modules 140 through data cables or bus 168. Controller 802 is in communication with the power strip 146 via a power and data cable 836.

The mobile rover controller 1952 is further in communication with the release button 1015 through a data cable 1960. Controller 1952 is also in communication with a waste container level sensor 1962 through a data cable 1964. Level sensor 1962 generates electrical signals that are representative of the level of waste in each of waste containers 1200 and 1202. The level of waste can be displayed on control panel 162. Controller 1952 is in communication with LED lights 1966 through a power cable 1968 and with LED lights 1970 through a power cable 1972. A user using control panel 162 can direct controller 1952 to turn LED lights 1966 and 1970 on and off in order to illuminate respective waste containers 1200 and 1202.

Controller 1952 is in communication with pressure sensor 1698 through a data cable 1967. Data cable 1967 carries a pressure signal from pressure sensor 1698 to controller 1952. Controller 1952 is in communication with pressure sensor 1699 through a data cable 1971. Data cable 1967 carries a pressure signal from pressure sensor 1699 to controller 1952. The pressure signals are relayed from rover controller 1952 via communication circuits 1856 and 620 to chassis controller 802. Chassis controller 802 regulates the vacuum drawn on containers 1200, 1202 based at least partially on the pressure sensor signals. In one embodiment, controller 802 controls the operation of the vacuum regulators 222 and 224 based on the pressure sensor signals to independently regulate the vacuum level supplied to each of waste containers 1200 and 1202.

The controller 1952 is also in communication with a transfer valve actuator 1278 through a power and data cable 1974. Controller 1952 can open and close control valve 1276 using actuator 1278. Controller 1952 is additionally in communication with diverter valve actuator 1907 through a power and data cable 1976. Controller 1952 can open and close diverter valve 1906 using actuator 1907.

E. Operation of the First Embodiment

Referring to FIGS. 1 and 2, the medical/surgical waste collection system 50 is prepared for use in the collection of medical/surgical waste. Mobile chassis 100 is typically located in an operating room/surgical area during use. Lockable wheels 130 allow mobile chassis 100 to be positioned in a desired location and oriented by medical personnel. The power plugs 148 and 156 are connected to a power source to supply power to mobile chassis 100 and mobile chassis 100 is turned on by a user through control panel 162.

With additional reference to FIGS. 6 and 11, an empty mobile rover 1000 is moved by a user into mobile chassis void space 124. As the mobile rover 1000 is moved into void space 124, the guide apparatus 1870 engages floating coupler mechanism 300. Specifically, as mobile rover 1000 is moved towards mobile chassis 100, the angled guide rails 1872 engage the angled sections 372 and the angled guide plates 1874 engage lip 377 causing rover guide mechanism 1870 and chassis coupler mechanism 300 to move into an aligned position with respect to each other. At the same time, the coupler mechanism 300, through coil springs 316, slightly moves or floats allowing chassis vacuum coupler 400 and chassis power coupler 500 to move slightly up, down, sideways, and tilt or rotate in order to be aligned with the respective rover vacuum coupler 1600 and rover power coupler 1800.

Eventually, the rover vacuum coupler 1600 will contact the chassis vacuum coupler 400 limiting the forward movement of mobile rover 1000. In this position, the rover power coupler 1800 is adjacent the chassis power coupler 500 such that windings 510 and 1824 are brought in close physical proximity to each other. The windings 510 and 1824 are inductively coupled together and electrical power is provided mobile rover 1000. Also in this position, communication LED's 1858, 1860 (FIG. 23) in the mobile rover and communication LED's in the chassis 630, 640 (FIG. 23) are brought into alignment.

Rover power coupler 1800 and the chassis power coupler 500 automatically connect so as to establish a power connection from the mobile suction cart to the mobile container cart. The communication LED's 1858, 1860 of communication circuit 1856 in the mobile container cart and communication LED's 630, 640 of communication circuit 620 automatically connect so as to establish a data transfer connection from the mobile suction cart to the mobile container cart.

With additional reference to FIG. 23, after power is supplied to mobile rover 1000, the chassis controller 802 automatically begins data communication with the rover controller 1952 through data communication circuits 620 and 1856. In one embodiment, controller 1952 generates data signals 1957 that are transmitted to controller 802 via communication circuits 1856 and 620. Controllers 802 and 1952 can initiate a start up sequence to prepare waste collection system 50 for operation.

With the mobile rover 1000 fully inserted into void space 124, rover controller 1952 communicates instructions to chassis controller 802 to automatically energize electromagnet 420. The electromagnet holds the rover 1000 with high force to the chassis 100 to allow repositioning of the rover and chassis combination if desired without decoupling.

Figure 24:
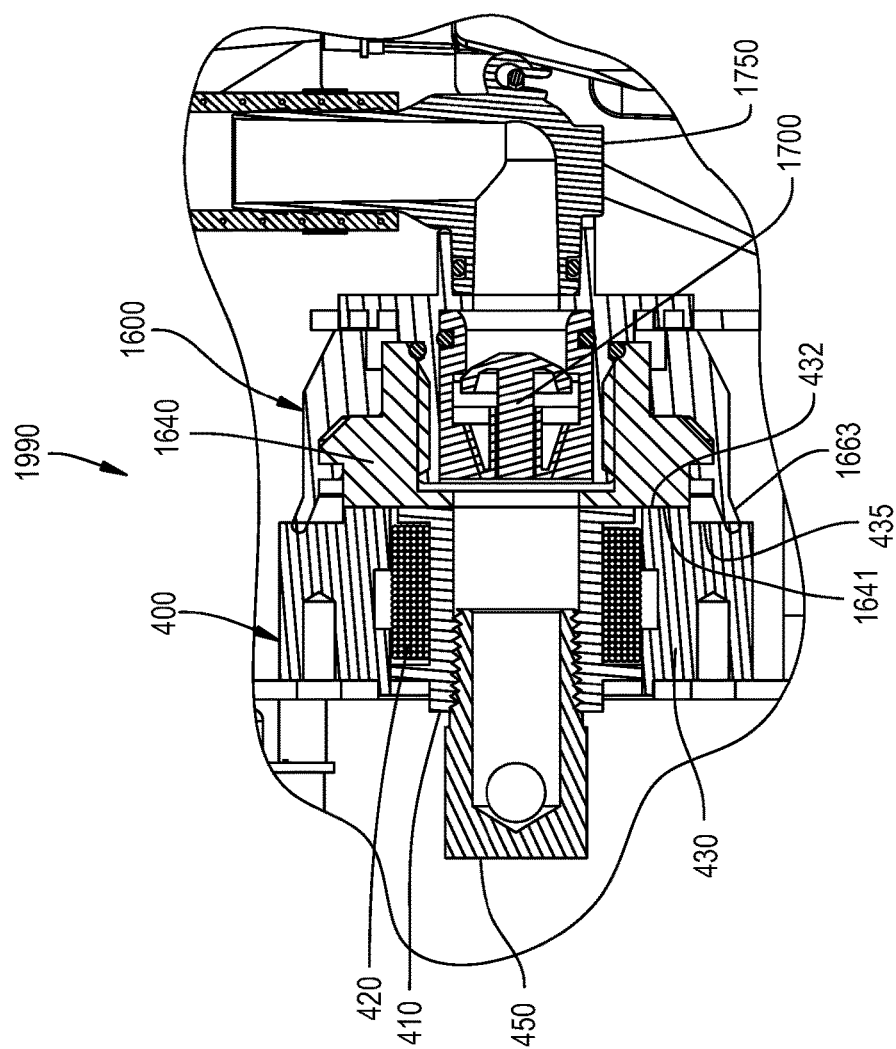
FIG. 24 is an enlarged cross-sectional view of the mobile chassis vacuum coupler mated with the mobile rover vacuum coupler.

Turning to FIG. 24, when electromagnet 420 is energized, the chassis outer hub 430 is also magnetized and attracts the rover outer hub 1640 into contact such that opposed faces 432 and 1641 are in contact. Continued energizing of electromagnet 420 retains the mobile rover vacuum coupler 1600 to the mobile chassis vacuum coupler 400. At the same time that the rover outer hub 1640 moves towards the chassis outer hub 430, the face seal circumferential rim 1663 engages the outer hub step 435 and is compressed against outer hub step 435 causing slight outward radial flexing of rim 1663 and creating a seal 1990 between rover vacuum coupler 1600 and chassis vacuum coupler 400.

Referring back to FIGS. 1, 2 and 3, new disposable manifolds 1260 are inserted into one or both of the manifold receivers 1258 and one or more suction lines 62, 64 are connected to one or more inlets (or ports) on the disposable manifold 1260. The control panel 162 allows a user to selectively turn on and off vacuum pump 210 and to selectively change the amount of vacuum drawn within one or more of the waste containers 1200, 1202 by using the appropriate vacuum regulators 222, 224.

The vacuum pump 210 creates two continuous suction fluid communication paths 70 and 72 that are formed from the suction applicator 62 or 66 to the suction or vacuum pump 210. When vacuum pump 210 is activated, the resultant suction draws waste matter into the respective suction applicator 62 or 66 as selected by a user. The waste stream associated with suction fluid communication path 70 travels from the suction applicator 62 into suction line 60 through manifold 1260 through waste conduit 1270 (FIG. 14) and into upper waste container 1200 where the waste stream is deposited. From waste container 1200, the suction fluid communication path 70, now consisting primarily of air, travels into vacuum conduit 1564 (FIG. 14) and vacuum line 1496 (FIG. 10) through elbow fitting 1750 (FIG. 24) through check valve 1700 (FIG. 24) into inner hub 410 and elbow fitting 450 (FIG. 24). From elbow fitting 450, the suction fluid communication path 70 continues into vacuum hoses 246 (FIG. 6) through vacuum regulator 222 (FIG. 3) through check valve 226 (FIG. 6) through vacuum hose 242 (FIG. 6) through HEPA filter 232 (FIG. 6) into hose 244 (FIG. 6) ending at vacuum pump 210.

The waste stream associated with suction fluid communication path 72 travels from the suction application 66 into suction line 64 through manifold 1260 through waste conduit 1270 (FIG. 14) and into lower waste container 1202 where the waste stream is deposited. From waste container 1202, the suction fluid communication path 72, now consisting primarily of air, travels into vacuum conduit 1564 (FIG. 14) and vacuum line 1510 (FIG. 10) through elbow fitting 1750 (FIG. 24) through check valve 1700 (FIG. 24) into inner hub 410 and elbow fitting 450 (FIG. 24). From elbow fitting 450, the suction fluid communication path 72 continues into vacuum hoses 246 (FIG. 6) through vacuum regulator 224 (FIG. 3) through check valve 228 (FIG. 3), through vacuum hose 242 (FIG. 6) through HEPA filter 232 (FIG. 6) into hose 244 (FIG. 6) ending at vacuum pump 210.

Liquid waste and small pieces of solid waste are deposited into respective waste canisters 1200 or 1202. The waste is thereby stored in the respective waste canister 1200 or 1202 until being emptied.

In an alternative embodiment, the suction fluid communication path 72 into the lower waste container 1202 is omitted such that suctioning of waste fluids only occurs into the upper waste container 1200 and lower waste container 1202 is only used for the storage of waste transferred from the upper waste container 1200.

During the operation of waste collection system 50, various operating parameters can be controlled by a user and waste collection system 50 can alert a user to various operating states or conditions. In one embodiment, a user can elect to illuminate the contents of either waste container 1200 or 1202 using control panel 162 to turn on one or both of light emitting diodes 1968 and 1970. In another embodiment, level sensor 1962 detects when either waste container 1200 or 1202 is approaching being filled and send a level sensor signal representative of an operating state of waste collection system 50 to control panel 162 to alert a user of this condition.

Medical personnel may also operate the surgical modules 140 during or separate from the operation of waste collection system 50 in order to perform various surgical functions.

After a period of time, when the upper waste container 1200 is being used, the upper canister 1218 will become full and need to be emptied, or the operator may elect to empty the upper canister 1218, before being filled. At this point, the user uses control panel 162 to direct the valve actuator 1278 (FIG. 24) to open the transfer valve 1276 (FIG. 3) and transfer waste material from the upper container 1200 to the lower container 1202.

During the transfer of waste material from the upper container 1200 to the lower container 1202, the vacuum present in the upper waste container 1200 is vented to atmospheric pressure through vacuum regulator 222. The vacuum in the lower waste container 1202 is set to a pressure such as the lower desired vacuum level of the two waste containers 1200, 1202. As a result, the vacuum in the lower waste container 1202 assists in pulling waste material into the lower waste container 1202.

Once both the upper 1200 and lower 1202 waste containers are filled, or if the user desires to empty and clean the waste containers 1200 and 1202 prior to being filled, the user can turn off vacuum pump 210 using control panel 162. Button 1015 is then depressed in order to de-activate electromagnet 420. With electromagnet 420 de-activated, medical personnel can remove or uncouple mobile rover 1000 from mobile chassis 100 by pulling on handle 1012 in a direction away from mobile chassis 100. The separable rover allows for the convenient collection of unlimited amounts of fluid waste. A rover with full waste containers can be removed and replaced with another empty rover quickly, minimizing the disruption to an ongoing surgical procedure.

Mobile rover 1000 is then rolled from the surgical area 52 (FIG. 4) to the static docker 900 (FIG. 4) to off-load the waste material to the treatment facility 910 (FIG. 4) and to clean the waste containers 1200 and 1202.

III. Second Embodiment

Figure 25:
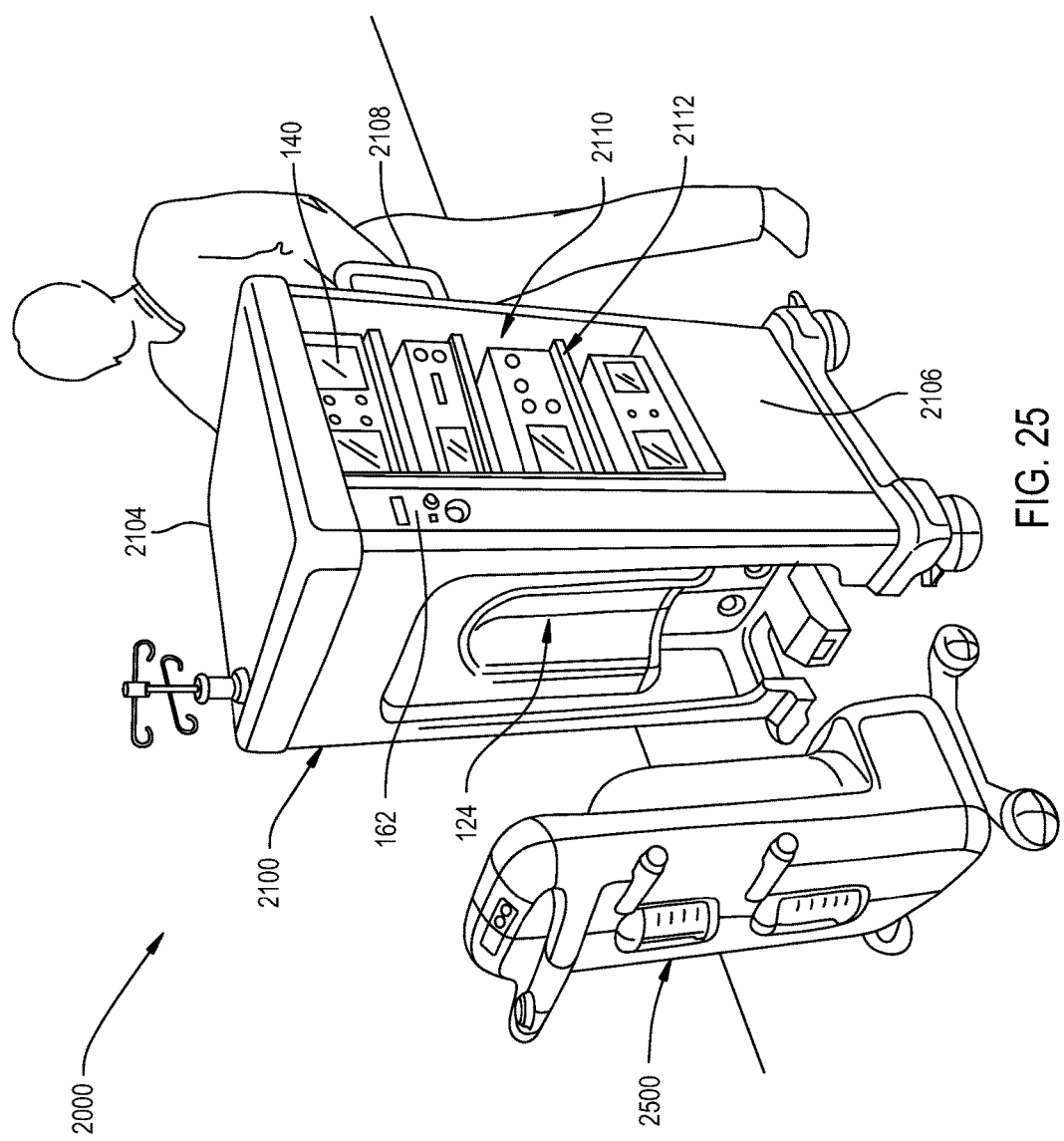
FIG. 25 is a perspective view of an alternative embodiment of a medical/surgical waste collection system in accordance with the present invention showing the mobile rover separated from the mobile chassis.

FIG. 25 illustrates an alternative embodiment of a medical/surgical waste collection system 2000 constructed in accordance with the present invention. Waste collection system 2000 comprises a mobile chassis 2100 and a mobile rover 2500. Mobile rover 2500 is the same as described in the first embodiment except that the shapes and sizes of some of the exterior components have been changed. The internal components and operation of mobile rover 2500 are the same as for mobile rover 1000. Mobile chassis 2100 is sometimes called a suction cart 2100. Mobile rover 2500 is sometimes called a container cart 2500.

Mobile chassis 2100 is similar to mobile chassis 100 of the first embodiment except that the upper chassis 104 (FIG. 1) has been omitted. Mobile chassis 2100 is generally rectangular in shape and includes a generally planar top cover 2104 that extends over four outer side walls 2106 of mobile chassis 2100. Handles 2108 are attached to one or more walls 2106 to allow a user to position mobile chassis 2100. Control panel 162 is mounted to one of walls 2106. A void space 124 is defined in one of walls 2106 within mobile chassis 2100 and receives mobile rover 2500 when mobile rover 2500 is mated with mobile chassis 2100. A rectangular shaped cavity 2110 is defined in one of walls 2106 within mobile chassis 2100. Surgical modules 140 are mounted within cavity 2110 and are supported by shelves 2112 within cavity 2110. The internal components and operation of mobile chassis 2100 are the same as previously described for mobile chassis 100.

IV. Third Embodiment

A. Mobile Chassis

Figure 26:
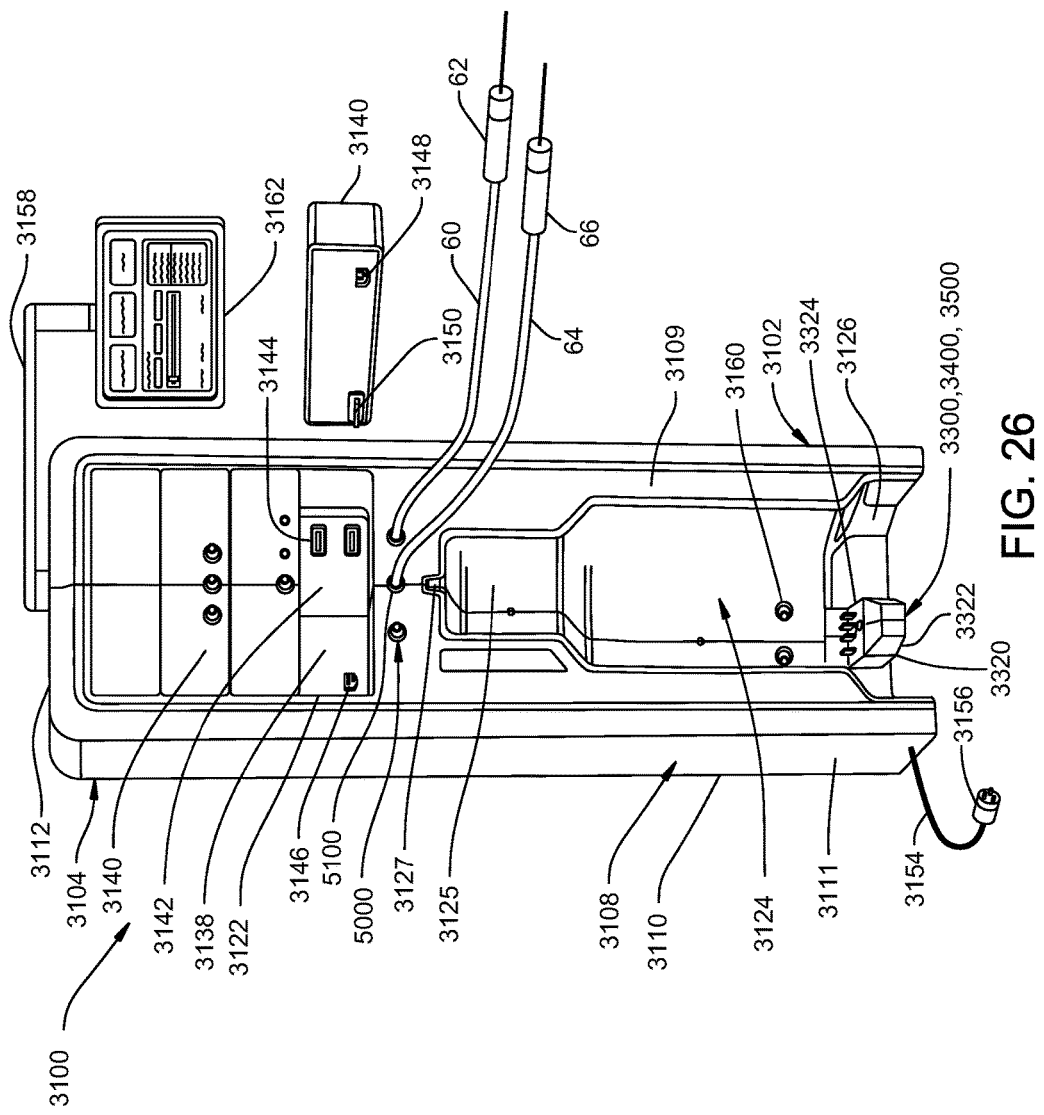
FIG. 26 is a front perspective view of another alternative embodiment of a chassis used in an alternative embodiment of a medical/surgical waste collection system.
Figure 28:
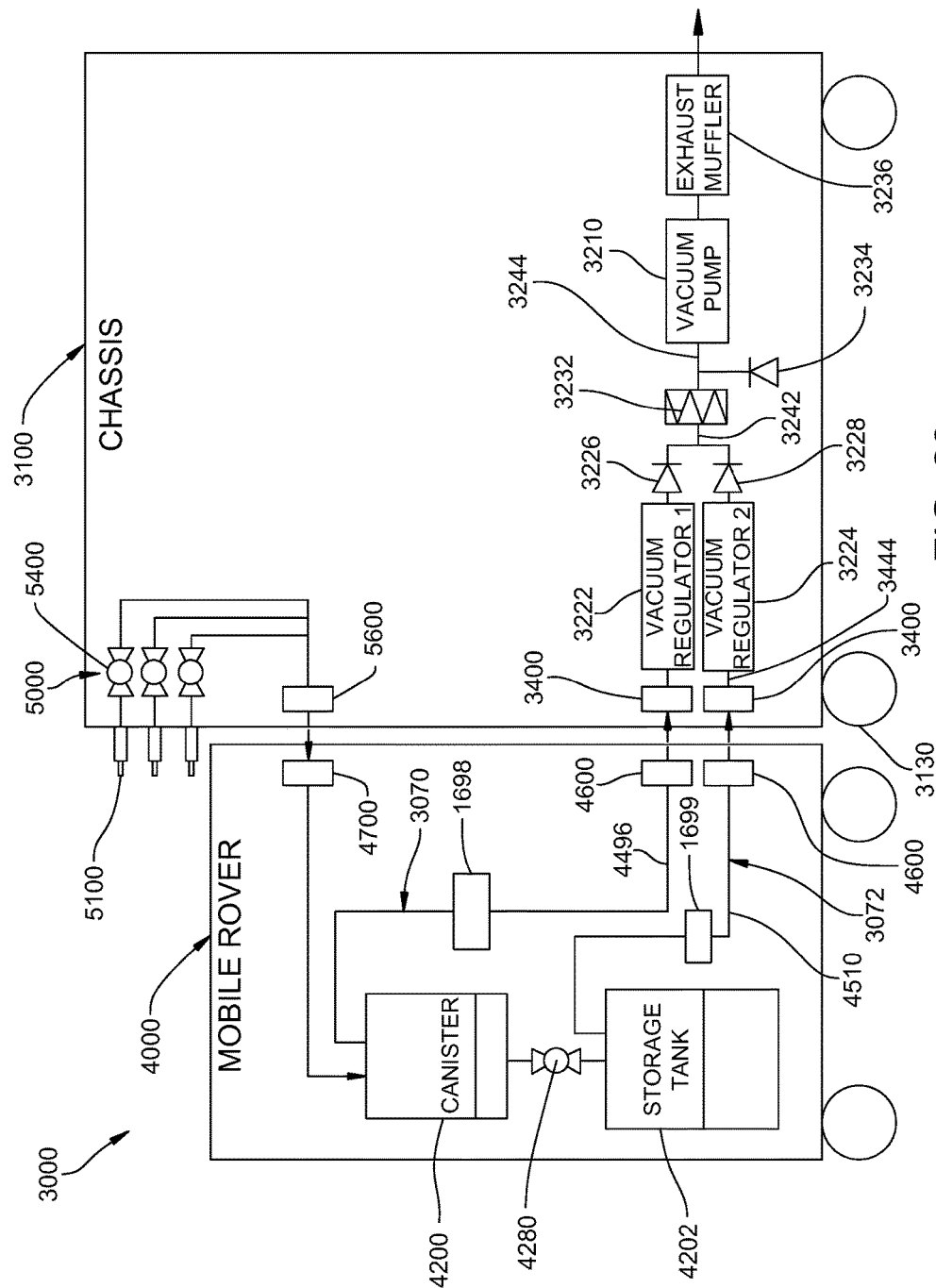
FIG. 28 is a diagrammatic view of the suction fluid communication paths of the chassis and mobile rover of FIGS. 26 and 27 used in an alternative embodiment of a medical/surgical waste collection system.

Turning to FIGS. 26 and 28, waste collection system 3000 includes a chassis 3100 and a mobile rover 4000. Rover 4000 can be mated with the chassis 3100. Chassis 3100 is sometimes called a suction cart 3100. Mobile rover 4000 is sometimes called a container cart 4000. With specific reference to FIG. 26, chassis 3100 is generally rectangular in shape and has a lower chassis 3102 and an upper chassis 3104. Chassis 3100 has an inner frame that supports several outer molded covers 3108. Covers 3108 include front panel 3109, rear panel 3110, side panels 3111 and top panel 3112.

Covers 3108 can be formed from molded plastic and attached to lower chassis 3102 and upper chassis 3104 by suitable methods such as through the use of fasteners. Covers 3108 are used to protect the internal components of chassis 3100 and to provide improved visual aesthetics. A receptacle or void space 3124 is defined in front panel 3109. Void space 3124 receives mobile rover 4000 when mobile rover 4000 is mated to mobile chassis 3100. Void space 3124 has an upper portion 3125 and a lower portion 3126. Front panel 3109 is angled on either side of lower portion 3126 in order to guide mobile rover 4000 into void space 3124 when mobile rover 4000 is mated with mobile chassis 3100. An opening 3127 is defined in front panel 3109 above upper portion 3125.

Figure 4:
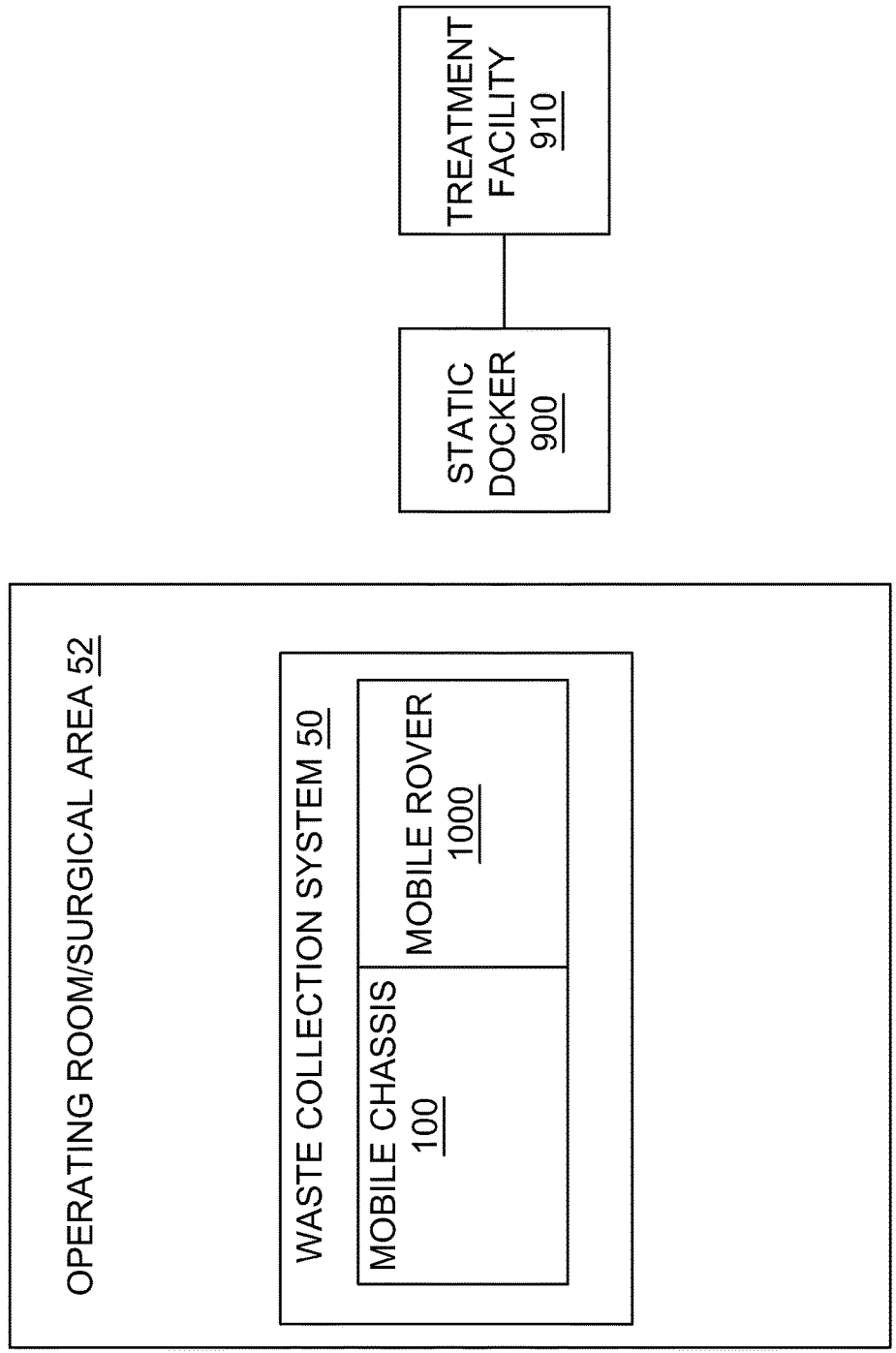
FIG. 4 is a block diagram view of the medical/surgical waste collection system of this invention and a static docker.

A floating coupler mechanism 3300, vacuum coupler 3400 and power and data coupler 3500 extend away from front panel 3109 into receptacle 3124. In the embodiment of FIG. 26, chassis 3100 is shown without wheels. Chassis 3100 can be used in a relatively static position within a surgical area 52 (FIG. 4). In another embodiment, wheels 3130 (FIG. 28) can be attached to chassis 3100 to allow chassis 3100 to be transported and easily moved within operating room/surgical area 52.

An interior cavity 3122 is defined within upper chassis 3104. A component rack 3138 is mounted to upper chassis 3104 within cavity 3122. Component rack 3138 holds a variety of medical/surgical instruments or modules 3140. For example, component rack 3138 can contain equipment, instruments or modules such as an irrigation pump console, electrocautery instrument, an insufflator module, a fiber optic light module or any other suitable surgical instrument or module. Instruments 3140 contain one more memory devices or memory capable of storing data, information and instructions related to the function of instruments 3140. Rack 3138 has an electronic backplane 3142 that includes data connectors 3144 and power connectors 3146. Power connectors 3146 supply power to modules 3140.

Modules 3140 include power connectors 3148 and data connectors 3150. Modules 3140 can be slid into rack 3138. When modules 3140 are mounted in rack 3138, module power connectors 3148 are mated with chassis power connectors 3146 and module data connectors 3150 are mated with chassis data connectors 3144. Power cord 3154 and power plug 3156 are used to supply power to mobile chassis 3100 and modules 3140.

A pivotable support rod 3158 extends over top panel 3112 and bends downwardly along one of side panels 3111. A display assembly or control panel 3162 is mounted to support rod 3158. Support rod 3158 allows medical personnel to position control panel 3162 in an optimal position for viewing and input of commands.

Control panel 3162 controls the operation of the components of chassis 3100 and some of the components of mobile rover 4000. Control panel 3162 can be a touch screen display assembly or can include user input devices such as buttons. In one embodiment, control panel 3162 can control the operation of surgical modules 3140. Display assembly 3162 presents information regarding the operating state of the container cart or the suction cart based at least partially on received sensor signals from pressure sensors 1698, 1699 or level sensors 1962, 4962. Display assembly 3162 can also present information directly display the pressure sensor signals from pressure sensors 1698, 1699 and the level sensor signals from level sensors 1962, 4962. Control panel 3162 can communicate with surgical modules 3140 through backplane 3142 and data connectors 3144 and 3150.

Two electromagnets 3160 face in a distal direction into receptacle 3124. When energized, electromagnets 3160 are used to hold mobile rover 4000 to chassis 3100.

Chassis 3100 includes a manifold assembly 5000 that includes three disposable suction inlet fittings 5100 that are mounted to lower chassis front panel 3109 and extend perpendicularly away from front panel 3109. Suction inlet fittings 5100 are sometimes called suction inlet receivers. Each disposable inlet fitting 5100 receives one of suction lines 60, 64 or another suction line (not shown). The distal end of each suction line 62 and 64 can be attached to a suction applicator hand piece 62 and 66, respectively.

Figure 29:
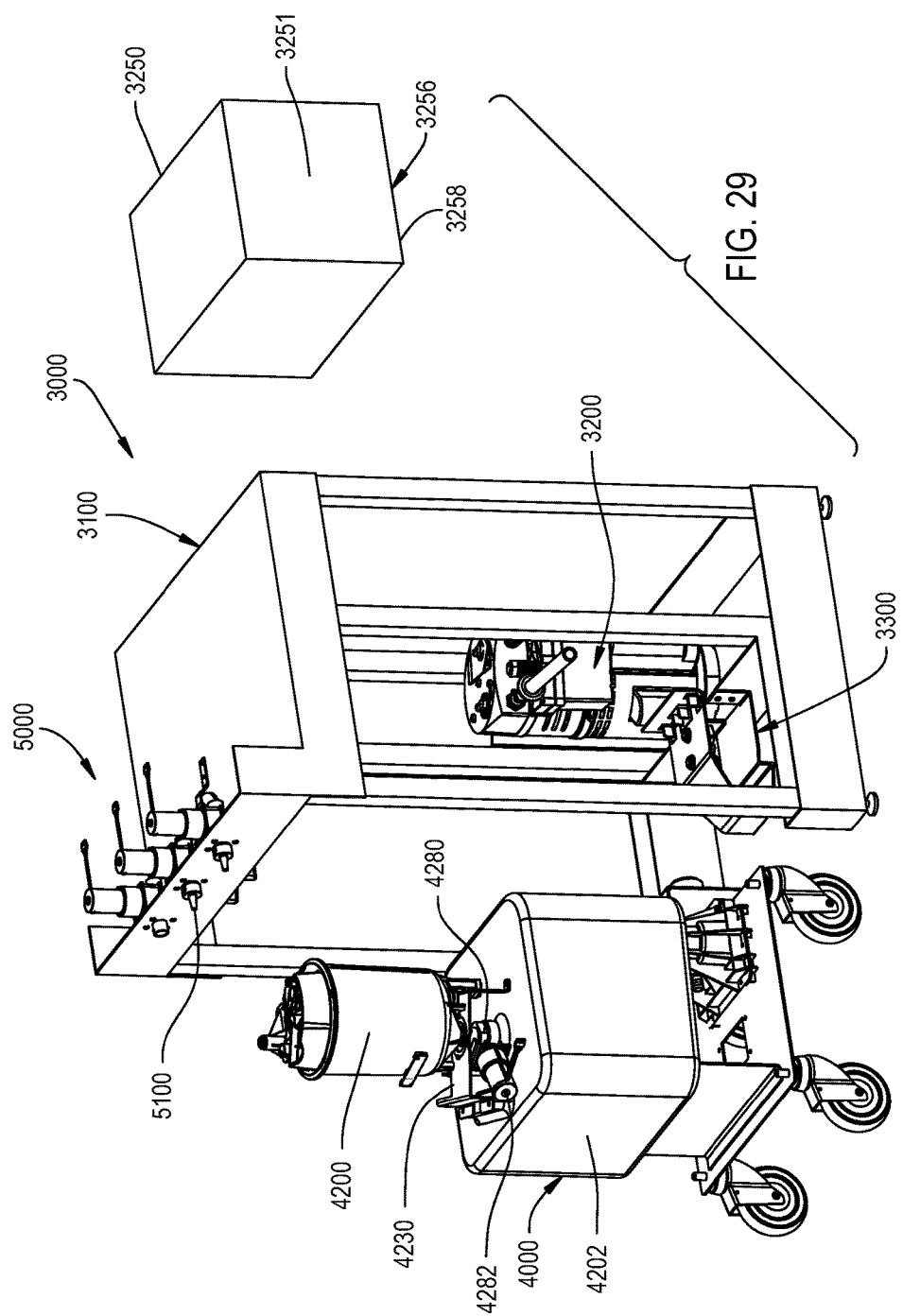
FIG. 29 is a perspective view of the medical/surgical waste collection system of FIGS. 26 and 27 showing the mobile rover separated from the chassis with the covers removed.
Figure 30:
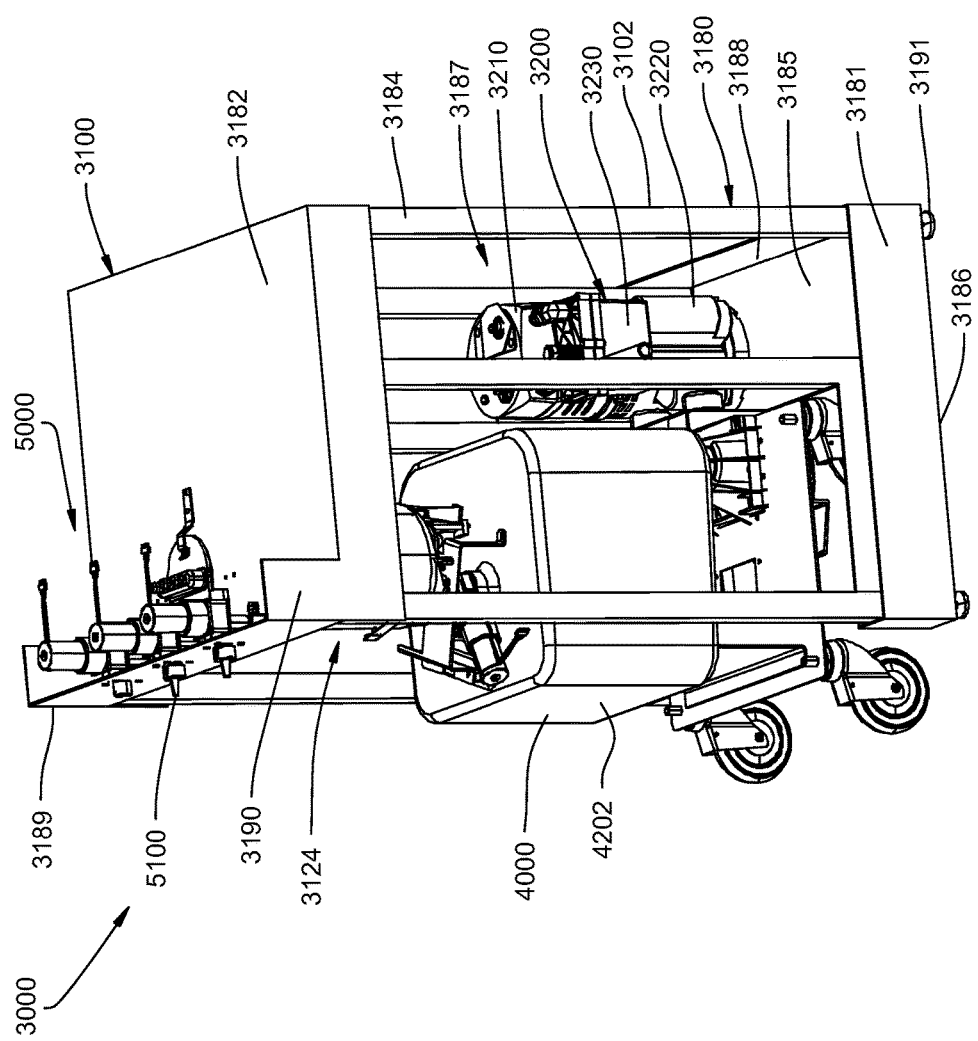
FIG. 30 is a perspective view of the medical/surgical waste collection system of FIG. 29 showing the mobile rover mated with the chassis and the covers removed.

With reference to FIGS. 28, 29 and 30, further details of chassis 3100 are illustrated. In FIGS. 29 and 30, covers 3108 that normally conceal the components of chassis 3100 and upper chassis 3104 are not shown in order for the internal components of chassis 3100 to be more clearly viewed.

Lower chassis 3102 comprises a rectangular shaped frame 3180 that includes a base 3181, a top panel 3182 and six support legs or rails 3184 that extend perpendicularly between base 3181 and planar top panel 3182. Frame 3180 can be formed from a suitable material such as metal. Base 3181 has a central mounting plate 3185 and a pair of arms 3186 that extend generally perpendicularly away from central mounting plate 3185 towards the distal end of chassis 3100. Arms 3186, distal positioned rails 3184 and top 3182 define void space 3124 therein.

The four proximal rails 3184, mounting plate 3185 and top 3182 define an internal cavity 3187. A proximal wall 3188 extends partially upwards from mounting plate 3185 between proximal rails 3184. A rectangular shaped mounting wall 3189 extends perpendicularly upwardly from the distal end of top 3182. A supporting gusset 3190 is attached to each end of mounting wall 3189 and extends in a proximal direction and is attached to top 3182. Four support and leveling feet 3191 are attached to the lower corners of base 3181.

A vacuum and filter assembly 3200 for providing a vacuum source and filtering is mounted to mounting plate 3185. Vacuum and filter assembly 3200 can be the same as vacuum and filter assembly 200. Vacuum and filter assembly 3200 includes a vacuum source or pump 3210, vacuum regulator assembly 3220 and filter assembly 3230. Specifically, vacuum manifold 3220 is mounted to the upper surface of mounting plate 3185. Vacuum pump 3210 and filter assembly 3230 are mounted to vacuum regulator assembly 3220.

With additional reference to FIG. 28, vacuum regulator assembly 3220 integrates vacuum regulators 3222, 3224 and check valves 3226, 3228 into a single unit. Filter assembly 3230 integrates HEPA filter 3232 and vacuum relief valve 3234 into a single unit. A vacuum hose 3242 is connected between check valves 3226, 3228 and HEPA filter 3232. Another vacuum hose 3244 connects vacuum pump 3210 to HEPA filter assembly 3232.

An insulating shell 3250 (FIG. 29) generally encloses vacuum and filter assembly 3200. Insulating shell 3250 attenuates noise that is generated by the vacuum components. Insulating shell 3250 is generally rectangular in shape is defined by five adjoining panels 3251 and has an internal chamber 3256 therein. The interior walls of insulating shell 3250 are covered with sound deadening insulation 3258. Insulating shell 3250 is formed from sheet metal, cast metal, plastic, or other suitable material. Insulating shell 3250 is mounted over vacuum and filter assembly 3200 and is fastened to mounting plate 3185 by fasteners (not shown).

Figure 31:
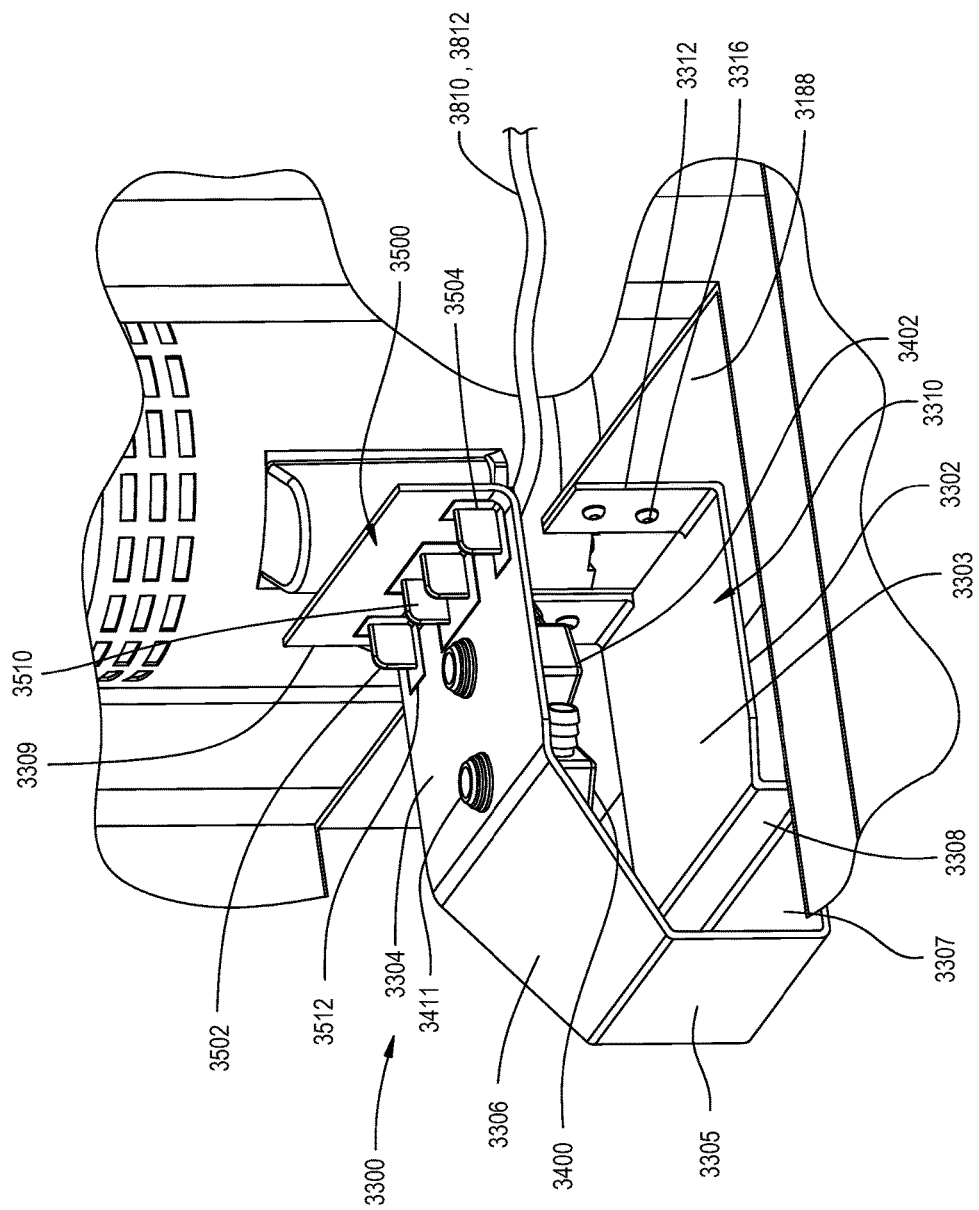
FIG. 31 is an enlarged perspective view of the chassis power coupler, vacuum coupler and floating mechanism.

With additional reference to FIG. 31, chassis 3100 includes a cart coupling feature 3300, also called a retention feature or floating coupler mechanism 3300. Floating coupler mechanism 3300 provides six degrees of freedom for chassis suction or vacuum coupler 3400 and chassis power and data coupler 3500 to move relative to mobile rover 4000 to increase the ability of chassis vacuum coupler 3400 and chassis power and data coupler 3500 to mate with the respective couplings on mobile rover 4000.

Floating coupler mechanism 3300 includes a bent spring bracket 3302 that has a bottom plate 3303, an opposed top plate 3304, a front plate 3305, an angled plate 3306 extending between front plate 3305 and top plate 3304, a connecting plate 3307 and a step plate 3308. All of the plates are connected to each other to form bracket 3302. Bracket 3302 can be formed from a metal material. Plates 3304-3308 define a passage 3310 there between. A bent flange 3309 extends upwardly from top plate 3304. Two spaced apart arms 3312 are located along a proximal end of bottom plate 3302 and extend perpendicularly away from bottom plate 3302. Fasteners 3316 secure arms 3312 to proximal wall 3188.

A bracket 3302 extends in a distal direction into void space 3124 and specifically into the lower section 3126 of void space 3124. Bracket 3302 acts as a spring and allows the top plate 3304 and the flange 3309 to flex toward and away from bottom plate 3310. The top plate 3304 and flange 3309 also slightly flex from side to side and in a distal and proximal direction.

The floating coupler mechanism 3300 further includes a cover or shroud 3320 (see FIG. 26) that is mounted over and to spring bracket 3302. Shroud 3320 includes angled sections 3322 and a lip 3324 that extends outwardly from opposed top edges of shroud 3320. Angled sections 3322 and lip 3324 assist with the centering of mobile rover 4000 into chassis 3100 when mobile rover 4000 is mated with chassis 3100. Floating coupler mechanism 3300 allows chassis vacuum coupler 3400 and chassis power and data coupler 3500 to move slightly up or down in order to more easily be aligned with corresponding mating features of mobile rover 4000. In particular, plate 3304 and flange 3309 can tilt and move slightly in position relative to frame 3180. As a result, chassis vacuum coupler 3400 and chassis power and data coupler 3500 can tilt up or down against the bias of spring bracket 3302 to facilitate mating with corresponding couplers on mobile rover 4000.

Figure 32:
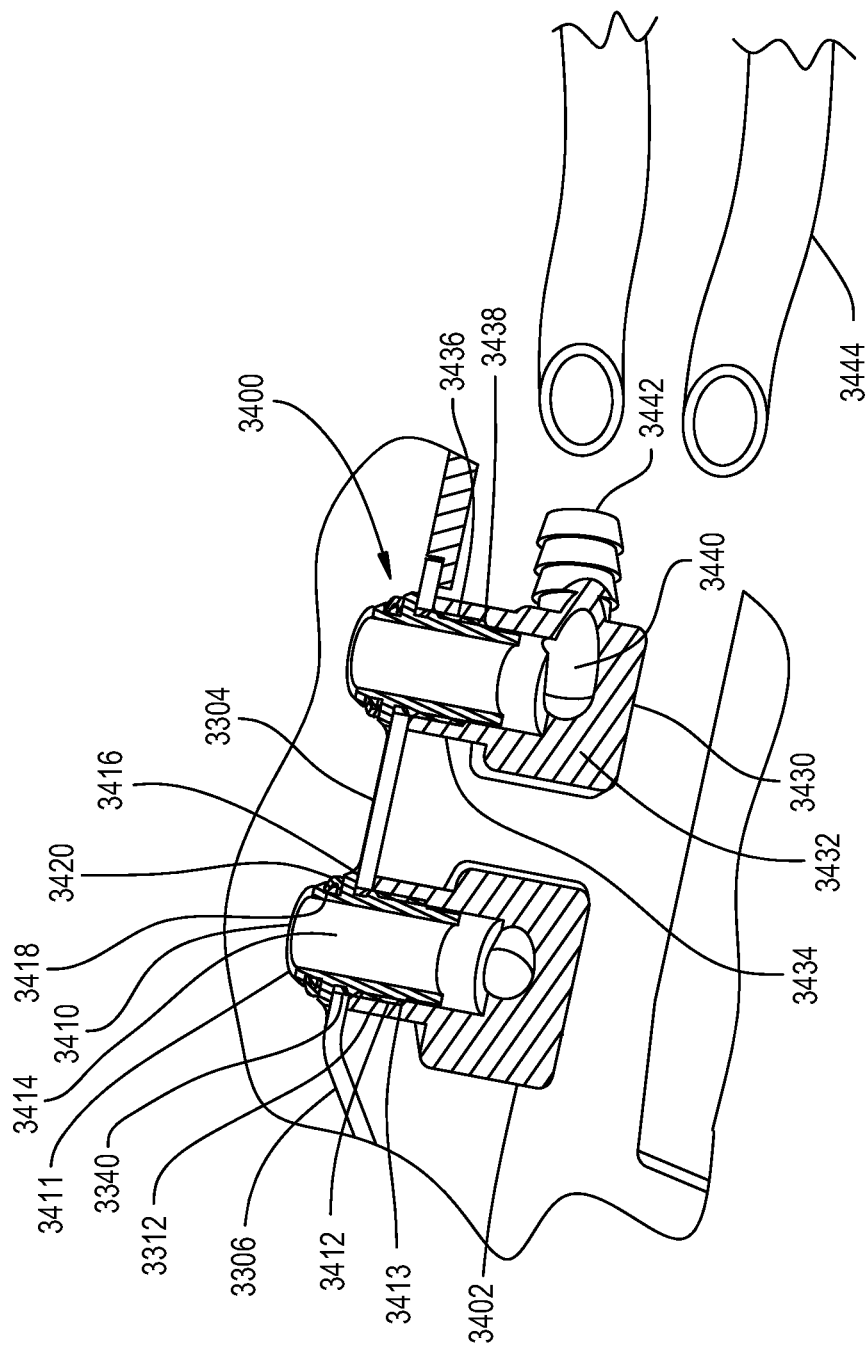
FIG. 32 is an enlarged cross-sectional view of the vacuum coupler of FIG. 31.

FIGS. 31 and 32 illustrate details of chassis vacuum couplers 3400. Two chassis vacuum couplers 3400 are mounted to top plate 3304. Each chassis vacuum coupler 3400 comprises a ninety degree elbow fitting 3402 that includes a threaded cylindrical shaped inner barrel 3410 and an outer threaded body 3430. Inner barrel 3410 is generally cylindrical in shape with a tapered end 3411 and an annular outer surface 3412. External threads 3413 are defined on outer surface 3412. Inner threaded barrel 3410 further has a thru bore 3414 and an outwardly extending flange 3416 located toward one end of inner barrel 3410.

Inner barrel 3410 is mounted through apertures 3340 in top plate 3304. Flange 3416 rests against top plate 3404. An annular groove 3418 is defined in annular outer surface 3412. A seal 3420 is mounted in groove 3418.

Outer threaded body 3430 includes a base 3432 and a cylindrical boss 3434 that extends away from base 3432. Boss 3434 has an inner surface 3436 upon which are defined internal threads 3438. A thru bore 3440 extends through base 3432 and boss 3434.

Inner barrel 3410 is received in bore 3440 with the barrel external threads 3413 mated with the base internal threads 3438 thereby retaining elbow fitting 3402 to top plate 3304. A barbed fitting 3442 extends from one side of base 3432. A vacuum hose 3444 is mounted over each barbed fitting 3442. Vacuum hoses 3444 connect chassis vacuum couplers 3400 to vacuum regulators 3222 and 3224 (FIG. 28), respectively. Each vacuum hose 3444 extends from fitting 3442 to vacuum regulator assembly 3220 (FIG. 30) that contains vacuum regulators 3222 and 3224 (FIG. 28).

Returning to FIG. 31, further details of chassis power and data coupler 3500 are illustrated. Chassis power and data coupler 3500 transfers electrical power and data via electrical contacts from chassis 3100 to mobile rover 4000. Chassis power and data coupler 3500 has four blade shaped contacts including a power contact 3502, a ground contact 3504 and data contacts 3510. Contacts 3502, 3504 and 3510 are each surrounded by an area of electrically insulating material 3512. Contacts 3502, 3504 and 3510 are mounted at the inner junction of top plate 3304 and flange 3309 and extend perpendicularly to both top plate 3304 and flange 3309. Contacts 3502, 3504 and 3510 are formed from a conductive metal such as a copper alloy and may be plated to withstand arcing and prevent corrosion. Contacts 3502, 3504 and 3510 mate with corresponding contacts on mobile rover 4000 as will be described later with the discussion of mobile rover 4000.

Figure 44:
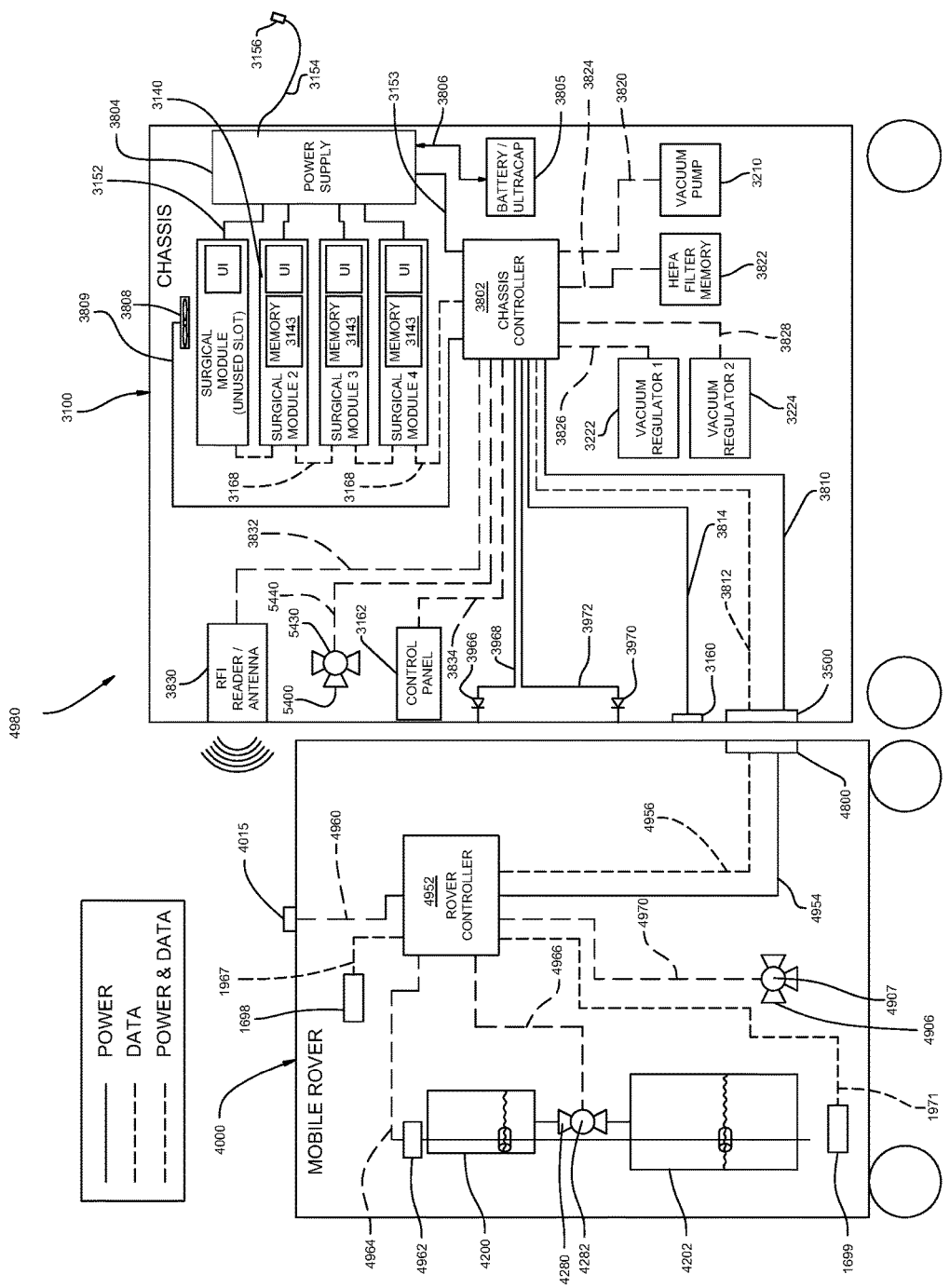
FIG. 44 is a schematic diagram of the electrical and control system of the waste/surgical waste collection system of FIGS. 26 and 27.

Electrical cable 3810 connects contacts 3502 and 3504 to a source of electrical power within chassis 3100. The chassis power and data coupler 3500 provides electric power and data communication to mobile rover 4000. This electric power is used by various systems of the mobile rover 4000. Electrical cable 3812 connects data contacts 3510 to a chassis controller 3802 (FIG. 44). Data contacts 3510 facilitate the exchange of data and information between chassis 3100 and mobile rover 4000.

Figure 33A:
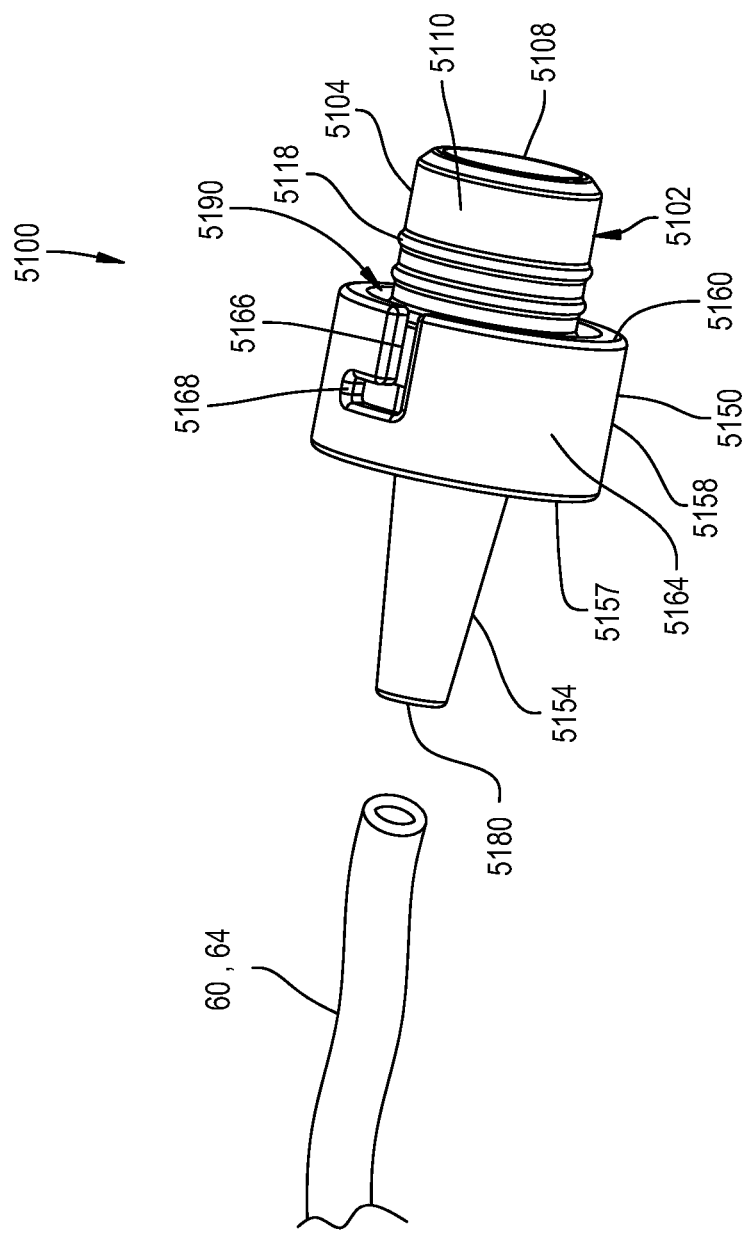
FIG. 33A is a perspective view of a disposable inlet fitting.
Figure 33B:
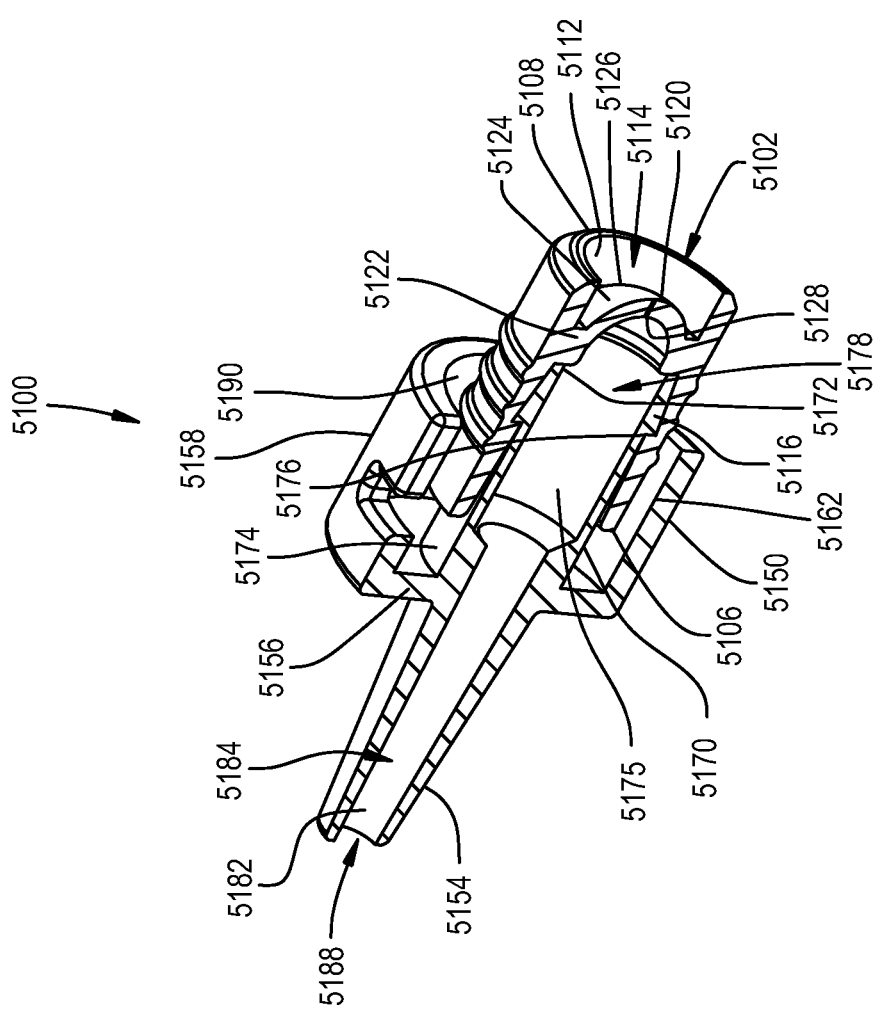
FIG. 33B is a cross-sectional view of the disposable inlet fitting of FIG. 33A.

With specific reference to FIGS. 33A and 33B, details of disposable inlet fittings 5100 are illustrated. Disposable inlet fitting 5100 comprises a cylindrical cap 5150 with a distal facing tapered nozzle 5154 and a proximal barrel 5102. Tapered nozzle 5154 is adapted to receive one of suction lines 60, 64 and to form a vacuum seal with suction lines 60, 64. Cap 5150 and barrel 5102 are collectively coupled together to form inlet fitting 5100.

The most proximal portion of the inlet fitting is barrel 5102. Barrel 5102 is generally cylindrical in shape and has a tubular shaped side wall 5104 with a distal end 5106 and a rounded proximal end 5108. Side wall 5104 is formed to have an outer surface 5110 and an inner surface 5112. Inner surface 5112 defines a thru bore 5114. An annular tapered groove 5116 is defined in inner surface 5112 near the center of barrel 5102. Three raised ridges or ribs 5118 extend circumferentially outward around outer surface 5110 near the center of barrel 5102.

A drip stop and backflow preventer 5120 is integrally formed with barrel 5102 and is positioned within bore 5114 toward proximal end 5108. Barrel 5102 is formed from a compressible, elastomeric material such as polyisoprene rubber. Drip stop and backflow preventer 5120 has a ring shaped base 5122 and a head 5124 with a concavo-convex profile that is integral with and projects in a proximal direction from base 5124. Drip stop head 5124 includes two flexible diametrically opposed lips 5126. Lips 5126 abut each other so as to define a slot 5128 therebetween.

Slot 5128 has a length slightly less than the diameter of bore 5114. The normal abutment of the opposed lips 5126 of drip stop head 5124 blocks the flow from proximal end 5108 of any small amounts of waste fluid retained in inlet fitting 5100 when inlet fitting 5100 is disconnected. When vacuum suction is applied thru bore 5114, opposed lips 5126 flex and move in a proximal direction towards inner surface 5112 such that the distance between lips 5126 is increased and the dimension of slot 5128 is increased thereby allowing suction fluid flow through drip stop 5120 and barrel 5102.

With continued reference to FIGS. 33A and 33B, features of cap 5150 will now be described. Cap 5150 can be formed from a single piece of molded plastic such as polypropylene.

Cap 5150 has a flange 5156 with a distal facing surface 5157. A proximal extending cylindrical shaped skirt 5158 extends from flange 5156 and terminates at end 5160. Skirt 5158 has an annular inner surface 5162 and an annular outer surface 5164. A slot 5166 is defined in skirt 5158 beginning at end 5160 and extending in a distal direction approximately half the width of skirt 5158. Slot 5166 makes a ninety degree bend and extends into a notch 5168 that is contiguous with slot 5166.

A tubular shaped sleeve 5170 projects in a proximal direction from flange 5156 and terminates at end 5172. Sleeve 5170 has an annular outer surface 5174, an inner surface 5175 and a circumferential lip 5176 that projects radially outwards from the outer surface 5164 and is located towards end 5172. Inner surface 5175 defines a sleeve bore 5178.

Barrel 5102 fits over and is retained to sleeve 5170. In particular, sleeve 5170 fits into the opening at barrel distal end 5106 and is received in barrel bore 5114. Sleeve 5170 slides within bore 5114 until sleeve end 5172 abuts a portion of base 5122 extending into bore 5114 and sleeve outer surface 5174 is juxtaposed to barrel inner surface 5112. In this position, sleeve lip 5176 is seated in barrel groove 5116 preventing barrel 5102 from moving in a proximal direction relative to sleeve 5170 and thereby retaining barrel 5102 to cap 5150. The compression of the barrel inner surface 5112 around the sleeve outer surface 5174 substantially eliminates loss of suction between the cap 5150 and the barrel 5102.

Cap 5150 further includes a distal facing tapered nozzle 5154 that extends in a distal direction from flange distal face 5157. Tapered nozzle 5154 receives one of suction lines 60, 64. Nozzle 5154 has a distal end 5180 and a tapered inner surface 5182. Inner surface 5182 defines a bore 5184. Bores 5114, 5178 and 5184 are all contiguous forming a continuous fluid carrying bore 5188 through inlet fitting 5100. A circumferential slot 5190 is defined between skirt inner annular surface 5162 and barrel outer annular surface 5110. Slot 5190 begins at skirt end 5160 and terminates at the proximal face of flange 5156.

Referring to FIG. 33C, another embodiment of a disposable inlet fitting 5800 is illustrated. Disposable inlet fitting 5800 is similar to disposable inlet fitting 5100 except that disposable inlet fitting 5800 further includes multiple nozzles 5854, 5856 and a removable filter 5900. Disposable inlet fitting 5100 comprises a cylindrical cap 5850 with two distal facing tapered nozzles 5854, 5856 and a proximal barrel 5802. Tapered nozzles 5854 and 5856 are adapted to receive one of suction lines 60, 64 and to form a vacuum seal with suction lines 60, 64. Cap 5850 and barrel 5802 are collectively coupled together to form inlet fitting 5800.

The most proximal portion of the inlet fitting is barrel 5802. Barrel 5802 is generally cylindrical in shape and has a tubular shaped side wall 5804 with a distal end 5806 and a rounded proximal end 5808. Side wall 5804 is formed to have an outer surface 5810 and an inner surface 5812. Inner surface 5812 defines a thru bore 5814. Three raised ridges or ribs 5818 extend circumferentially outward around outer surface 5810 near the center of barrel 5802.

Barrel 5802 can include a drip stop and backflow preventer (not shown) the same as described for inlet fitting 5100 in order to prevent leaking of waste fluids when inlet fitting 5800 is disconnected. Barrel 5802 is formed from a compressible, elastomeric material such as polyisoprene rubber.

With continued reference to FIG. 33C, features of cap 5850 will now be described. Cap 5850 can be formed from a single piece of molded plastic such as polypropylene. Cap 5850 has a head 5855 with a distal facing surface 5857 and a base 5861. A proximal extending cylindrical shaped skirt 5858 extends from base 5861 and terminates at end 5860. Cap 5850 has an outer surface 5864 and skirt 5858 has an annular inner surface 5862. A slot 5866 is defined in skirt 5858 beginning at end 5860 and extending in a distal direction approximately the width of skirt 5858. Slot 5866 makes a ninety degree bend and extends into a notch (not shown in FIG. 33C). A circumferential slot 5889 is defined between skirt inner annular surface 5862 and barrel outer annular surface 5810. Cap 5850 includes the same internal components as inlet fitting 5100 such as a sleeve (not shown) that allow cap 5850 to be coupled with and retained to barrel 5802.

Cap 5850 further includes two distal facing tapered ports or nozzles 5854 and 5856 that extend in a distal direction from head distal face 5857. Tapered nozzles 5854, 5856 can each receive one of suction lines 60, 64. Nozzle 5854 has a distal end 5880 and a tapered inner surface 5882. Inner surface 5882 defines a bore 5884. Nozzle 5856 has a distal end 5881 and a tapered inner surface 5883. Inner surface 5883 defines a bore 5885. While two nozzles 5854 and 5856 are shown in FIG. 33C, more or few nozzles can be utilized with inlet fitting 5800. A cover or lid 5870 can be mounted to one or both of ends 5880, 5881 in order to close one or both nozzles 5854, 5856 when not in use.

Cap 5850 includes a center section 5872. A rectangular shaped filter cavity 5890 is defined in center section 5872. Filter cavity 5890 is defined by four side walls 5891 and a bottom wall 5892. An opening 5893 is defined in the distal most wall 5891. A chamber 5894 is defined within head 5855 and is connected to bores 5854 and 5855 and is connected to opening 5893. Bores 5854, 5856, chamber 5894, opening 5893, filter cavity 5890 and bore 5814 are all contiguous forming a continuous fluid carrying path through inlet fitting 5800.

Removable filter 5900 is generally rectangular in shape and has a housing 5910. Housing 5910 is defined by two opposed planar side walls 5912 and two opposed planar side walls 5914. Walls 5912 and 5914 define an interior cavity 5920. Upper wall 5914 is slightly larger than the size of the cavity 5890 opening such that upper wall 5914 overlaps cap outer surface 5864. A mesh screen or filter grid 5930 is mounted to one side of housing 5910 across cavity 5920. A handle 5916 is attached to upper wall 5914. Handle 5916 allows a user to manually manipulate filter 5900. Filter 5900 and screen 5930 can be formed from a single piece of molded plastic such as polypropylene. In one embodiment, filter 5900 is formed at least partially from a transparent material such that a user can view the contents of filter 5900.

Filter 5900 is received in filter cavity 5890. Filter 5900 can form a seal with cap outer surface 5864 and cavity side walls 5891. Filter 5900 is inserted by a user into filter cavity 5890 such that cavity 5920 faces opening 5893 and upper wall 5914 abuts cap outer surface 5864. In one embodiment, filter 5900 is used to collect solid waste particles such as bone fragments or tissue that may cause blockage or clogging of internal components of chassis 3100 or rover 4000. If filter 5900 becomes obstructed with debris during use, a user can turn off the vacuum through the respective inlet fitting 5800, remove the used filter 5900 and insert a new filter 5900. The used filter is then disposed of as medical waste.

In another embodiment, filter 5900 is used as a specimen collector to collect a tissue sample during a surgical procedure. Medical personnel can insert a new filter 5900 into inlet fitting 5800 and turn on the vacuum through the respective inlet fitting 5800 in order to collect a tissue sample. The tissue sample is trapped against screen 5930 as fluid flows through inlet fitting 5800. After the tissue sample is collected, the vacuum is turned off and filter 5900 containing the tissue sample is removed from inlet fitting 5800 and forwarded to a laboratory for further analysis. A new filter 5900 is then inserted into inlet fitting 5800.

Figure 34:
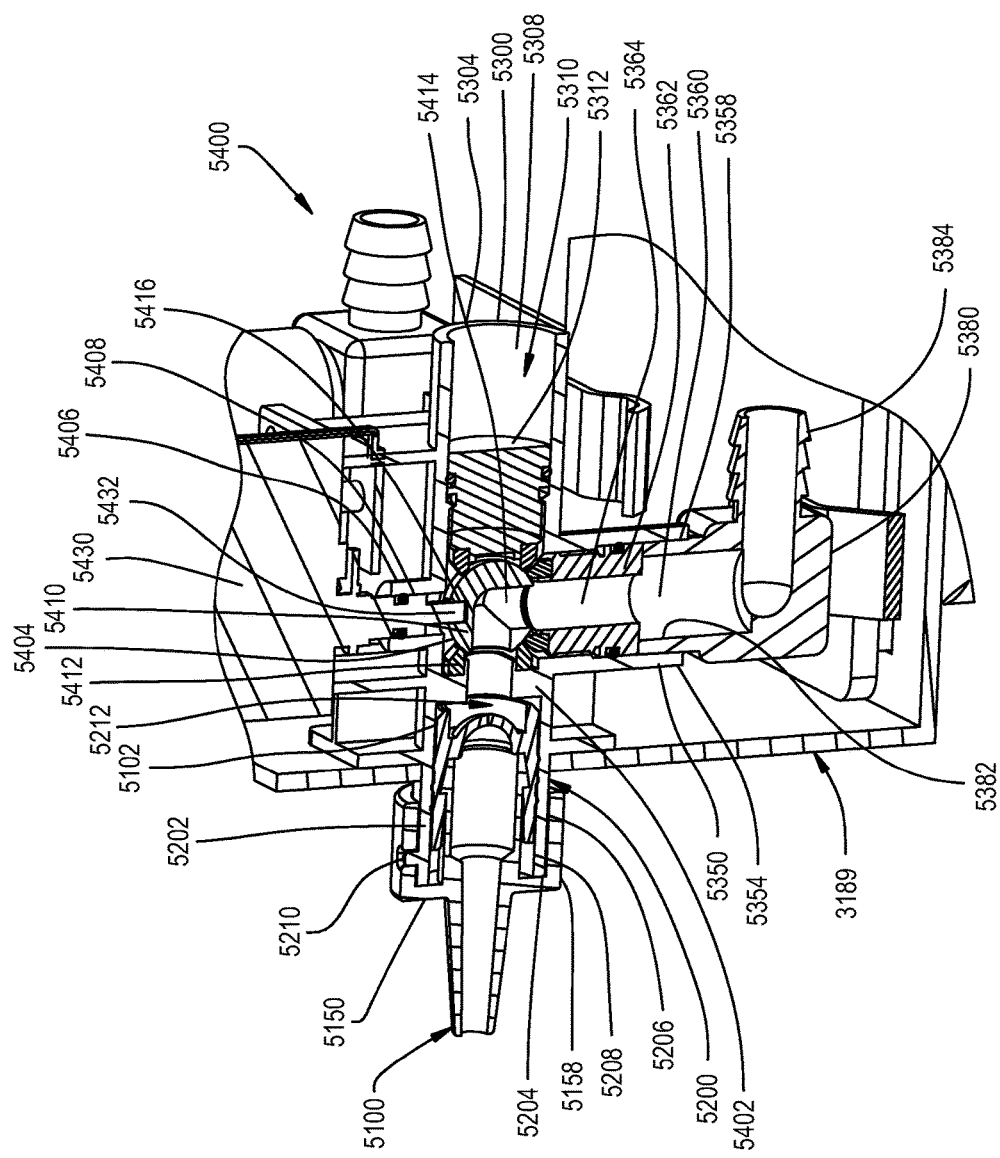
FIG. 34 is an enlarged cross sectional view of a control valve and the disposable inlet fitting mounted to an inlet receiver.

Turning to FIG. 34, an inlet fitting receiver 5200 and a control valve 5400 are shown. Disposable inlet fitting 5100 can be attached and removed from inlet fitting receiver 5200 by a user. Inlet fitting receiver 5200 is part of control valve 5400. Control valve 5400 is mounted to the rear side of chassis mounting wall 3189 by fasteners (not shown). Control valve 5400 includes a generally T-shaped valve body 5402 from which inlet fitting receiver 5200 extends in a distal direction through mounting wall 3189. Valve body 5402 can be formed from a single piece of injection molded plastic such as polypropylene.

Inlet fitting receiver 5200 has a tubular shaped wall 5202 that extends from valve body 5402 and terminates in a distal end 5204. Wall 5202 has an annular outer surface 5206 and an annular inner surface 5208. A post 5210 extends perpendicularly away from outer surface 5206 towards distal end 5204. A bore 5212 extends through receiver 5200 and into valve body 5402. Bore 5212 is defined by annular inner surface 5208.

With additional reference to FIG. 33A, bore 5212 receives inlet fitting 5100. In particular, barrel 5102 is located in bore 5112 with the barrel proximal end 5108 abutting valve body 5402 and receiver inner surface 5208 adjacent barrel outer surface 5110. Receiver wall 5202 fits into skirt annular slot 5190. The distal wall end 5204 abuts the proximal face of fitting flange 5156. The barrel ribs 5118 are compressed against the receiver inner surface 5208. The compression of the barrel ribs 5118 against the receiver inner surface 5208 substantially eliminates loss of suction between the inlet fitting receiver 5200 and the barrel 5102.

The disposable inlet fitting 5100 is attached to inlet fitting receiver 5200 by a user grasping cap skirt 5158 and inserting the barrel 5102 into receiver bore 5212. The post 5210 is aligned with slot 5166 and the inlet fitting 5100 is moved in a proximal direction until barrel 5102 is seated in bore 5212. The barrel proximal end 5108 abuts valve body 5402 and the distal end 5204 abuts the proximal face of flange 5156. Skirt 5158 and inlet fitting 5100 are then rotated clockwise such that the post 5210 slips into recess 5168 thereby locking inlet fitting 5100 to inlet fitting receiver 5200.

The disposable inlet fitting 5100 is removed from inlet fitting receiver 5200 by a user grasping cap skirt 5158 and rotating skirt 5158 and inlet fitting 5100 counter clockwise such that post 5210 slips out of recess 5168. Inlet fitting 5100 is then manually pulled in a distal direction by the user causing barrel 5102 to slide out of bore 5112 and post 5210 to slip out of slot 5166.

A tubular duct 5300 extends from valve body 5402 in a proximal direction and terminates in a proximal end 5304. Duct 5300 has an inner surface 5308 that defines a bore 5310. A plug 5312 is threaded into bore 5310 abutting duct inner surface 5308 and sealing bore 5310. Duct 5300 is used during manufacturing of control valve 5400.

Another tubular duct 5350 extends from valve body 5402 in a downward direction and terminates in an end 5354. Duct 5350 has an inner surface 5358 that defines a bore 5360. A plug 5362 is threaded into bore 5360 abutting duct inner surface 5358. A bore 5364 is defined through plug 5362. A ninety degree elbow fitting 5380 is attached to duct 5350. Elbow fitting 5380 has an end 5382 that is fitted into bore 5360 and a barbed end 5384.

Valve body 5402 further has a ball cavity 5404 that contains a spherical valve ball 5410. The valve ball 5410 is supported for rotation within cavity 5404 by three annular tapered seals 5412. Seals 5412 are mounted within cavity 5404. Seals 5412 form a fluid seal between valve ball 5410 and the interior walls of cavity 5404. A bore 5414 having a ninety degree bend is defined through ball 5410. A square shaped slot 5416 is defined in the top of valve ball 5410. A boss 5406 projects perpendicularly upwards away from valve body 5402 and has a thru bore 5408.

A rotary actuator 5430 is attached to the top of valve body 5402 by suitable means such as using fasteners (not shown). Rotary actuator 5430 is a type of electric motor that is connected with a source of electric power. The rotary actuator 5430 has a downwardly extending square shaft 5432 that is received by and fits into square slot 5416. The rotary actuator 5430 is in communication with chassis controller 3802 (FIG. 44). The rotary actuator 5430 can be directed by controller 3802 to rotate in a clockwise and counter clockwise direction in order to rotate the valve ball 5410 between open and closed positions or to one or more intermediate positions in order to control the flow rate through control valve 5400. Therefore, chassis controller 3802 controls the operation of control valve 5400.

In FIG. 34, the valve ball 5410 is shown in an open position. In the open position, a suction fluid can flow through inlet fitting 5100, receiver bore 5412, ball bore 5414, plug bore 5364 and elbow fitting 5380. When the valve ball 5410 is rotated ninety degrees by rotary actuator 5430, the valve ball 5410 is in a closed position blocking the flow of suction fluid through control valve 5400.

Figure 35:
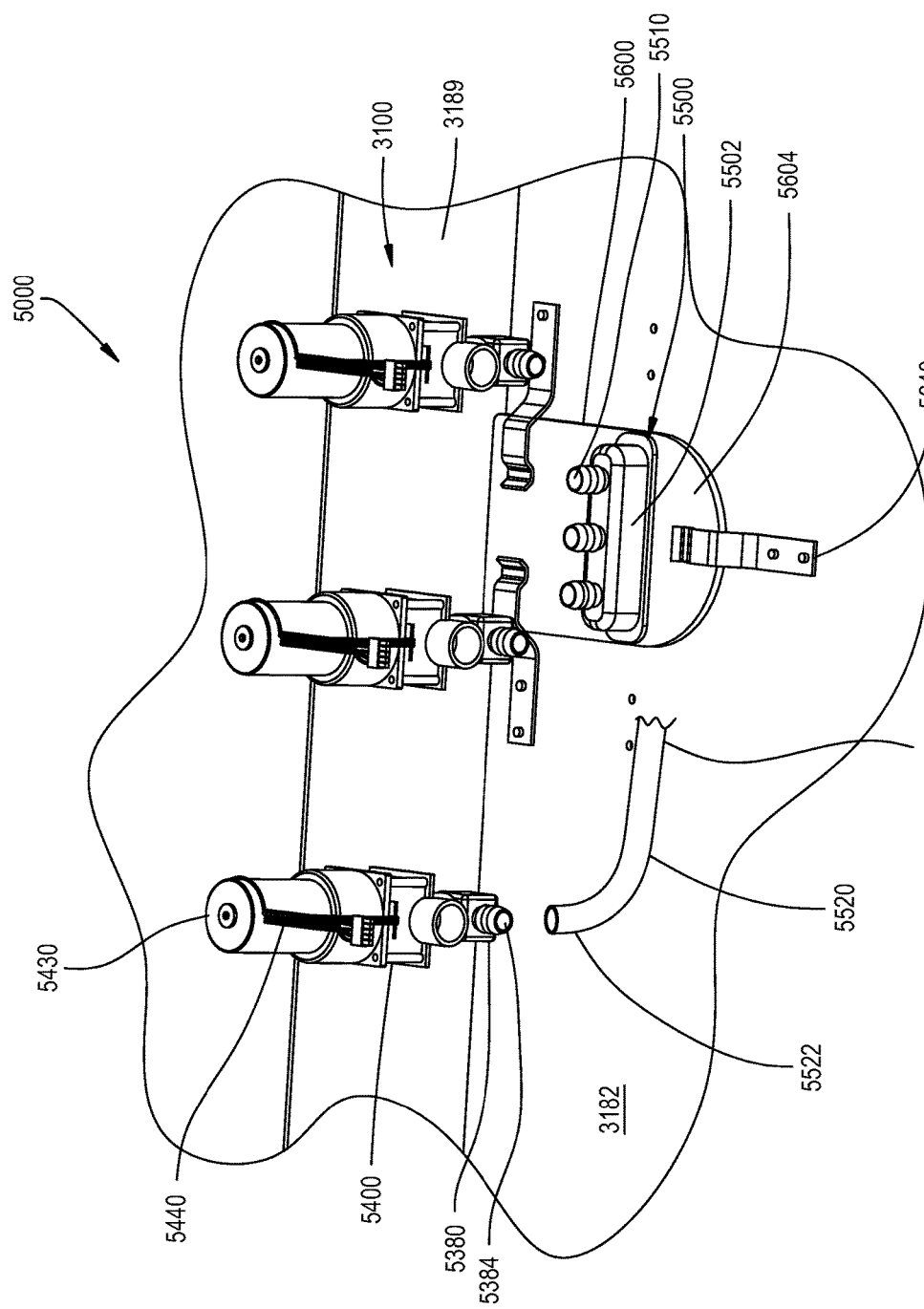
FIG. 35 is a perspective view of an inlet manifold assembly mounted to the chassis.
Figure 36:
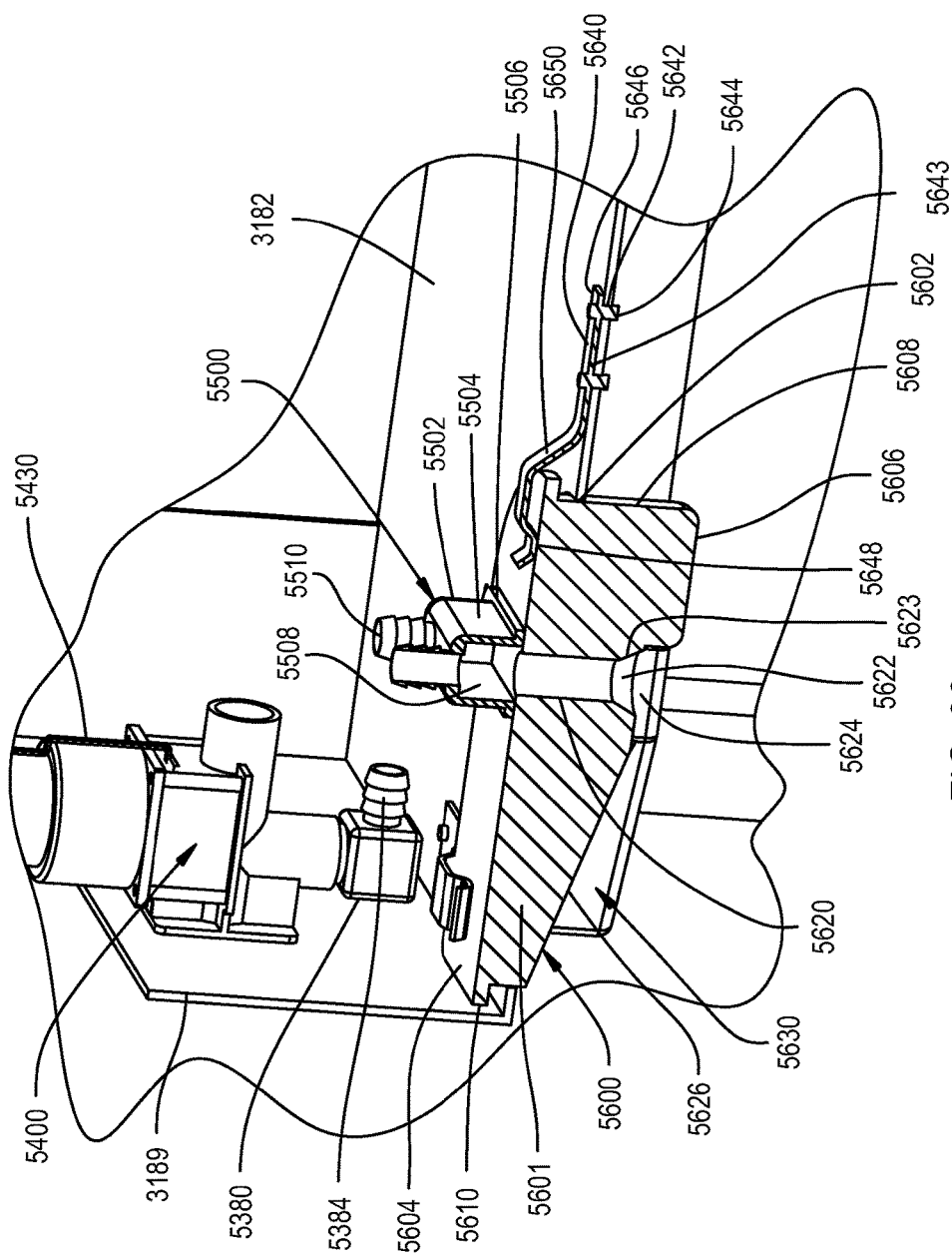
FIG. 36 is a cross sectional view of the inlet manifold.

Referring now to FIGS. 35 and 36, views of the inlet manifold assembly 5000 mounted to the chassis 3100 are shown. Three control valves 5400 are mounted to mounting plate 3189. Each of the control valves 5400 has an associated actuator 5430. An electrical cable 5440 is used to connect each actuator 5430 with a chassis controller 3802 (FIG. 44). Control valves 5400 allow the suction or vacuum to each of the inlet fittings 5100 and suction lines 60, 64 (FIG. 26) to be independently controlled or regulated by setting each control valve 5400 to the desired position.

The inlet manifold assembly 5000 includes a manifold 5500 that is coupled to a chassis waste coupler 5600. Manifold 5500 can be called one end of chassis waste coupler 5600. Manifold 5500 has a generally oval shaped accumulator 5502 that is defined by U-shaped walls 5504. The open end of accumulator 5502 faces waste coupler 5600. A peripheral rim 5506 extends peripherally outwardly from the bottom edge of walls 5504. Walls 5504 define a cavity 5508 within accumulator 5502. Three barbed hose fittings 5510 extend perpendicularly upward from the top surface of accumulator 5502. Manifold 5500 is mounted to the top surface 5604 of chassis waste coupler 5600 using suitable methods such as adhesives or fasteners (not shown). Rim 5506 rests against the top surface 5604.

A vacuum hose 5520 is connected between each control valve 5400 and a respective fitting 5510. Specifically vacuum hose 5520 has ends 5522 and 5524. Hose end 5522 is attached and retained to fitting barbed end 5384 and hose end 5524 is attached and retained to fitting 5510. Hoses 5520 provide a suction fluid communication path between control valves 5400 and manifold 5500.

A chassis waste coupler 5600 is mounted to the frame top panel 3182. Chassis waste coupler 5600 is generally D-shaped and is formed from a single piece of plastic material such as polypropolyene. The frame top panel 3182 has a cutout portion 5602 that receives the chassis waste coupler 5600. The chassis waste coupler 5600 has a central body 5601 with a top surface 5604 and an opposed bottom surface 5606, also called an end. A peripheral side surface 5608 surrounds chassis waste coupler 5600. A peripheral lip 5610 extends outwardly from top surface 5604 over side surface 5608. Lip 5610 rests on the top panel 3182 and prevents the waste coupler 5600 from passing downwardly through cutout 5602.

A bore 5620 extends downwardly from the top surface 5604. A beveled counter bore 5622 extends upwardly from the top of a recess 5624 located in bottom surface 5606. The beveled counter bore 5622 is defined by a truncated cone shaped surface 5623 that faces towards recess 5624. Bore 5620, beveled counter bore 5622 and recess 5624 are all co-axial and extend entirely between top surface 5604 and bottom surface 5606. A bottom facing angled surface or wall 5626 extends from recess 5624 to side surface 5608. The angled surface or wall 5626 defines a guide receptacle 5630.

The chassis waste coupler 5600 is movably coupled to chassis top panel 3182 by three spring clips 5640. Apertures 5642 are defined in top panel 3182. Spring clips 5640 have an end 5646 and a U-shaped clamp end 5648. Apertures 5643 are defined in end 5646. The spring clips 5640 are attached to the top panel 3182 by fasteners 5644 that pass through apertures 5642 and 5643. The clamp end 5648 engages and presses against waste coupler top surface 5604.

The spring clips 5640 further have a center spring section 5650 located between ends 5646 and 5648. Spring section 5650 allows spring clips 5640 to bend and to bias chassis waste coupler 5600 in a downward direction. The spring clips 5640 allow waste coupler 5600 to move slightly upward when mobile rover 4000 is mated to chassis 3100. The spring clips 5640 also provide a downward bias of the waste coupler 5600 towards mobile rover 4000 when the mobile rover 4000 is mated to chassis 3100.

B. Mobile Rover

Figure 37:
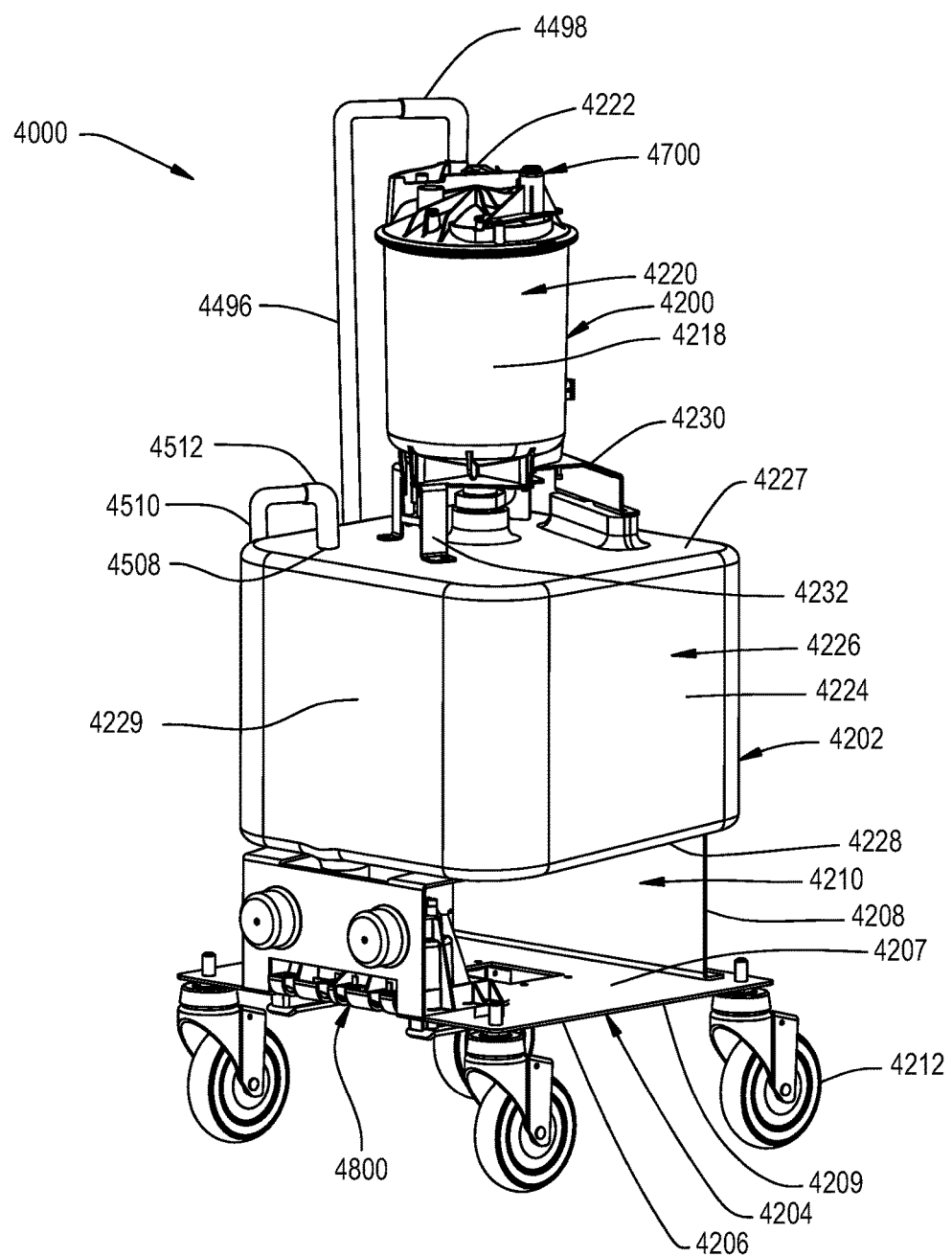
FIG. 37 is a rear perspective view of the mobile rover of FIG. 29 according to one embodiment.
Figure 38:
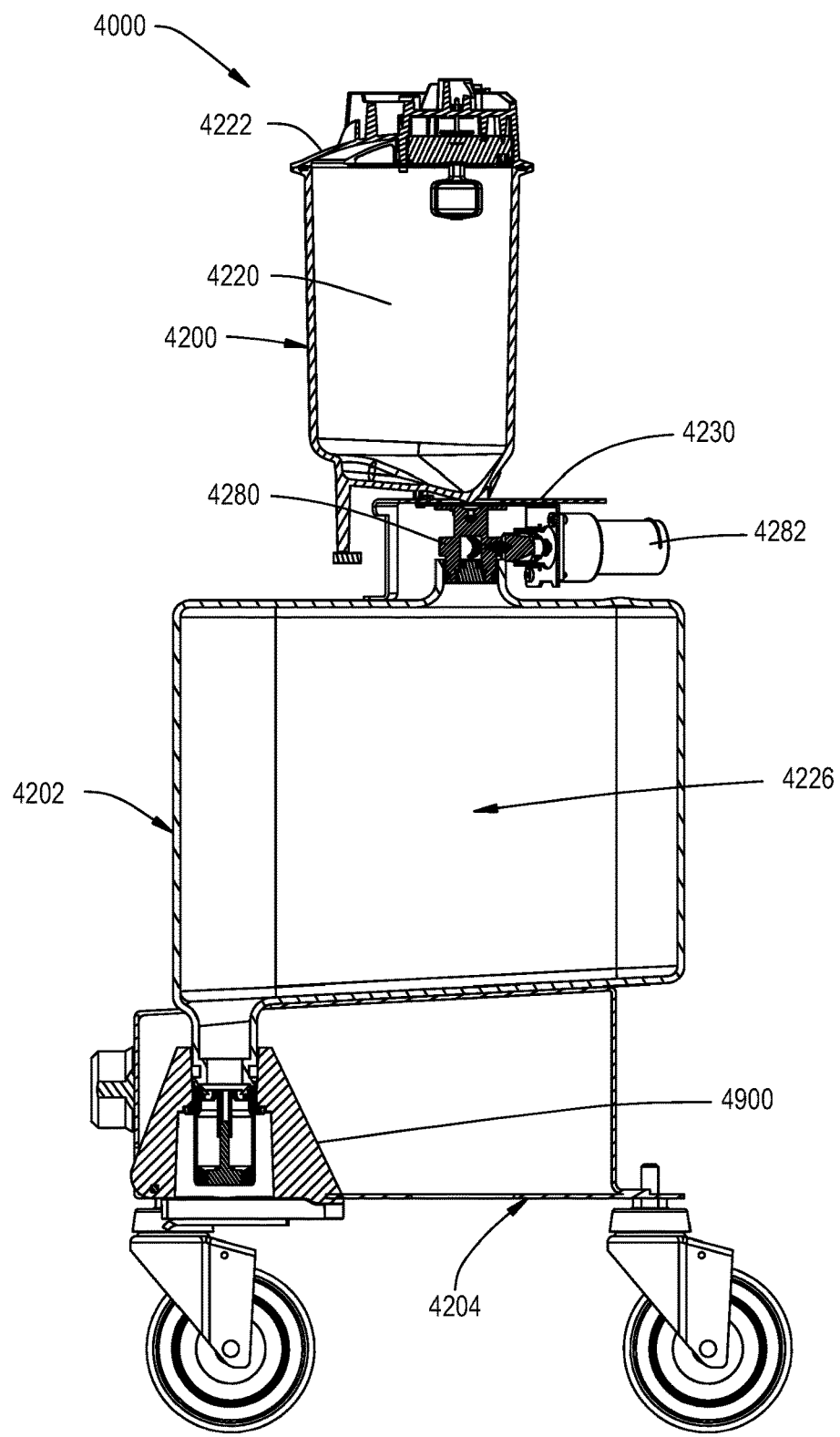
FIG. 38 is a cross-sectional view of the mobile rover of FIG. 37.

Turning now to FIGS. 29 and 37, details of mobile rover 4000 are illustrated. Waste collection system 3000 includes a mobile rover 4000 that is mated to and disconnected from mobile chassis 3100. Mobile rover 4000 utilizes an upper 4200 waste container and a lower storage tank 4202 to collect and temporarily store medical/surgical waste during use.

A frame 4204 supports the lower storage tank 4202 which in turn supports the upper waste container 4200. Upper waste container 4200 is mounted above storage tank 4202 such that waste material in the upper container 4200 can be emptied into the lower storage tank 4202 via gravity. While an upper waste container 4200 and a storage tank 4202 are shown in FIG. 29, in some embodiments, mobile rover 4000 can include only one of either waste container 4200 or storage tank 4202.

The frame 4204 includes a planar rectangular shaped base 4206 and a U-shaped support member 4208. The components of frame 4204 can be formed from metals such as steel. The base 4206 includes a top surface 4207 and a bottom surface 4209. The support member 4208 is mounted to the frame top surface 4207 by welding or by fasteners. U-shaped support member 4208 and frame top surface 4207 define a passage 4210. The lower storage tank 4202 has a bottom surface that is affixed to support member 4208. Four wheels 4212 are mounted to the bottom 4209 of base 4206 to allow rolling movement of mobile rover 4000.

Figure 27:
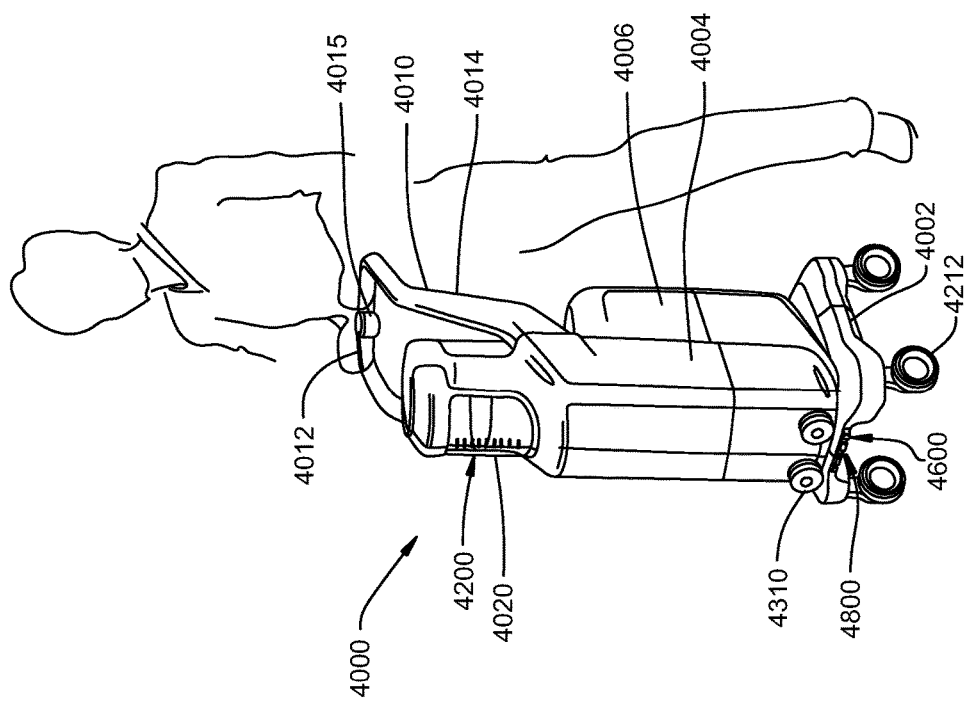
FIG. 27 is a front perspective view of another alternative embodiment of a mobile rover used with the chassis of FIG. 26.

With additional reference to FIG. 27, the frame base 4206 is covered by a cover 4002. A front cover 4004 is mounted over the front of upper waste container 4200 and lower storage tank 4202 and a rear cover 4006 is mounted over the rear of upper waste container 4200 and storage tank 4202. A handle 4010 has a grasp bar 4012 and arms 4014 that are attached to storage tank 4202. A release button 4015 is mounted to grasp bar 4012. Button 4015 deactivates the electromagnet 3160 (FIG. 26) that retains mobile rover 4000 to chassis 3100. Medical personnel can use handle 4010 to position mobile rover 4000 by pushing or pulling. A transparent window 4020 is formed in front cover 4004 allowing a user to visually check the contents of upper waste container 4200.

Covers 4002, 4004, 4006 and handle 4010 can be formed from molded plastic and attached to frame 4204 and waste containers 4200 and 4202 by suitable methods such as through the use of fasteners. Covers 4002, 4004 and 4006 are used to protect the internal components of mobile rover 4000 and to provide improved visual aesthetics.

Referring specifically to FIG. 37, the upper waste container 4200 comprises an upper canister 4218 that is slightly frusto-conical in shape, but appears cylindrical. The upper canister 4218 defines an upper waste chamber 4220 for collecting and holding medical/surgical waste. A cover or cap 4222 covers the upper canister 4218 closing upper waste chamber 4220. A lower storage tank 4202 includes waste container 4224 that is generally cube shaped. Waste container 4224 defines a lower waste chamber 4226 for holding waste material. The lower waste container 4224 has a top surface 4227, bottom surface 4228 and four side surfaces 4229.

Storage tank 4202 is not used to collect fluid waste. Storage tank 4202 is used to store fluid waste. The storage tank 4202 has a relatively large interior volume, between approximately 30 and 100 liters. The upper canister 4218 has a smaller volume, between approximately 3 and 10 liters. Canister 4218 and cap 4222 can be formed from molded plastic at least a portion of which is transparent. The storage tank 4202 can be formed from roto-molded or blow molded plastic materials.

A support structure 4230 is attached to storage tank top surface 4227 by fasteners (not shown). Support structure 4230 has four downwardly extending legs 4232 that are mounted to top surface 4227. Upper canister 4218 is mounted to support structure 4230 by fasteners (not shown). The upper canister 4218 is spaced above and from storage tank 4202 by the length of legs 4232. The support structure 4230 holds the upper waste container 4200 above the storage tank 4202.

A mobile rover upper waste coupler 4700 is mounted to cap 4222 and extends perpendicular upwards from cap 4222. An elbow fitting 4498 is mounted and retained to cap 4222. The elbow fitting 4498 is in fluid communication with upper waste chamber 4220. One end of vacuum hose 4496 is connected to elbow fitting 4498 and the other end of vacuum hose 4496 is connected to mobile rover suction or vacuum coupler 4600 (FIG. 28). Vacuum hose 4496 connects upper waste chamber 4420 to one of mobile rover vacuum couplers 4600 and provides a fluid communication path between the upper waste container 4200 and mobile rover vacuum coupler 4600.

Another elbow fitting 4512 is mounted through an opening 4508 in storage tank top surface 4227 and is in fluid communication with lower waste chamber 4226. One end of vacuum hose 4510 is connected to elbow fitting 4512 and the other end of vacuum hose 4510 is connected to mobile rover vacuum coupler 4600 (FIG. 28). Vacuum hose 4512 connects the lower waste container 4224 to one of mobile rover vacuum couplers 4600 and provides a fluid communication path between storage tank 4202 and mobile rover vacuum coupler 4600.

Figure 39:
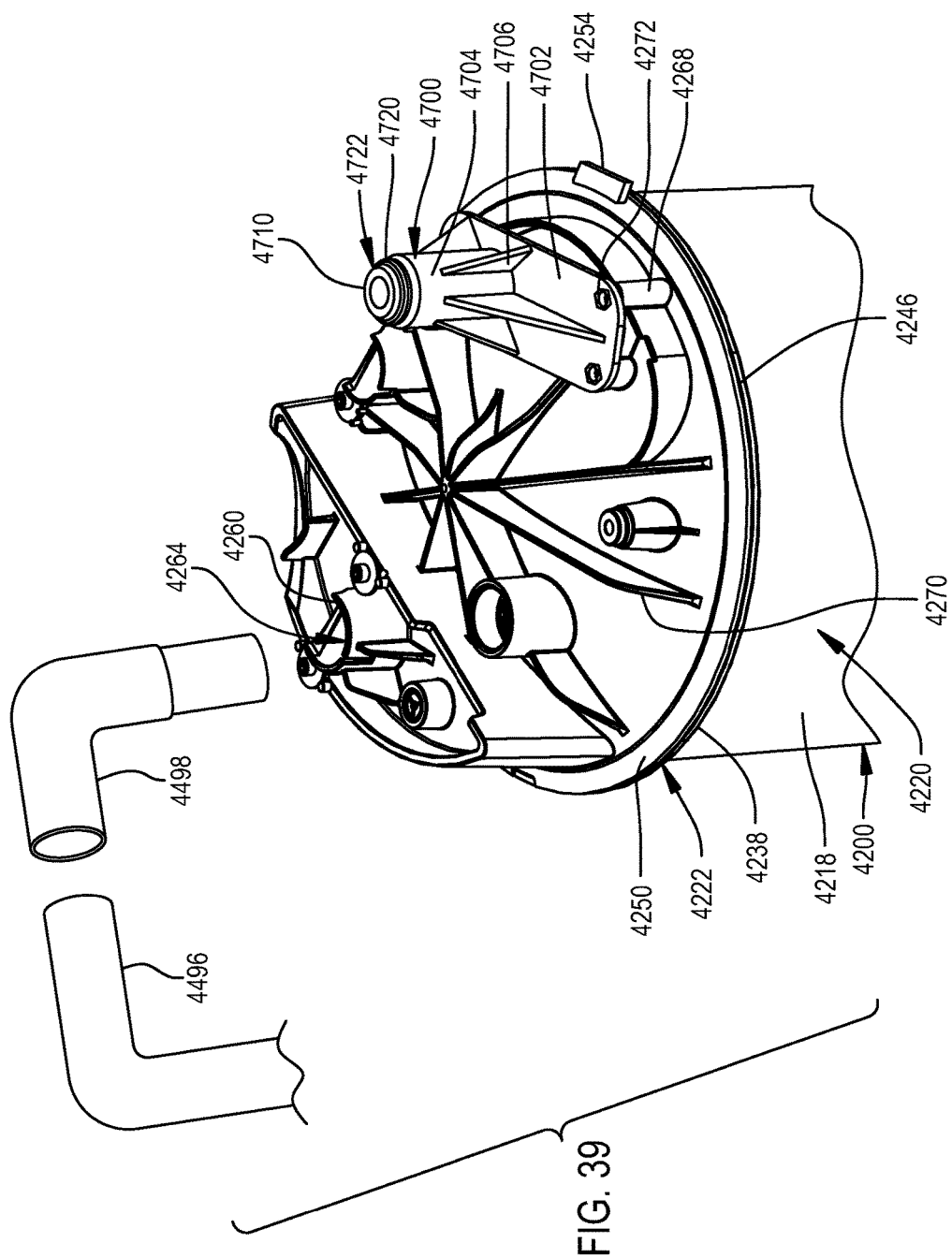
FIG. 39 is an enlarged perspective view of a canister cap.
Figure 40:
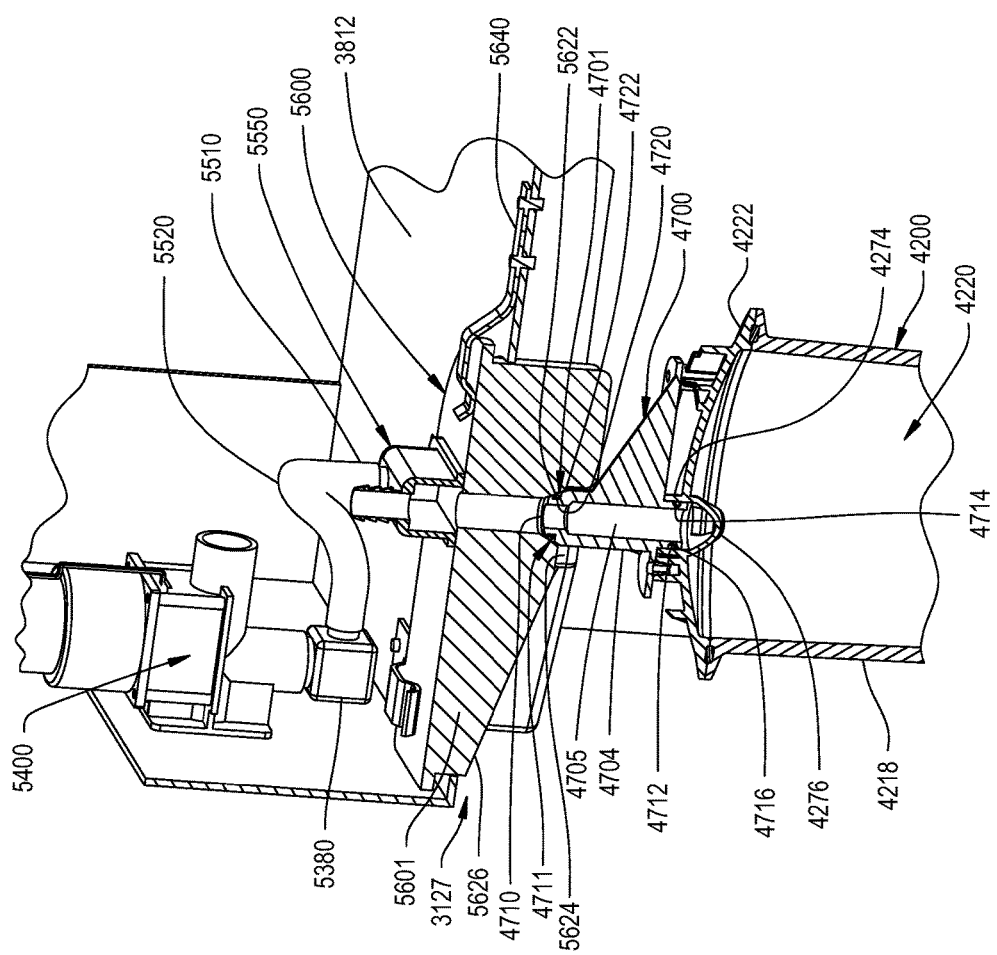
FIG. 40 is an enlarged cross-sectional view of the chassis waste coupler mated with the corresponding mobile rover upper waste coupler.

FIGS. 39 and 40 illustrate details of cap 4222 and mobile rover upper waste coupler 4700. Referring to FIGS. 39 and 40, cap 4222, is generally dome-shaped with a peripheral lip 4250 that engages a rim 4238 of the canister 4218 with a elastomeric seal 4246 trapped there between. A V-clamp 4254 secures the cap 4222 to canister 4218 by clamping the peripheral lips 4250 to the rim 4238.

The cap 4222 has an upwardly projecting boss 4260. A vacuum port or conduit 4264 is defined through boss 4260 and cap 4222 into the upper waste chamber 4220. A ninety degree elbow joint 4498 is mounted into the vacuum port 4264. The elbow joint 4498 has one end connected to the vacuum port 4264 and the other end connected to vacuum hose 4496. One end of elbow joint 4498 can be press fit into vacuum port 4264 and the other end press fit into vacuum hose 4496. The other end of vacuum hose 4496 is connected to rover vacuum coupler 4600.

Several mounting features 4268 and webs 4270 are formed on the top outer surface of cap 4222. The webs 4270 add rigidity and strength to cap 4222. The mobile rover upper waste coupler 4700 is mounted to mounting features 4268 using fasteners 4272. Mobile rover upper waste coupler 4700 has a planar base 4702 and a cylindrical waste conduit 4704 that is perpendicular to base 4702. A bore 4705 extends through waste conduit 4704. Several gussets 4706 are formed between the base 4702 and the conduit 4704 to add structural rigidity to the upper waste coupler 4700. The waste conduit 4704 functions as a waste fluid communications path from the chassis waste coupler 5600 into the mobile rover upper waste container 4200.

The waste conduit 4704 further includes opposed ends 4710 and 4712. An annular groove 4714 is defined in an outer surface of waste conduit 4704 adjacent to end 4712 and contains a rubber seal 4716. The end 4712 is received by an annular sleeve 4274 formed on cap 4222. The sleeve 4274 has a thru bore that extends into waste chamber 4220.

A vacuum seal is formed by seal 4716 between the inner surface of sleeve 4274 and the outer surface of waste conduit 4704. An Outlet 4276 extends downwardly from the bottom surface of cap 4222 and is formed as part of the cap 4222. The outlet 4276 is in fluid communication with waste conduit 4704. The outlet 4276 directs the flow of waste material away from a center axis of the waste canister 4218 toward the outer wall of the canister.

The waste conduit end 4710 is tapered and has an annular groove 4720 that is defined in an outer surface of the waste conduit adjacent to end 4710. A rubber seal 4722 is mounted in groove 4720. When the mobile rover 4000 is mated with the chassis 3100, waste conduit 4704 is received by waste coupler 5600.

Specifically, the waste conduit end 4710 slides over the waste coupler angled surface 5626 until the waste conduit end 4710 enters recess 5624 and slides into beveled counter bore 5622. The rubber seal 4722 forms a vacuum seal 4701 between the inner surface 5623 of the beveled counter bore 5622 and the outer surface of waste conduit 4704 at end 4710. The compression of seal 4722 between the inner surface 5623 and the outer surface of waste conduit 4704 substantially eliminates loss of suction between the rover upper waste coupler 4700 and the chassis waste coupler 5600.

Returning to FIGS. 28 and 29, a transfer valve 4280 is disposed between the upper waste container 4200 and storage tank 4202 to facilitate emptying of the waste material from the upper waste container 4200 to the storage tank 4202 via gravity. The transfer valve 4280 can be selectively closed to seal the vacuum path between the upper waste container 4200 and storage tank 4202 to allow independent vacuum regulation. In the open position, waste material present in the upper waste container 4200 drains, under the force of gravity, to storage tank 4202. In the closed position, waste material is retained in the upper waste container 4200. In one embodiment, a low level of vacuum can be drawn by storage tank 4202 to assist with drainage of waste material from upper waste container 4200 into storage tank 4202. The transfer valve 4280 can be a ball valve. Transfer valve 4280 allows mobile rover 4000 to hold a larger quantity of waste and be used during several medical procedures before emptying is required.

Transfer valve 4280 is moved by a transfer valve actuator or motor 4282. Transfer valve motor 4282 is coupled to the transfer valve 4280 to move the transfer valve 4280 between an open position in which fluid communication occurs between upper waste container 4200 and storage tank 4202 and a closed position in which fluid communication between upper waste container 4200 and storage tank 4202 is blocked. Transfer valve 4280 and transfer valve motor 4282 are both mounted between the top of storage tank 4202 and support structure 4230.

Pressure sensor 1698 is in fluid communication with suction fluid communication path 3070 in order to measure the level of vacuum drawn on the suction fluid communication path 3070 and by extension container 4200. Pressure sensor 1698 generates a pressure signal that corresponds to the vacuum level in suction fluid communication path 3070. Similarly, another pressure sensor 1699 is in fluid communication with suction fluid communication path 3072 in order to measure the level of vacuum drawn on the suction fluid communication path 3072 and by extension container 4202. Pressure sensor 1699 generates a pressure signal that corresponds to the vacuum level in suction fluid communication path 3072. While pressure sensors 1698 and 1699 are shown mounted between containers 4200, 4202 and couplers 4600, pressure sensors 1698 and 1699 can be mounted anywhere in their respective suction fluid communication paths 3070, 3072 downstream of vacuum regulators 3222 and 3224. In one embodiment, pressure sensor 1698 is mounted in container 4200 and pressure sensor 1699 is mounted in container 4202. In another embodiment, pressure sensors 1698 and 1699 are mounted in chassis cart 3100 downstream of vacuum regulators 3222 and 3224.

Figure 41:
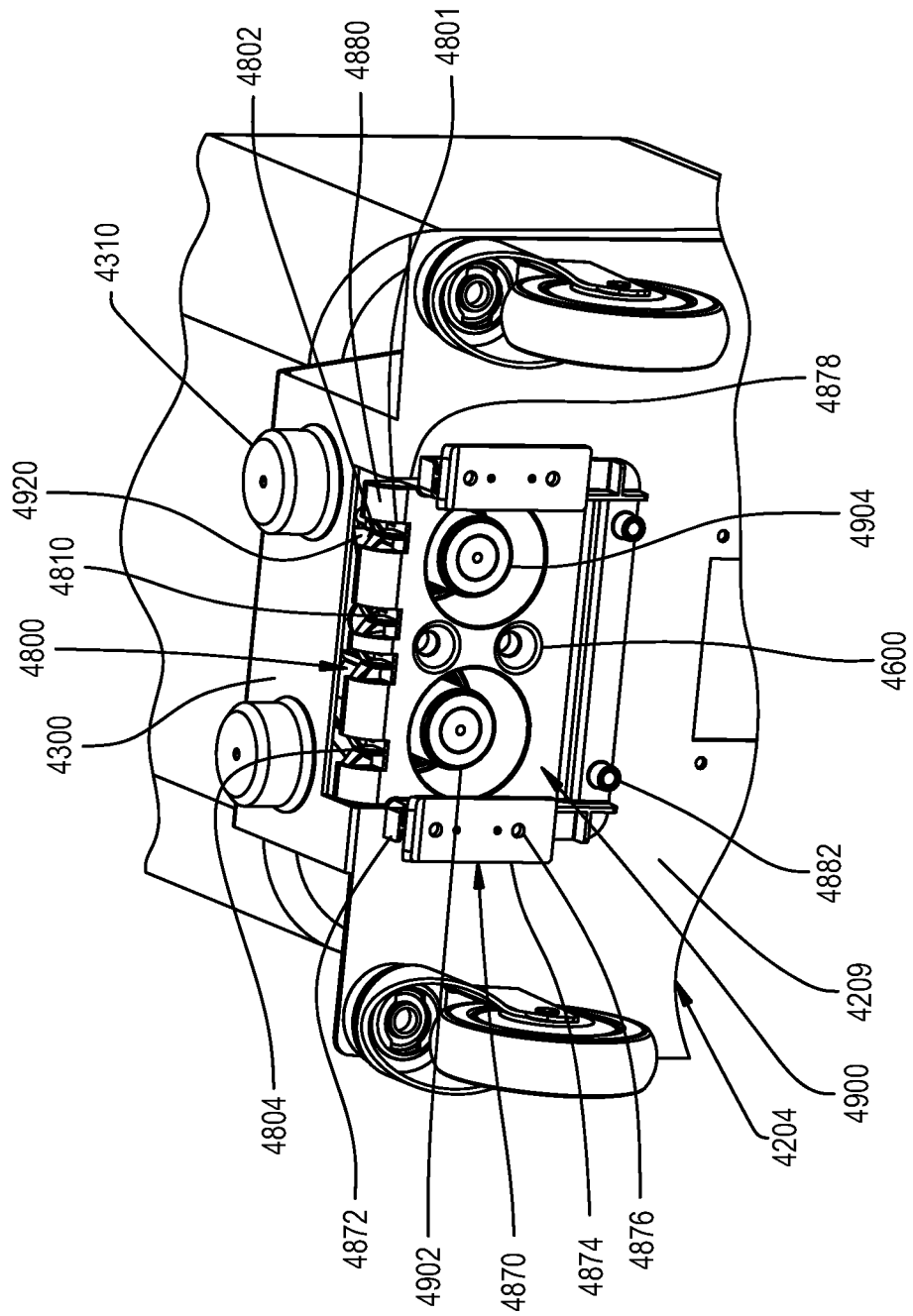
FIG. 41 is an enlarged perspective view of the bottom of the mobile rover of FIG. 37.
Figure 42:
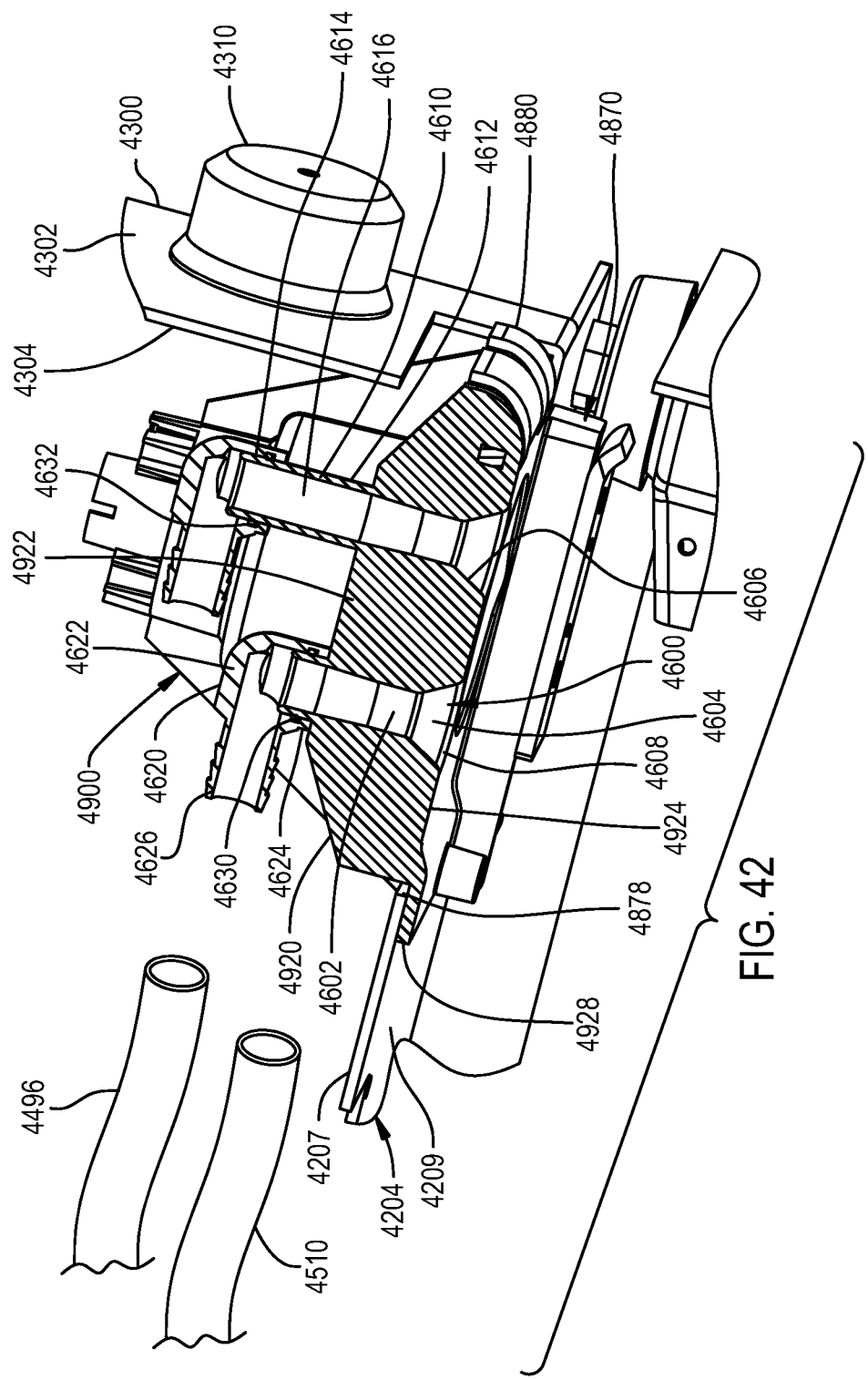
FIG. 42 is an enlarged cross-sectional view of the mobile rover vacuum coupler.

With reference to FIGS. 41 and 42, mobile rover 4000 includes a guide apparatus 4870 that is adapted to guide floating coupler mechanism 3300 (FIG. 26) into the guide apparatus 4870 when mobile rover 4000 is mated with chassis 3100. The guide apparatus 4870 is mounted to the bottom surface 4209 of mobile rover frame 4204. Guide apparatus 4870 comprises a spaced apart pair of elongated guide rails 4872 and a pair of guide plates 4874. The guide rails 4872 are formed integral with water and drain manifold 4900. Guide plates 4874 are coupled to the integral guide rails 4872 by fasteners 4876. Fasteners 4876 also attach water and drain manifold 4900 to frame 4204. The guide rails 4872 and guide plates 4874 are located on opposite sides of an opening 4878 in frame 4204. Opening 4878 is located toward a proximal edge of frame 4204. The guide rails 4872 have rounded ends that extend away from the center axis of frame 4204 and the guide plates 4874 have rounded edges. Guide rails 4872 are oriented generally perpendicular to the frame bottom surface 4209 and guide plates 4872 are mounted perpendicular to the guide rails 4872.

The guide apparatus 4870 further includes four rounded guide shoulders 4880 that extend upwardly from the proximal edge of frame 4204 adjacent opening 4878 and between guide rails 4872.

The guide rails 4872 are formed with a proximal directed opening angle to each other such that the distance between the ends of guide rails 4872 adjacent to shoulder 4880 is greater than the distance between the ends of guide rails 4872 adjacent to posts 4882. The guide plates 4874 are mounted at an angle to the frame bottom surface 1209. The proximal ends of guide plates 4874 toward shoulder 4880 are positioned lower than the distal ends of the guide plates 4874.

A vacuum and drain manifold 4900 is mounted to frame 4204 over opening 4878. The vacuum and drain manifold 4900 includes a lower waste drain coupling or waste drain port 4902, a water coupling or port 4904 and two vacuum couplings 4600 all of which face in a downward direction from the manifold 4900 into the opening 4878. The vacuum and drain manifold 4900 is mounted to frame 4204 using fasteners (not shown). Vacuum couplings 4600 are also used as guide pin receptacles when mobile rover 4000 is docked to static docker 900 (FIG. 4). The waste drain port 4902 and water port 4904 are connected to the static docker 900 in order to facilitate the emptying of waste and cleaning of upper waste container 4200 and storage tank 4202 (FIG. 37).

Continuing to refer to FIGS. 41 and 42, details of rover vacuum coupling 4600 are shown. Rover vacuum coupling 4600 mates with chassis vacuum coupling 3400 (FIG. 32) when mobile rover 4000 is mated with chassis 3100. Vacuum and drain manifold 4900 has a generally rectangular shaped housing 4920 that is mounted to frame 4204 over opening 4878. Housing 4920 has a top surface 4922, a bottom surface 4924 and a rounded proximal facing 4880. The housing 4920 also has a peripheral lip 4928 that extends from three sides of housing 4920 through opening 4878 and rests in contact with the frame bottom surface 4209.

Rover vacuum coupling 4600 is defined by a bore 4602 that extends through housing 4920 and a beveled counter bore 4604 that extends from housing bottom surface 4924 into housing 4920 approximately one third the thickness of housing 4920. The beveled counter bore 4604 is defined by a downward facing truncated cone shaped surface 4606. A circular opening 4608 is defined where surface 4606 intersects housing bottom surface 4924.

The rover vacuum coupling 4600 further includes two cylindrical conduits 4610 that extend perpendicularly away from the housing top surface 4922. The conduits 4610 can be integrally formed with housing 4920. Conduits 4610 each have an end 4612 that is attached to housing top surface 4922, an opposed end 4614 and a bore 4616 that is continuous with bore 4602.

A ninety degree elbow fitting 4620 is attached to each conduit end 4614. Each elbow fitting 4620 has a central body 4622, a downward facing end 4624 and a distal facing barbed end 4626. One elbow fitting barbed end 4626 receives the end of vacuum hose 4496 and the other elbow fitting barbed end 4626 receives the end of vacuum hose 4510. An annular groove 4630 is defined on the interior surface of the fitting end 4624. A rubber seal 4632 is seated in the annular groove 4630. The elbow fitting end 4624 is press fit over conduit end 4614 such that rubber the rubber seal 4632 is compressed between the outer surface of conduit 4610 and the inner surface of elbow fitting end 4624 forming a vacuum seal.

A mobile rover power and data coupler 4800 is shown in FIGS. 37 and 41. Rover power and data coupler 4800 receives low voltage electrical power and data from chassis power and data coupler 3500 (FIG. 31) when mobile rover 4000 is mated with chassis 3100. This electric power is used by various systems of the mobile rover 4000. The power and data coupler 4800 passes control (e.g. via release button 4015) and measurement information (e.g. via level sensor 4962) between the rover and mobile chassis. Rover power and data coupler 4800 receives electrical power via electrical contacts from chassis 3100 to mobile rover 4000.

Four slots 4801 are defined between the four frame shoulders 4880. Blade receptacles 4802, 4804 and 4810 are mounted to a proximal portion of the vacuum and drain housing 4920. The blade receptacles 4802, 4804 and 4810 are positioned adjacent and face into slots 4801 and can be accessed through slots 4801. The blade receptacles 4802, 4804 and 4810 are bifurcated and spring loaded. The blade contacts 3502, 3504 and 3510 (FIG. 31) slide into and are grasped by the blade receptacles 4802, 4804 and 4810, respectively.

More specifically, a power receptacle 4802 mates with the power contact 3502 to provide a positive electrical potential to mobile rover 4000. A ground receptacle 4804 mates with the ground contact 3504 to provide ground electrical potential to mobile rover 4000. Data receptacles 4810 mate with the data contacts 3510 to facilitate data communications between the mobile rover 4000 and chassis 3100. The receptacles 4802, 4804 and 4810 are formed from a conductive metal such as a copper alloy and may be plated to withstand arcing and prevent corrosion.

Turning to FIG. 42, a planar rectangular shaped mounting plate 4300 extends perpendicularly upwards from the top surface 4207 of frame 4204. The mounting plate 4300 is formed from metal and is attached to frame 4204. The mounting plate 4300 includes a proximal facing surface 4302 and a distal facing surface 4304. Two cylindrical shaped drums 4310 are mounted to the proximal surface 4302 and also face in a proximal direction. The drums 4310 are formed from a material that is attracted to a magnetic field such as steel. When the mobile rover 4000 is mated with the chassis 3100, the drums 4310 face into receptacle 3124 (FIG. 26), are attracted to and are drawn into contact with the electromagnet 3160 (FIG. 26) when the electromagnet 3160 is energized. When energized, electromagnets 3160 hold mobile rover 4000 to chassis 3100.

C. Static Docker

Figure 43:
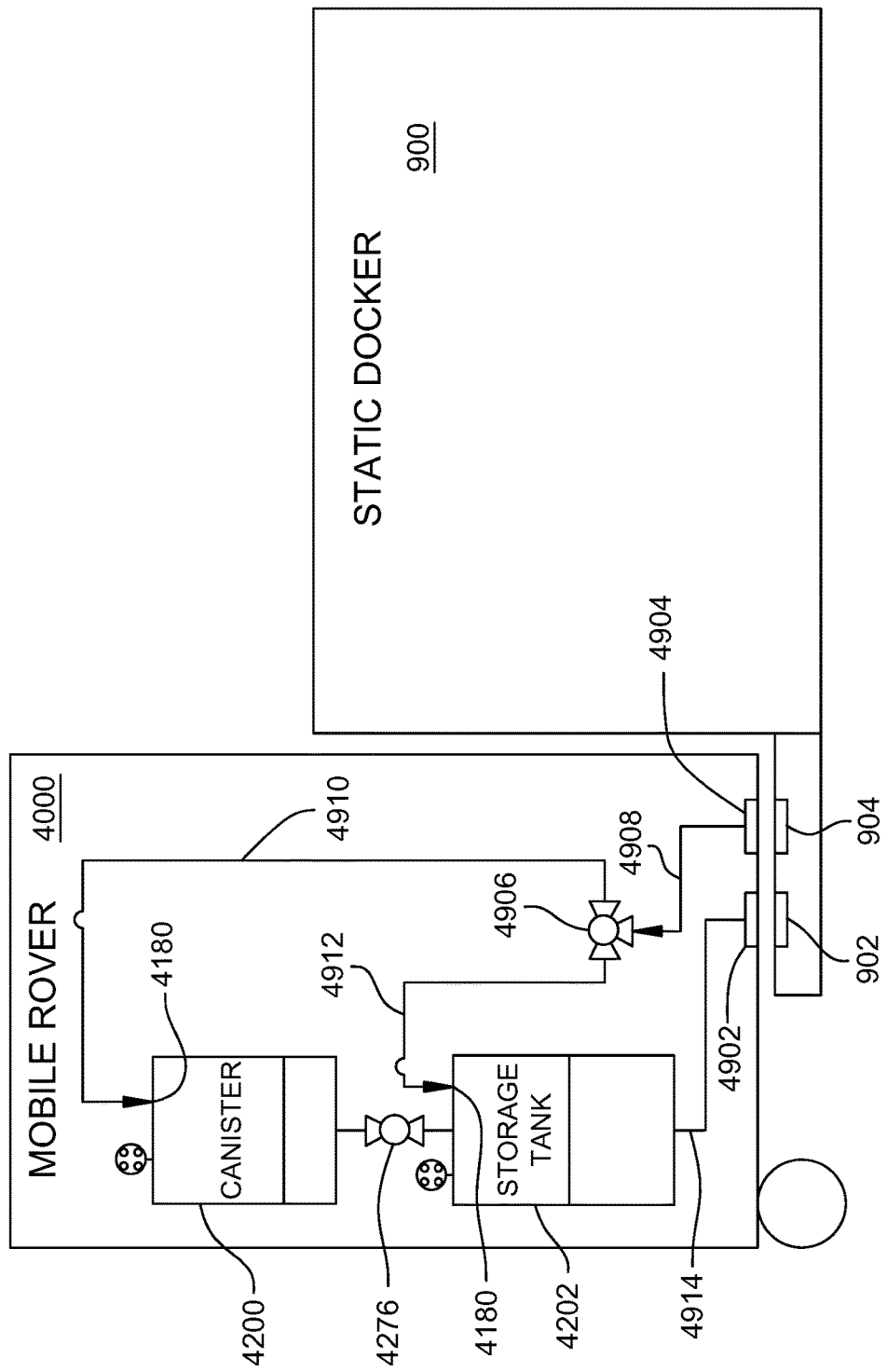
FIG. 43 is a diagrammatic view of the water and drain fluid communication paths according to one embodiment.

With reference to FIG. 43, a water and drainage diagram of the mobile rover 4000 docked with the static docker 900 is illustrated. The mobile rover 4000 is emptied of accumulated medical/surgical waste and cleaned while docked with static docker 900. The static docker 900 includes waste port 902 and water port 904. Waste port 902 and water port 904 are coupled with respective waste port 4902 and water port 4904 of mobile rover 4000.

Water port 4904 is connected to a diverter valve 4906 through water line 4908. Diverter valve 4906 regulates the flow of water and cleaning fluids to respective waste containers 4200 and 4202. A water line 4910 connects the diverter valve 4906 to the sprinkler head 4180 in upper waste container 4200. A water line 4912 connects the diverter valve 4906 to the sprinkler head 4180 in storage tank 4202. The waste port 4902 is connected to the bottom of storage tank 4202 by a spout 4914.

After the mobile rover 4000 has been docked with static docker 900, the storage tank 4202 is emptied of accumulated waste by the static docker 900. The transfer valve 4276 is in an open position during the emptying operation such that any waste in the upper waste container 4200 flows into the storage tank 4202. After the storage tank 4202 is empty, the upper waste container 4200 and the storage tank 4202 are cleaned by cleaning fluids pumped by static docker 900 through water port 4904, water line 4908, diverter valve 4906, water lines 4910, 4912 and sprinkler heads 4180 into the respective waste container 4200 and storage tank 4202. The accumulated cleaning fluids are emptied through waste port 4902.

D. Power and Control System

FIG. 44 illustrates a schematic diagram of a power and control system 4980 for providing electrical power and controlling the operation of the chassis 3100 and mobile rover 4000. The components of power and control system 4980 are mounted within the chassis 3100 and mobile rover 4000. A power cord 3154 extends from the mobile chassis 3100 terminating in power plug 3156. The power plug 3156 is connected to an electrical receptacle in the medical facility to facilitate connection to a utility power system.

The power cord 3154 and power plug 3156 are connected to a power supply 3804. Power supply 3804 can supply one or more voltage and current levels to mobile chassis 3100. The power supply 3804 supplies power to surgical modules 3140 through power cables 3152. The power supply 3804 also supplies power to chassis controller 3802 through a power cable 3153. A backup battery or ultra-capacitor 3805 is connected with power supply 3804 through a power cable 3806 to supply backup power to chassis 3100 in the event of a loss of primary power. A thermal management system 3808 is mounted within chassis 3100 near surgical modules 3140 and other electronic controls. The thermal management system 3808 includes cooling devices such as fans and sensors to detect heat levels. The thermal management system 3808 is connected with power supply 3804 through a power cable 3809.

A chassis controller 3802 comprises a controller or microprocessor and solid state switches for controlling the operation of components of chassis 3100. The controller 3802 is connected to the power and data coupler 3500 through a power cable 3810 and a data cable 3812. The power and data coupler 3500 transfers electrical power and data via electrical contacts to mobile rover 4000. Mobile rover 4000 includes a power and data coupler 4800 that is connected to a mobile rover controller 4952 through a power cable 4954 and a data cable 4956. Electric power and data is transferred through the mating of respective contacts and receptacles in the power and data couplers 4500 and 4800.

When the mobile rover 4000 is docked with the static docker 900 (FIG. 4), the rover power and data coupler 4800 allows the static docker 900 to supply power to and communicate with mobile rover 4000 during the waste emptying and cleaning procedures.

With additional reference to FIGS. 26 and 27, controller 3802 is further connected to electromagnets 3160 via a power cable 3814. Electromagnets 3160 are mounted to chassis 3100 and face towards receptacle 3124. When the mobile rover 4000 is mated with the chassis 3100, the steel drums 4310 are brought into close physical proximity to the electromagnet 3160. When the rover 4000 is mated with chassis 3100 and power is initially provided to rover 4000, controller 4952 automatically sends an electrical signal through couplers 4800 and 3500 to controller 3802 instructing controller 3802 to energize or turn on electromagnets 3160. When the electromagnets 3160 are energized, a magnetic field is created that draws the steel drums 4310 into contact with electromagnet 3160 and thereby retains the mobile rover 4000 to the chassis 3100.

A release button 4015 is mounted to mobile rover 4000 and is connected to the controller 4952. When a user depresses the release button 4015, controller 4952 sends an electrical signal through the couplers 4800 and 3500 to controller 3802 directing controller 3802 to de-energize electromagnet 3160. When electromagnet 3160 is de-energized, the magnetic field is removed, thereby releasing the mobile rover 4000 from chassis 3100.

Referring to FIG. 44, the controller 3802 is also in communication with a control valve actuator 5430 through a power and data cable 5440. The controller 3802 can selectively open and close or partially open any of the control valves 5400 using actuator 5430. The controller 3802 is in communication with vacuum pump 3210 via a power and data cable 3820. The controller 3802 controls the operation of vacuum pump 3210. The controller 3802 is in communication with a HEPA filter memory device 3822 via a power and data cable 3824. The controller 3802 can receive a signal from HEPA filter memory device 3822 indicating that the filter requires changing.

The controller 3802 is also in communication with vacuum regulator 3222 via a power and data cable 3826 and is in communication with vacuum regulator 3224 via a power and data cable 3828. Controller 3802 controls the operation of vacuum the regulators 3222 and 3224 in order to independently regulate the vacuum level supplied to upper waste container 4200 and storage tank 4202.

Controller 3802 is further in communication with a radio frequency identification device (RFID) reader 3830 via a power and data cable 3832. The RFID reader 3830 reads information from RFID tags placed on various pieces of medical equipment and conveys the information to controller 3802. In one embodiment, RFID tags are placed on surgical handpieces 62, 66 (FIG. 2) such that controller 3802 recognizes the type of handpiece 62, 66 being used and determines one or more operating parameters for the mobile rover 4000 and chassis 3100.

The controller 3802 is also in communication with chassis control panel 3162 via a power and data cable 3834. A user can view parameters and control settings and the operation of the chassis 3100 and mobile rover 4000 using control panel 3162. The controller 3802 is additionally in communication with the surgical modules or instruments 3140 through data cables or bus 3168. Controller 3802 can receive data from the memory 3143 integral with the instruments 3140 to control the vacuum regulators 3222, 3224 so as to establish the level of suction drawn on the containers 4200, 4202 of the container cart 4000. The controller 3802 receives the data from instrument 3140 memory and sets the level of suction drawn on the containers 4200, 4202 based on the data read from the memory of the instrument 3140.

Controller 3802 is further in communication with LED lights 3966 through a power cable 3968 and with LED lights 3970 through a power cable 3972. When the mobile rover 4000 is mated with the chassis 3100, the LED lights 3966 mounted to chassis 3100 are positioned adjacent to upper waste container 4202 and the LED lights 3970 mounted to chassis 3100 are positioned adjacent to storage tank 4202. The controller 3802 turns LED lights 3966 and 3970 on and off in order to backlight the upper waste container 4200 and storage tank 4202.

The mobile rover controller 4952 is further in communication with the release button 4015 through a power and data cable 4960. The controller 4952 is in communication with a waste container and storage tank level sensor 4962 through a power and data cable 4964. The level sensor 4962 generates electrical signals that are representative of the level of waste in the upper waste container 4200 and the storage tank 4202. Controller 4952 is also in communication with the transfer valve actuator 4282 through a power and data cable 4966. The controller 4952 can open and close or partially open transfer valve 4280 using actuator 4282 to selectively control the flow of waste from upper waste container 4200 into storage tank 4202. Controller 4952 is additionally in communication with a diverter valve actuator 4907 through a power and data cable 4970. The controller 4952 can open and close diverter valve 4906 using the actuator 4907 to selectively control the flow of water to upper waste container 4200 and storage tank 4202.

Controller 4952 is in communication with pressure sensor 1698 through a data cable 1967. Data cable 1967 carries the pressure signal sensor 1698 to controller 4952. Data cable 1971 carries the pressure signal from sensor 1699 to controller 4952. The pressure signals are relayed from rover controller 4952 via communication circuits 1856 and 620 to chassis controller 3802. Chassis controller 3802 regulates the vacuum drawn on containers 4200, 4202 based at least partially on the pressure sensor signals. In one embodiment, controller 3802 controls the operation of the vacuum regulators 3222 and 3224 based on the pressure sensor signals to independently regulate the vacuum level supplied to each of waste containers 4200 and 4202.

E. Operation of the Second Embodiment

Referring to FIGS. 26-28, the medical/surgical waste collection system 3000 is prepared for use in the collection of medical/surgical waste. The chassis 3100 is located in an operating room/surgical area during use. Power plug 3156 is connected to a power source to supply power to chassis 3100. The chassis 3100 is turned on by an operator using control panel 3162.

With additional reference to FIGS. 31 and 41, an empty mobile rover 4000 is mated with chassis 3100 by a user moving the mobile rover 4000 into chassis receptacle or void space 3124. As the mobile rover 4000 is moved into void space 3124, the guide apparatus 4870 engages the floating coupler mechanism 3300. Specifically, as the mobile rover 4000 is moved towards chassis 3100, the rover angled guide rails 4872 engage the chassis angled sections 3322 and the rover angled guide plates 4874 engage the chassis lip 3324 causing the rover guide mechanism 4870 and chassis floating coupler mechanism 3300 to move into a centered position with respect to each other. At the same time, the chassis floating coupler mechanism 3300, through spring bracket 3302, can slightly move or float allowing the chassis vacuum coupler 3400 and the chassis power and data coupler 3500 to move slightly up or down in order to more easily be aligned with the respective rover vacuum coupler 4600 and rover power and data coupler 4800.

Eventually, the rover power and data coupler 4800 will engage and contact the chassis power and data coupler 3400 and steel drums 4310 will contact electromagnet 3160 limiting the forward movement of mobile rover 4000. In this position, the rover power and data coupler 4800 is engaged with the chassis power and data coupler 3500 such that the rover receptacles 4802, 4804 and 4810 are mated with respective chassis contacts 3502, 3504 and 3510. The chassis power and data coupler 3400 thereby provides electrical power to mobile rover 4000.

With additional reference to FIG. 44, after power is supplied to mobile rover 4000, the chassis controller 3802 begins data communication with the rover controller 4952 through data contacts 3510 and receptacles 4810. Controllers 3802 and 4952 initiate a start up sequence to prepare the waste collection system 3000 for operation. With the mobile rover 4000 fully seated in chassis void space 3124, controllers 3802 and 4952 can sense that the rover 4000 is mated with the chassis 3100 and automatically energize electromagnet 3160. When chassis electromagnet 3160 is energized, it attracts the rover steel drums 4310 such that steel drums 4310 are drawn into contact with electromagnet 3160. Continued energizing of electromagnet 3160 retains the mobile rover 4000 to the chassis 3100.

Figure 45:
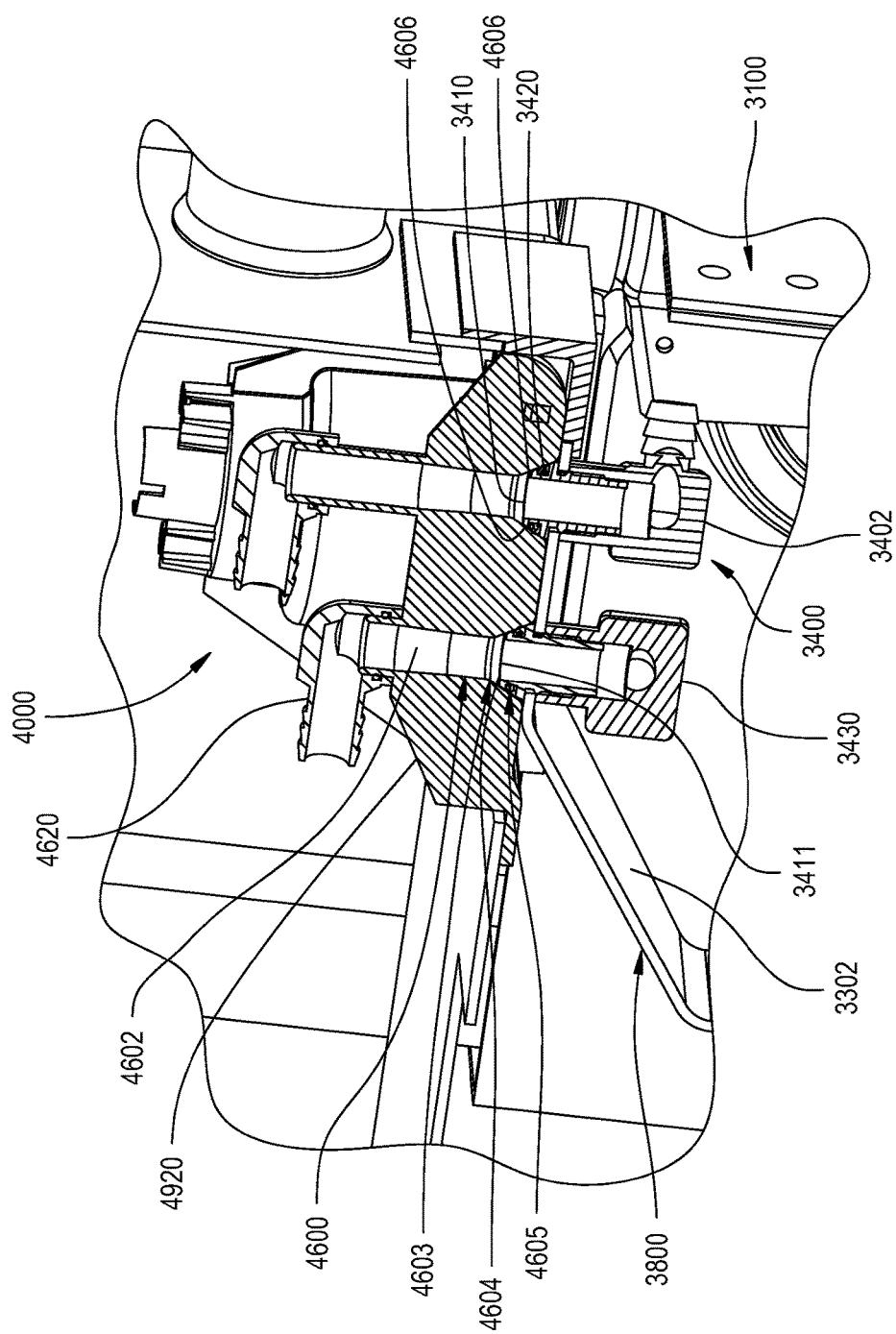
FIG. 45 is an enlarged cross-sectional view of the chassis vacuum coupler mated with the mobile rover vacuum coupler.

Referring specifically to FIGS. 32, 42 and 45, as mobile rover 4000 is mated with chassis 3100, the rover vacuum coupler 4600 engages and mates with the chassis vacuum coupler 3400. As the mobile rover 4000 is moved in a proximal direction into void space 3124, the bottom surface 4924 of rover housing 4920 contacts tapered end 3411 of chassis elbow fitting 3402 causing both of the elbow fittings 3402 and top plate 3304 to be pressed in a downward direction. The spring flex of spring bracket 3302 allows this downward movement.

Continued proximal movement of mobile rover 4000, causes the rover beveled counter bore 4604 to move into coaxial alignment and receive chassis tapered end 3411. The spring bracket 3302 urges fitting tapered end 3411 to move into the beveled counter bore 4604 such that seal 3420 is seated and compressed against cone shaped surface 4606. The compression of seal 3420 forms a vacuum seal 4605 with the cone shaped surface 4606 eliminating any loss of suction between the elbow fitting 3402 and the housing 4920. A continuous suction fluid communication path is defined through the rover vacuum coupler 4600 and the chassis vacuum coupler 3400 by bores 4616, 4602, 3414 and 3440. The cart components include the housing 4920 that receives the chassis mechanical couplers 3400 and forms a mechanical interlock that releasably holds the container cart 4000 and the suction cart 3100 together as a single unit. Specifically, the chassis vacuum coupler tapered end 3411 engages the housing counter bore 4604 forming a mechanical detent 4603 that releasably holds the container cart 4000 and suction cart 3100 together as a single unit.

Turning to FIGS. 36 and 40, as the mobile rover 4000 is mated with chassis 3100, the rover upper waste coupler 4700 also engages and mates with chassis waste coupler 5600. As mobile rover 4000 is moved in a proximal direction into void space 3124, the rover waste conduit 4704 is received by the chassis waste coupler 5600.

Specifically, with mobile rover 4000 moving in a proximal direction, the rover waste conduit tapered end 4710 slides into chassis opening 3127 and contacts the chassis angled surface 5626. The abutment of tapered end 4710 sliding against angled surface 5626 causes the waste coupler body 5601 to be urged upwards overcoming the downward bias generated by spring clips 5640. With continued movement in a proximal direction, the waste conduit tapered end 4710 will enter recess 5624 and then slide into the beveled counter bore 5622. The spring clips 5640 urge the waste coupler body 5601 to move in a downward direction such that the counter bore cone shaped surface 5623 is seated and compressed against seal 4722. The compression of seal 4722 forms a vacuum seal 4701 with the cone shaped surface 5623 eliminating any loss of suction between coupler body 5601 and waste conduit 4704. A continuous suction fluid communication path is defined through rover upper waste coupler 4700 and chassis waste coupler 5600 by bores 4705, 5620 and 5622. The cart components include the waste coupler body 5601 that receives the waste conduit 4704 and forms a mechanically interlock that releasably holds the container cart 4000 and the suction cart 3100 together as a single unit. Specifically, the conduit tapered end 4710 engages the body beveled counter bore 5622 forming another mechanical detent 4711 that releasably holds the container cart 4000 and the suction cart 3100 together as a single unit.

With reference to FIGS. 26, 27, 33A and 34, one or more new disposable inlet fittings 5100 are attached to one or more corresponding inlet fitting receivers 5200. A user grasps cap skirt 5158 and inserts barrel 5102 into the receiver bore 5212. Post 5210 is aligned with slot 5166 and the inlet fitting 5100 is moved in a proximal direction until barrel 5102 is seated in bore 5212. The barrel proximal end 5108 abuts valve body 5402 and distal end 5204 abuts the proximal face of flange 5156. Skirt 5158 and inlet fitting 5100 are then rotated clockwise such that post 5210 slips into recess 5168 thereby locking the inlet fitting 5100 to the inlet fitting receiver 5200.

One or more suction lines 62, 64 are connected to one or more of the disposable inlet fittings 5100. The control valves 5400 allow the suction or vacuum to each of the suction lines 60, 64 to be independently controlled. The control panel 3162 allows a user to selectively turn on and off or partially open each of control valves 5400. This allows the user to switch off suction to the suction lines at will, reducing noise in the operating room.

Because the suction lines 62, 64 are attached to the chassis 3100 via inlet fittings 5100, when mobile rover 4000 becomes full of waste, another empty mobile rover can be exchanged for the full mobile rover during the medical procedure without the need to disconnect the suction lines 62, 64 going to the surgical field. In addition, other cables and tubes (not shown) extending from surgical modules or equipment 3140 do not need to be disconnected when changing mobile rover 4000. This allows for quick replacement of a full mobile rover for an empty mobile rover and minimizes any interruption to surgical procedures where large volumes of fluid waste are collected.

In one embodiment, the operation of control valves 5400 are controlled by one or more medical/surgical instruments or modules 3140. This allows the medical/surgical instruments to work in cooperation with each other to improve performance. For example, an arthroscopy pump interacting with control valves connected to an outflow cannula could better control the flow of distending fluid into and out of a joint to minimize the volume of fluid used while maintaining visibility and joint distension pressure.

With further reference to FIGS. 28 and 44, the control panel 3162 allows a user to selectively turn on and off vacuum pump 3210 and to selectively change the amount of vacuum drawn using vacuum regulators 3222, 3224 within one or both of upper waste container 4200 or storage tank 4202.

The vacuum pump 3210 creates a continuous suction fluid communication path 3070 that is formed from the suction applicator 62 or 66 (FIG. 26) to the suction or vacuum pump 3210. When vacuum pump 3210 is activated, the resultant suction draws waste matter into the respective suction applicator 62 or 66 as selected by a user. Suction fluid communication path 3070 is sometimes called a vacuum path 3070.

With the vacuum pump 3210 in operation and the control valve 5400 in an open position, the waste stream associated with suction fluid communication path 3070 travels from the suction applicator 62 into suction line 60 through disposable inlet fitting 5100 through inlet fitting receiver 5200 through control valve 5400 and through elbow fitting 5380 (FIG. 40). With reference to FIG. 40, the suction fluid communication path 3070 continues through vacuum hose 5520, through fitting 5510, through manifold 5500, through chassis valve coupler body 5601, through rover waste conduit 4704 and exiting from outlet 4276 into upper waste container 4200 where the waste stream is deposited.

Turning to FIGS. 28, 37 and 45, from the upper waste container 4200, the suction fluid communication path 3070, now consisting primarily of air, travels into elbow fitting 4498 and vacuum hose 4496 through elbow fitting 4620 into bore 4602 of housing 4920 and elbow fitting 3402. From the elbow fitting 3402, the suction fluid communication path 3070 continues into vacuum hose 3444 (FIG. 32) through vacuum regulator 3222 (FIG. 28) into check valve 3226 through vacuum hose 3242 and HEPA filter 3232 into vacuum hose 3244 ending at vacuum pump 3210.

Turning to FIGS. 28, 37 and 45, from storage tank 4202, the suction fluid communication path 3072, consisting primarily of air, travels into elbow fitting 4512 and vacuum hose 4510 through elbow fitting 4620 into bore 4602 of housing 4920 and elbow fitting 3402. From elbow fitting 3402, the suction fluid communication path 3072 continues into vacuum hose 3444 (FIG. 32) through vacuum regulator 3222 (FIG. 28) into check valve 3226 through vacuum hose 3242 and HEPA filter 3232 into vacuum hose 3244 ending at vacuum pump 3210.

Liquid waste and small pieces of solid waste are deposited into upper waste container 4200. Once the upper waste container is full or is desired by a user to be emptied, a user can elect to transfer the waste into storage tank 4202 using transfer valve 4280. The waste is thereby stored until being emptied.

During the operation of waste collection system 3000, various operating states or parameters can be controlled by a user and waste collection system 3000 can alert a user to various operating conditions. In one embodiment, a user can elect to illuminate the contents of either waste container 4200 or storage tank 4202 using the control panel 3162 to turn light emitting diodes 3966 or 3970 (FIG. 44), respectively on. In another embodiment, the level sensor 4962 (FIG. 44) can detect when either upper waste container 4200 or storage tank 4202 is approaching being filled and can send a level sensor signal representative of an operating state of waste collection system 3000 to control panel 3162 to alert a user of this condition.

Medical personnel may also operate the surgical modules 3140 during or separate from the operation of waste collection system 3000 in order to perform various surgical functions.

After a period of time, when the upper waste container 4200 is being used, the upper waste container 4200 will become full and need to be emptied, or the operator may elect to empty the upper waste container before being filled. At this point, the user uses control panel 3162 to direct the transfer valve actuator 4282 (FIG. 44) to open the transfer valve 4280 (FIG. 44) and transfer waste material from the upper waste container 4200 to the storage tank 4202.

As shown in FIG. 28, vacuum pump 3210 also creates a continuous suction fluid communication path 3072 that is formed from the storage tank 4202 to the suction or vacuum pump 3210. Suction fluid communication path 3072 is sometimes called a vacuum path 3072. The suction fluid communication path 3072 is used during the transfer of waste from upper waste container 4200 into storage tank 4202. A low level of vacuum can be provided by suction fluid communication path 3072 in the storage tank 4202 in order to assist with the drainage of stored waste from the upper waste container 4200 into the storage tank 4202 through transfer valve 4280. Minimizing the level of vacuum used to transfer waste reduces the requirements for the strength of storage tank 4202. This allows for the storage tank to be made with flat walls rather than cylindrical or spherical walls. A storage tank with flat sides allows much larger volumes of fluid to be stored in the same floor space. The reduced strength requirement also allows for greater flexibility in material selection and manufacturing processes.

During transfer of waste material from the upper waste container 4200 to the storage tank 4202, the vacuum present in the upper waste container 4200 is vented to atmospheric pressure through vacuum regulator 3222. The vacuum in the storage tank 4202 is set to a pressure lower than the vacuum level of the upper waste container 4200. As a result, the vacuum in the storage tank 4202 assists in pulling waste material into the storage tank 4202 through transfer valve 4280.

Once both the upper waste container 4200 and storage tank 4202 are filled, or if the user desires to empty and clean the upper waste containers 4200 and/or storage tank 4202 prior to being filled, the user can turn off vacuum pump 3210 using control panel 3162. The button 1015 (FIG. 27) is then depressed in order to de-activate electromagnet 3160. With the electromagnet 3160 de-activated, medical personnel can remove or disconnect the rover 4000 from the chassis 3100 by pulling on handle 4012 (FIG. 27) in a distal direction away from chassis 3100.

The mobile rover 4000 is then rolled from the surgical area to a static docker 900 (FIG. 4) to off-load the waste material to the treatment facility 910 (FIG. 4) and to clean waste container 4200 and storage tank 4202.

V. Fourth Embodiment

Figure 46:
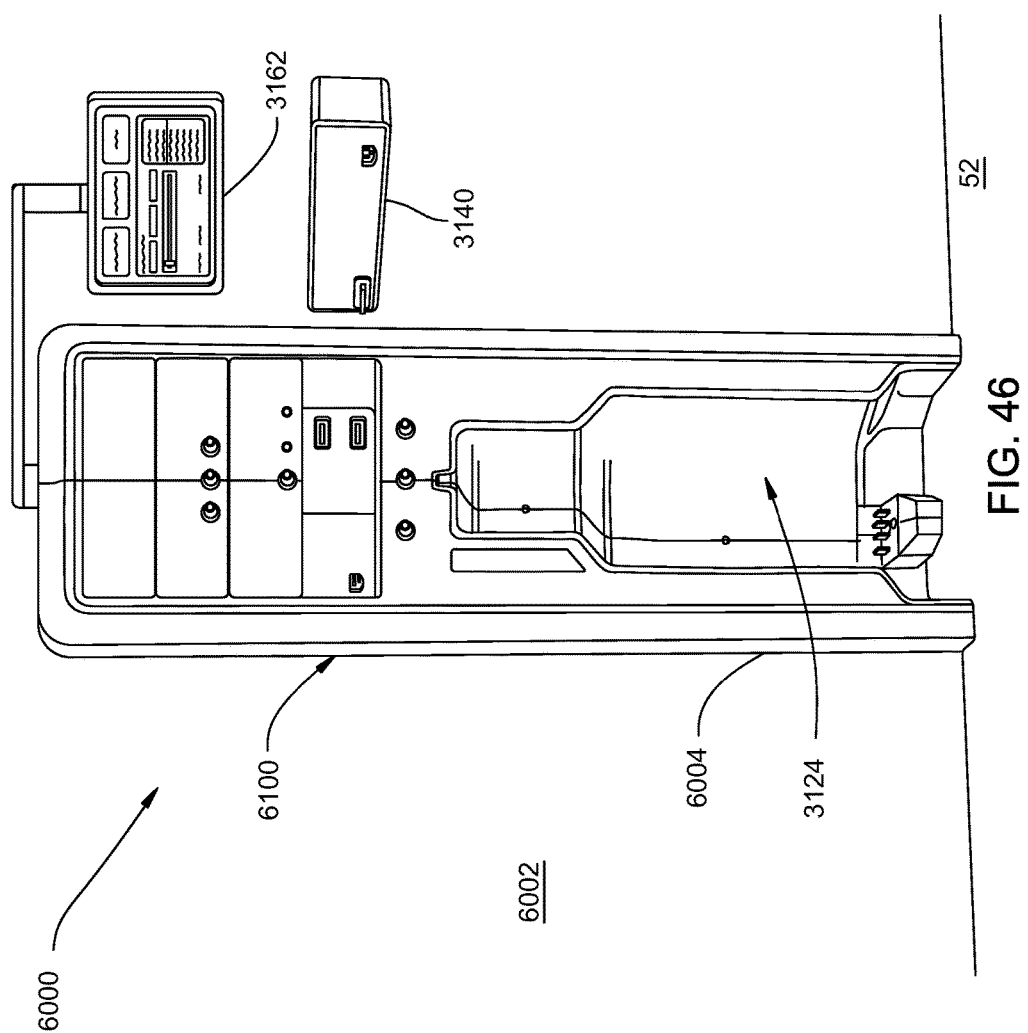
FIG. 46 is a perspective view of an alternative embodiment of a chassis.

FIG. 46 illustrates an alternative embodiment of a medical/surgical waste collection system 6000 constructed in accordance with the present invention. Waste collection system 6000 comprises a static chassis 6100 that is used with the mobile rover 4000 (FIG. 27). Static chassis 6100 is similar to chassis 3100 except that static chassis 6100 is recessed or mounted into a wall 6002 of the operating room/surgical area 52. The mounting of static chassis 6100 into wall 6202 can increase the available floor space within the operating room/surgical area 52. A peripheral flange 6004 extends outwardly from the sides and top of static chassis 6100 and extends over wall 6002. The internal components and operation of static chassis 6100 are the same as previously described for chassis 3100.

VI. Alternative Embodiments

While the invention has been described with reference to exemplary embodiments, it will be understood by those skilled in the art that various changes may be made and equivalents may be substituted for elements and features thereof without departing from the scope of the invention. For example, it is contemplated that elements and/or features of one embodiment may be combined or substituted with elements and/or features of another embodiment. In addition, many modifications may be made to adapt a particular system, device or component thereof to the teachings of the invention without departing from the essential scope thereof. It is intended that the invention not be limited to the particular embodiments disclosed for carrying out this invention.

For example, not all versions of the inventions may have all the features described. The features of the different embodiments of the invention may be combined. Likewise, there is no requirement that all versions of the invention include the described highly mobile rover 1000, 4000. In some versions of the invention rovers 1000 and 4000 can be static units.

In one embodiment, the control valves 5400 (FIG. 28) can be omitted from chassis 3100 such that when vacuum pump 3210 is in operation, continuous suction is provided to all three disposable inlet fittings 5100. In another embodiment, the control valves 5400 and inlet fittings 5100 (FIG. 28) can be removed from chassis 3100 and mounted to mobile rover 4000 with rover controller 4952 controlling the operation of control valves 5400. In this embodiment, the waste couplings 4700 and 5600 are not required and may be omitted.

In an additional embodiment of the invention, one of the surgical modules 3140 (FIG. 44) can be an irrigation pump and control system that supplies irrigation fluid to a surgical site. The surgical module 3140 can be in communication with the chassis controller 3802 (FIG. 44). When the irrigation pump operates to supply irrigation fluid to the surgical site, the controller 3802 can detect the operation of the irrigation pump and automatically turn on vacuum pump 3210 and one of control valves 5400 in order to supply suction to the surgical site. Therefore, whenever the surgical site is being flushed with irrigation fluid, one or more of the suction lines are automatically providing suction to remove waste fluids and debris generated during the surgical procedure.

In some versions of the invention the components that releasably hold the carts 100 and 1000 together may be attached to the waste collection cart 1000. Thus the magnet or moving mechanical member may be attached to cart 1000. Based on a signal from controller 802 to the suction cart 1000 the component that releasably holds the carts 100 and 1000 together is actuated and deactuated.

In not all versions of the invention will the rover include a receiver for holding a replaceable manifold. In these versions of the invention, the receiver may be a simple fitting that receives a suction line. Likewise, the receiver may be some device that receives some type of fluid coupling from which a suction line extends.

In some versions of the invention, the transmission of data and/or instruction signals between at one end the chassis or suction cart and at the other end the container cart may be a wireless connection. This connection may be either at frequencies associated with inductive coupling or higher frequencies associated with RF signal exchange.

The vacuum regulators may function differently from what is disclosed. Thus in some versions of the invention, the vacuum regulator may simply control the on/off state of the vacuum pump and/or the operating rate of the vacuum pump.

In some versions of the invention, when the rover is first mated to the chassis after the chassis controller 802 sends an interrogation request to the rover controller 1952. The rover controller 1952 must respond with the appropriate recognition code. If the chassis controller 802 does not receive the appropriate authentication code the chassis controller will not activate the pump 210. This prevents a suction from be drawn on a container not specifically designed for use with the chassis.

Therefore, it is an object of the appended claims to cover all such variations and modifications that come within the true spirit and scope of this invention.

What is claimed is:

1. An assembly for use during a medical or surgical procedure, the assembly comprising:
   a mobile chassis, said chassis shaped to define a void space dimensioned to removably receive a mobile waste collection cart that has at least one container for storing waste withdrawn from a patient wherein, said mobile chassis does not include a fluid coupling for receiving fluid from the at least one container of the waste collection cart;
   a rack integral with said chassis, said rack shaped to define at least one compartment, wherein said rack is configured to receive in the at least one compartment an instrument capable of performing at least one of: controlling the operation of a medical or surgical instrument; monitoring a biological state of a patient; or controlling the flow of fluid applied to or withdrawn from a patient;
   a vacuum pump mounted to said chassis;

a cart retention feature attached to said chassis for removably securing a mobile waste collection cart in the chassis void space so that said chassis, including said rack, and said waste collection cart can move as a single unit and be disconnected from each other so that said chassis, including said rack, and the mobile waste collection cart are able to move independently of each other; and a chassis vacuum coupling is mounted to said chassis and connected to the vacuum pump, said chassis vacuum coupling positioned so that when the waste collection cart is secured in the chassis void space, a connection is established between said chassis vacuum coupling and a complementary cart vacuum coupling to establish a path over which a vacuum can be drawn by the vacuum pump on the at least one container.

2. The assembly of claim 1, wherein said cart retention feature includes a magnet mounted to the chassis.

3. The assembly of claim 2, wherein said magnet is an electromagnet.

4. The assembly of claim 1, wherein said cart retention feature includes a component that mechanically engages the mobile waste collection cart.

5. The assembly of claim 1, wherein:
at least one receiver is attached to said chassis, said at least one receiver configured to receive a suction line that is directed towards a surgical site; and
a waste coupler separate from said chassis vacuum coupling is attached to the chassis and is configured to be coupled at a first end to a complementary second waste coupler on the mobile waste collection cart that is connected to the at least one container of the cart and at a second end to said at least one receiver for establishing a suction path from the suction line through the at least one receiver to the container of the mobile waste collection cart.

6. The assembly of claim 1, wherein a vacuum regulator is attached to said chassis for regulating the level of suction drawn on the at least one container of the mobile waste collection cart.

7. The assembly of claim 6, wherein:
a controller is mounted to said chassis and is capable of receiving data from a memory integral with the instrument mounted in the at least one compartment of said rack and to control said vacuum regulator so as to establish the level of suction drawn on the at least one container of the mobile waste collection cart and said controller is further configured to:
receive the data from the memory integral with the at least one instrument mounted to said rack; and
control said vacuum regulator so as to set the level of suction drawn on the at least one container based on the data read from the memory of the at least one instrument mounted to said rack.

8. The assembly of claim 6, wherein:
a communications circuit is mounted to the chassis for receiving a signal from the mobile waste collection cart representative of the pressure in the at least one container of the waste collection cart; and
a controller is mounted to the chassis and receives from said communications circuit the signal representative of container pressure and, based on the signal representative of container pressure, said controller controls said vacuum regulator to set the level of suction that said chassis draws on the container of the cart.

9. The assembly claim 1, further including:
a vacuum regulator attached to said chassis for regulating the level of suction drawn on the at least one container of the mobile waste collection cart; and
a control module mounted to said chassis that is connected to said vacuum regulator and that is configured for connection to the instrument mounted to the rack wherein: said control module includes a control panel through which commands are entered to regulate the level of suction drawn on the at least one container and to control the instrument; and said control module is configured to, in response to the entry of a command, communicates the command to said vacuum regulator or to the instrument.

10. The assembly of claim 1, wherein said mobile chassis and said rack are collectively configured so that the at least one compartment of said rack is located above the void space of said mobile chassis.

11. An assembly for use during a medical or surgical procedure, the assembly comprising:
a mobile chassis, said chassis shaped to define a void space dimensioned to removably receive a mobile waste collection cart that has at least one container for storing waste withdrawn from a patient, wherein said mobile chassis does not include a fluid coupling for receiving fluid discharged from the at least one container of the waste collection cart;
at least one inlet fitting mounted to said chassis, said inlet fitting configured to receive a suction line that establishes a fluid communications path from a patient;
a chassis coupler mounted to said chassis, said coupler positioned and configured so that, when the mobile waste collection cart is disposed in the void space of said chassis, a connection is established between said chassis coupler and a complementary cart coupler attached to the cart so as to establish a fluid communications path to the at least one container and wherein, said at least one inlet fitting is in fluid communications with said chassis coupler;
a valve disposed between said inlet fitting and said chassis coupler to regulate fluid flow from said inlet fitting into the at least one container of the waste collection cart;
a rack integral with said chassis, said rack shaped to define at least one compartment wherein, said rack is configured to receive in the at least one compartment an instrument capable of performing at least one of: controlling the operation of a medical or surgical instrument; monitoring a biological state of a patient; or controlling the flow of fluid applied to or withdrawn from a patient;
a vacuum pump mounted to said chassis; and
a cart retention feature attached to said chassis for removably securing a mobile waste collection cart in the chassis void space that said chassis, including said rack, and the waste collection cart can move as a single unit and be disconnected from each other so that said chassis, including said rack, and the mobile waste collection cart are able both to move independently of each other;
a chassis vacuum coupling separate from said chassis coupler is mounted to said chassis and connected to the vacuum pump, said chassis vacuum coupling positioned so that when the waste collection cart is secured in the chassis void space, a connection is established between said chassis vacuum coupling and a complementary cart vacuum coupling to establish a path over which a vacuum can be drawn by the vacuum pump on the at least one container of the mobile waste collection cart;

a vacuum regulator mounted to said chassis for regulating the level of suction drawn by said vacuum pump on the at least one container of the mobile waste collection cart; and a valve controller mounted to said chassis for selectively establishing an open/closed state of said valve.

12. The assembly of claim 11, wherein:

a plurality of said inlet fittings are mounted to said chassis for establishing plural connections between different suction lines and the at least one container of the mobile waste collection cart;

said valve comprises a plurality of valves, and each of said plurality of valves is located between each of at least two of said fittings and the at least one container for independently connecting said fittings to the at least one container; and said valve controller is connected to each of said plurality of valves for selectively establishing the open/closed state of said plurality of valves.

13. The assembly of claim 12, wherein at least two of the said plurality of valves are attached to said valve controller and can be selectively moved to: a fully open position; a closed positioned; or an at least one intermediate positon between the fully open position and the closed position to control the flow rate through each of the two valves.

14. The assembly of claim 11, wherein said valve can be selectively moved to: a fully open position; a closed positioned; or an at least one intermediate positon between the fully open position and the closed position to control the flow rate through the valve.

15. The assembly of claim 11, wherein said chassis and said inlet fitting are formed with complementary features for removably mounting said inlet fitting to said chassis.

16. The assembly of claim 11, further including a control module mounted to said chassis said control module:

being connected to said vacuum regulator and being connected to said valve controller; and configured for connection to an instrument mounted in the at least one compartment of said rack, wherein: said control module includes a control panel through which commands are entered to regulate the level of suction drawn on the at least one container; regulate the setting of said valve; and to control the instrument; and said control module is configured to, in response to the entry of a command entered through said control panel, communicates the command to said vacuum regulator, said valve controller, or to the instrument.

17. The assembly of claim 11, wherein said cart retention feature includes a magnet mounted to the chassis.

18. The assembly of claim 11, wherein said cart retention feature includes a component that mechanically engages the mobile waste collection cart.

19. The assembly of claim 11, wherein:

a processor is mounted to said chassis and is capable of receiving data from the instrument mounted in the at least one compartment of said rack and to control said vacuum regulator so as to establish the level of suction drawn on the at least one container of the mobile waste collection cart and said controller is further configured to:

receive data from the instrument mounted to the rack; and control said vacuum regulator so as to set the level of suction drawn on the at least one container based on the data read from the instrument mounted to said rack.

20. The assembly of claim 11, wherein:

a communications circuit is mounted to said chassis for receiving a signal from the mobile waste collection cart representative of the pressure in the at least one container on the mobile waste collection cart; and a controller is mounted to the chassis and receives from said communications circuit the signal representative of container pressure and, based on the signal representative of container pressure, said controller controls said vacuum regulator to set the level of suction that drawn on the container of the mobile waste collection cart.

* * * * *